United States Patent
Chen et al.

(10) Patent No.: US 9,708,326 B2
(45) Date of Patent: Jul. 18, 2017

(54) INHIBITORS OF BRUTON'S TYROSINE KINASE

(71) Applicant: Pharmacyclics LLC, Sunnyvale, CA (US)

(72) Inventors: Wei Chen, Fremont, CA (US); Shunqi Yan, Irvine, CA (US); David J. Loury, Incline Village, NV (US); Leah Lynn Frye, Portland, OR (US); Jeremy Robert Greenwood, Brooklyn, NY (US); Mee Yoo Shelley, Tigard, OR (US); Longcheng Wang, Palo Alto, CA (US)

(73) Assignee: PHARMACYCLICS LLC, Sunnyvale, CA (US)

( * ) Notice: Subject to any disclaimer, the term of this patent is extended or adjusted under 35 U.S.C. 154(b) by 0 days.

(21) Appl. No.: 14/770,438

(22) PCT Filed: Feb. 20, 2014

(86) PCT No.: PCT/US2014/017436
§ 371 (c)(1),
(2) Date: Aug. 25, 2015

(87) PCT Pub. No.: WO2014/130693
PCT Pub. Date: Aug. 28, 2014

(65) Prior Publication Data
US 2016/0002241 A1  Jan. 7, 2016

Related U.S. Application Data

(60) Provisional application No. 61/769,103, filed on Feb. 25, 2013.

(51) Int. Cl.
*C07D 473/32* (2006.01)
*C07D 487/04* (2006.01)

(52) U.S. Cl.
CPC ......... *C07D 473/32* (2013.01); *C07D 487/04* (2013.01)

(58) Field of Classification Search
CPC ............................ C07D 473/32; C07D 487/04
See application file for complete search history.

(56) References Cited

FOREIGN PATENT DOCUMENTS

| WO | WO-2006091737 A1 | 8/2006 |
|---|---|---|
| WO | WO-2007140222 A2 | 12/2007 |
| WO | WO-2009062112 A2 | 5/2009 |
| WO | WO-2009062258 A1 | 5/2009 |
| WO | WO-2009131687 A2 | 10/2009 |
| WO | WO-2010008411 A1 | 1/2010 |
| WO | WO-2013082476 A1 | 6/2013 |
| WO | WO-2014130693 A1 | 8/2014 |

OTHER PUBLICATIONS

PCT/US2014/017436 International Preliminary Report on Patentability dated Sep. 3, 2015.
PCT/US2014/017436 International Search Report and Written Opinion dated Jun. 30, 2015.
Chen, et al., "Virtual screening to successfully identify novel janus kinase 3 inhibitors: a sequential focused screening approach," J Med Chem, 51(21): 7015-7019 (2008).

*Primary Examiner* — Sahar Javanmard
(74) *Attorney, Agent, or Firm* — Foley Hoag LLP

(57) ABSTRACT

Disclosed herein are compounds that form covalent bonds with Bruton's tyrosine kinase (Btk). Also described are irreversible inhibitors of Btk. In addition, reversible inhibitors of Btk are also described. Also disclosed are pharmaceutical compositions that include the compounds. Methods of using the Btk inhibitors are disclosed, alone or in combination with other therapeutic agents, for the treatment of autoimmune diseases or conditions, heteroimmune diseases or conditions, cancer, including lymphoma, and inflammatory diseases or conditions.

18 Claims, No Drawings

INHIBITORS OF BRUTON'S TYROSINE KINASE

RELATED APPLICATIONS

This application claims the benefit of U.S. provisional patent application No. 61/769,103 entitled "INHIBITORS OF BRUTON'S TYROSINE KINASE" filed on Feb. 25, 2013, which is herein incorporated by reference in its entirety.

FIELD OF THE INVENTION

Described herein are compounds, methods of making such compounds, pharmaceutical compositions and medicaments containing such compounds, and methods of using such compounds and compositions to inhibit the activity of tyrosine kinases.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoetic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197: 1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Described herein are inhibitors of Bruton's tyrosine kinase (Btk). Also described herein are irreversible inhibitors of Btk. Also described herein are reversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs").

Also described herein are methods for synthesizing such reversible or irreversible inhibitors, methods for using such reversible or irreversible inhibitors in the treatment of diseases (including diseases wherein irreversible inhibition of Btk provides therapeutic benefit to a patient having the disease). Further described are pharmaceutical formulations that include a reversible or irreversible inhibitor of Btk.

In one aspect, provided herein is a compound of Formula (I) having the structure:

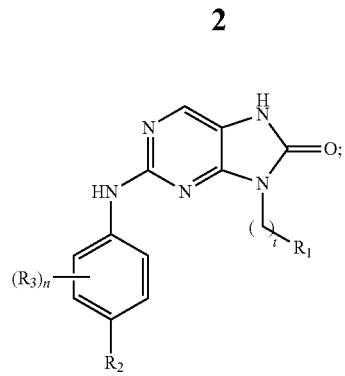

Formula (I)

wherein:
$R_1$ is optionally substituted heteroalkyl, —(C=O)$C_1$-$C_6$ alkyl, —(C=O)O$R_4$, —(C=O)N$R_4R_4$, —(C=O)S$R_4$, -G-X, or

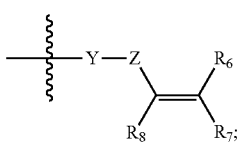

G is optionally substituted alkyl, optionally substituted cycloalkyl, optionally substituted heterocycloalkyl, optionally substituted heteroaryl, or optionally substituted aryl;

X is optionally substituted cycloalkyl, optionally substituted heterocycloalkyl, optionally substituted aryl, optionally substituted heteroaryl, —O$R_4$, —S$R_4$, —N$R_4R_4$, or -$L_2$-Ar;

each $R_4$ is each independently H, $C_1$-$C_6$ alkyl, $C_1$-$C_6$ heteroalkyl, $C_3$-$C_6$ cycloalkyl, or $C_2$-$C_6$ heterocycloalkyl;

Y is an optionally substituted group selected from among alkyl, heteroalkyl, cycloalkyl, heterocycloalkyl, aryl, and heteroaryl;

Z is C(=O), OC(=O), N($R_{21}$)C(=O), C(=S), S(=O)$_p$, OS(=O)$_p$, or N($R_{21}$)S(=O)$_p$, where p is 1 or 2;

$R_2$ is hydrogen, halogen, —CN, —NO$_2$, —OH, —O$R_{20}$, —OCF$_3$, —OCH$_2$F, —OCF$_2$H, —CF$_3$, —S$R_{21}$, —N($R_{21}$)S(=O)$_2R_{23}$, —S(=O)$_2$N($R_{21}$)($R_{22}$), —S(=O)$R_{23}$, —S(=O)$_2R_{23}$, —C(=O)$R_{23}$, —OC(=O)$R_{23}$, —CO$_2R_{21}$, —N($R_{21}$)($R_{22}$), substituted or unsubstituted alkyl, substituted or unsubstituted heteroalkyl, substituted or unsubstituted heterocycloalkyl, substituted or unsubstituted cycloalkyl, or -$L_2$-Ar;

$L_2$ is a bond, —CH$_2$—, —CH(OH)—, —C(O)—, —CH$_2$O—, —OCH$_2$—, —SCH$_2$—, —CH$_2$S—, —N($R_{21}$)—, —O—, —S—, —S(O)—, —S(O)$_2$—, —N($R_{21}$)S(O)$_2$—, or —S(O)$_2$N($R_{21}$)—;

Ar is a substituted or unsubstituted cycloalkyl, substituted or unsubstituted heterocycloalkyl, substituted or unsubstituted aryl, or a substituted or unsubstituted heteroaryl;

each $R_3$ is each independently halogen, —CN, —NO$_2$, —OH, —OCF$_3$, —OCH$_2$F, —OCF$_2$H, —CF$_3$, —S$R_{21}$, —N($R_{21}$)S(=O)$_2R_{23}$, —S(=O)$_2$N($R_{21}$)($R_{22}$), —S(=O)$R_{23}$, —S(=O)$_2R_{23}$, —C(=O)$R_{23}$, —OC(=O)$R_{23}$, —CO$_2R_{21}$, —N($R_{21}$)($R_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;

t is 0-2;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (I) wherein $R_1$ is

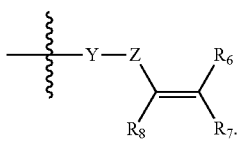

In a further embodiment is a compound of Formula (I) wherein Z is C(=O), NHC(=O), N(CH$_3$)C(=O), or S(=O)$_2$. In yet a further embodiment is a compound of Formula (I) wherein Z is NHC(=O) or N(CH$_3$)C(=O). In some embodiments is a compound of Formula (I) wherein Z is NHC(=O). In some embodiments is a compound of Formula (I) wherein Z is N(CH$_3$)C(=O). In a further embodiment is a compound of Formula (I) wherein $R_6$, $R_7$, and $R_8$ are H. In another embodiment is a compound of Formula (I) wherein $R_7$ and $R_8$ are H; and $R_6$ is $L_3$-J-W. In a further embodiment is a compound of Formula (I) wherein $R_6$ is H, substituted or unsubstituted $C_1$-$C_6$alkyl, substituted or unsubstituted $C_1$-$C_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (I) wherein $R_6$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl. In another embodiment is a compound of Formula (I) wherein $R_6$ and $R_8$ are H; and $R_7$ is $L_3$-J-W. In one embodiment is a compound of Formula (I) wherein $R_7$ is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (I) wherein $R_7$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl.

In another embodiment is a compound of Formula (I) wherein $R_6$ and $R_8$ are H; $R_7$ is $L_3$-J-W; $L_3$ is a bond, substituted or unsubstituted C$_1$-C$_6$ alkylene, or substituted or unsubstituted C$_3$-C$_6$ cycloalkylene; and J is a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In a further embodiment is a compound of Formula (I) wherein $L_3$ is —CH$_2$—. In a further embodiment is a compound of Formula (I) wherein J is substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In yet a further embodiment is a compound of Formula (I) wherein J is substituted or unsubstituted C$_1$-C$_6$ alkylene, cyclopropyl, pyrrolidinyl, piperidinyl, piperizinyl, morpholinyl, imidazolyl, pyridinyl, or phenyl. In a further embodiment is a compound of Formula (I) wherein $L_3$ is a bond. In a further embodiment is a compound of Formula (I) wherein J is substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In yet a further embodiment is a compound of Formula (I) wherein J is —CH$_2$— and W is NR$_{25}$R$_{26}$. In a further embodiment is a compound of Formula (I) wherein $R_{25}$ is H, substituted or unsubstituted C$_1$-C$_6$ alkyl, substituted or unsubstituted C$_3$-C$_6$ cycloalkyl; and $R_{26}$ is substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl. In some embodiments is a compound of Formula (I) wherein $R_{25}$ and $R_{26}$ are —CH$_3$. In some embodiments is a compound of Formula (I) wherein $R_{25}$ and $R_{26}$ are cyclopropyl. In some embodiments is a compound of Formula (I) wherein $R_{25}$ is —CH$_3$ and $R_{26}$ is cyclopropyl.

In another embodiment is a compound of Formula (I) wherein $R_7$ and $R_8$ taken together form a bond; and $R_6$ is $L_3$-J-W. In another embodiment is a compound of Formula (I) wherein $R_6$ is is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (I) wherein $R_6$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl. In yet another embodiment is a compound of Formula (I) wherein $R_6$ is substituted or unsubstituted C$_1$-C$_6$alkyl, or C$_1$-C$_8$alkylaminoalkyl.

In another embodiment is a compound of Formula (I) wherein $R_2$ is halogen, —$OR_{20}$, or substituted or unsubstituted alkyl. In another embodiment is a compound of Formula (I) wherein $R_2$ is -$L_2$-Ar. In a further embodiment is a compound of Formula (I) wherein $L_2$ is —O— and Ar is phenyl.

In another embodiment of the aforementioned embodiments is a compound of Formula (I) wherein Y is aryl. In another embodiment of the aforementioned embodiments is a compound of Formula (I) wherein Y is heterocycloalkyl. In another embodiment of the aforementioned embodiments is a compound of Formula (I) wherein Y is cycloalkyl. In a further embodiment of the aforementioned embodiments is a compound of Formula (I) wherein t is 0. In a further embodiment of the aforementioned embodiments is a compound of Formula (I) wherein n is 0.

In another aspect, provided herein is a compound of Formula (II) having the structure:

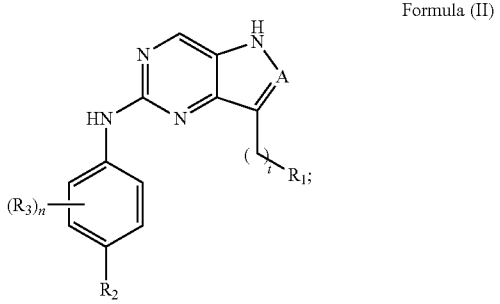

Formula (II)

wherein:
A is =C($R_9$)—, or =N—;
$R_1$ is substituted or unsubstituted alkoxy, substituted or unsubstituted heteroalkyl, substituted or unsubstituted heterocycloalkyl, substituted or unsubstituted cycloalkyl, substituted or unsubstituted heteroaryl, substituted aryl, —(C=O)$C_1$-$C_6$ alkyl, —(C=O)O$R_4$, —(C=O)N$R_4R_4$, —(C=O)S$R_4$, -G-X, —Y-$L_2$-Ar, or

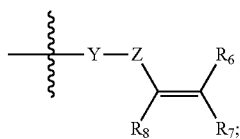

G is optionally substituted alkyl;
X is optionally substituted cycloalkyl, optionally substituted heterocycloalkyl, optionally substituted aryl, optionally substituted heteroaryl, —O$R_4$, —S$R_4$, —N$R_4R_4$, or -$L_2$-Ar;
each $R_4$ is each independently H, $C_1$-$C_6$ alkyl, $C_1$-$C_6$ heteroalkyl, $C_3$-$C_6$ cycloalkyl, or $C_2$-$C_6$ heterocycloalkyl;
Y is an optionally substituted group selected from among alkyl, heteroalkyl, cycloalkyl, heterocycloalkyl, aryl, and heteroaryl;
$R_2$ is hydrogen, halogen, —CN, —$NO_2$, —OH, —$OR_{20}$, —$OCF_3$, —$OCH_2F$, —$OCF_2H$, —$CF_3$, —$SR_{21}$, —N($R_{21}$)S(=O)$_2R_{23}$, —S(=O)$_2$N($R_{21}$)($R_{22}$), —S(=O)$R_{23}$, —S(=O)$_2R_{23}$, —C(=O)$R_{23}$, —OC(=O)$R_{23}$, —$CO_2R_{21}$, —N($R_{21}$)($R_{22}$), substituted or unsubstituted alkyl, substituted or unsubstituted heteroalkyl, substituted or unsubstituted heterocycloalkyl, substituted or unsubstituted cycloalkyl, or -$L_2$-Ar;
$L_2$ is a bond, —$CH_2$—, —CH(OH)—, —C(O)—, —$CH_2O$—, —$OCH_2$—, —$SCH_2$—, —$CH_2S$—, —N($R_{21}$)—, —O—, —S—, —S(O)—, —S(O)$_2$—, —N($R_{21}$)S(O)$_2$—, or —S(O)$_2$N($R_{21}$)—;
Ar is a substituted or unsubstituted cycloalkyl, substituted or unsubstituted heterocycloalkyl, substituted or unsubstituted aryl, or a substituted or unsubstituted heteroaryl;
Z is C(=O), OC(=O), N($R_{21}$)C(=O), C(=S), S(=O)$_p$, OS(=O)$_x$, or N($R_{21}$)S(=O)$_p$, where p is 1 or 2;
each $R_3$ is each independently halogen, —CN, —$NO_2$, —OH, —$OCF_3$, —$OCH_2F$, —$OCF_2H$, —$CF_3$, —$SR_{21}$, —N($R_{21}$)S(=O)$_2R_{23}$, —S(=O)$_2$N($R_{21}$)($R_{22}$), —S(=O)$R_{23}$, —S(=O)$_2R_{23}$, —C(=O)$R_{23}$, —OC(=O)$R_{23}$, —$CO_2R_{21}$, —N($R_{21}$)($R_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;
$R_{20}$ is substituted or unsubstituted $C_1$-$C_6$alkyl, substituted or unsubstituted $C_1$-$C_8$heteroalkyl, or substituted or unsubstituted phenyl;
each $R_{21}$ and $R_{22}$ are each independently H, substituted or unsubstituted $C_1$-$C_6$alkyl, or substituted or unsubstituted $C_3$-$C_8$cycloalkyl;
$R_{23}$ is each independently substituted or unsubstituted $C_1$-$C_6$alkyl, or substituted or unsubstituted $C_3$-$C_8$cycloalkyl;
n is 0-4;
$R_9$ is H, halogen, —CN, —OH, —$NH_2$, —SH, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;
$R_6$ is H, halogen, —CN, or $L_3$-J-W;
$R_7$ and $R_8$ are independently H, halogen, —CN, or $L_3$-J-W; or $R_7$ and $R_8$ taken together form a bond;
each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;
each W is H, —CN, or —$NR_{25}R_{26}$;
$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or
a pharmaceutically acceptable solvate, pharmaceutically acceptable salt, or pharmaceutically acceptable prodrug thereof.

In one embodiment is a compound of Formula (II) wherein $R_1$ is

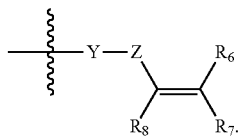

In a further embodiment is a compound of Formula (II) wherein Z is C(=O), NHC(=O), N(CH$_3$)C(=O), or S(=O)$_2$. In yet a further embodiment is a compound of Formula (II) wherein Z is NHC(=O) or N(CH$_3$)C(=O). In some embodiments is a compound of Formula (II) wherein Z is NHC(=O). In some embodiments is a compound of Formula (II) wherein Z is N(CH$_3$)C(=O). In a further embodiment is a compound of Formula (II) wherein R$_6$, R$_7$, and R$_8$ are H. In another embodiment is a compound of Formula (II) wherein R$_7$ and R$_8$ are H; and R$_6$ is L$_3$-J-W. In a further embodiment is a compound of Formula (II) wherein R$_6$ is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (II) wherein R$_6$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl. In another embodiment is a compound of Formula (II) wherein R$_6$ and R$_8$ are H; and R$_7$ is L$_3$-J-W. In one embodiment is a compound of Formula (II) wherein R$_7$ is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (II) wherein R$_7$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl.

In another embodiment is a compound of Formula (II) wherein R$_6$ and R$_8$ are H; R$_7$ is L$_3$-J-W; L$_3$ is a bond, substituted or unsubstituted C$_1$-C$_6$ alkylene, or substituted or unsubstituted C$_3$-C$_6$ cycloalkylene; and J is a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In a further embodiment is a compound of Formula (II) wherein L$_3$ is —CH$_2$—. In a further embodiment is a compound of Formula (II) wherein J is substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In yet a further embodiment is a compound of Formula (II) wherein J is substituted or unsubstituted C$_1$-C$_6$ alkylene, cyclopropyl, pyrrolidinyl, piperidinyl, piperizinyl, morpholinyl, imidazolyl, pyridinyl, or phenyl. In a further embodiment is a compound of Formula (II) wherein L$_3$ is a bond. In a further embodiment is a compound of Formula (II) wherein J is substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, or substituted or unsubstituted C$_3$-C$_{12}$ heteroarylene. In yet a further embodiment is a compound of Formula (II) wherein J is —CH$_2$— and W is NR$_{25}$R$_{26}$. In a further embodiment is a compound of Formula (II) wherein R$_{25}$ is H, substituted or unsubstituted C$_1$-C$_6$ alkyl, substituted or unsubstituted C$_3$-C$_6$ cycloalkyl; and R$_{26}$ is substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl. In some embodiments is a compound of Formula (II) wherein R$_{25}$ and R$_{26}$ are —CH$_3$. In some embodiments is a compound of Formula (II) wherein R$_{25}$ and R$_{26}$ are cyclopropyl. In some embodiments is a compound of Formula (II) wherein R$_{25}$ is —CH$_3$ and R$_{26}$ is cyclopropyl.

In another embodiment is a compound of Formula (II) wherein R$_7$ and R$_8$ taken together form a bond; and R$_6$ is L$_3$-J-W. In another embodiment is a compound of Formula (II) wherein R$_6$ is is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (II) wherein R$_6$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl. In yet another embodiment is a compound of Formula (II) wherein R$_6$ is substituted or unsubstituted C$_1$-C$_6$alkyl, or C$_1$-C$_8$alkylaminoalkyl.

In another embodiment is a compound of Formula (II) wherein R$_2$ is halogen, —OR$_{20}$, or substituted or unsubstituted alkyl. In another embodiment is a compound of Formula (II) wherein R$_2$ is -L$_2$-Ar. In a further embodiment is a compound of Formula (II) wherein L$_2$ is —O— and Ar is phenyl.

In another embodiment is a compound of Formula (II) wherein Y is aryl. In another embodiment is a compound of Formula (II) wherein Y is heterocycloalkyl. In another embodiment is a compound of Formula (II) wherein Y is cycloalkyl. In a further embodiment of the aforementioned embodiments is a compound of Formula (II) wherein t is 0. In a further embodiment of the aforementioned embodiments is a compound of Formula (II) wherein n is 0. In a further embodiment of the aforementioned embodiments is a compound of Formula (II) wherein A is =C(R$_9$)—. In another embodiment of the aforementioned embodiments is a compound of Formula (II) wherein A is =N—.

In another aspect is a pharmaceutical composition comprising a therapeutically effective amount of a compound of Formula (I) or (II) and a pharmaceutically acceptable excipient. In one embodiment, the pharmaceutical composition comprising the compound of Formula (I) or (II) is formulated for a route of administration selected from oral administration, parenteral administration, buccal administration, nasal administration, topical administration, or rectal administration. In another aspect is a method for treating an autoimmune disease or condition comprising administering to a patient in need a therapeutically effective amount of a compound of Formula (I) or (II). In one embodiment the autoimmune disease is selected from rheumatoid arthritis or lupus. In a further aspect is a method for treating a heteroimmune disease or condition comprising administering to a patient in need a therapeutically effective amount of a compound of Formula (I) or (II). In yet another embodiment is a method for treating a cancer comprising administering to a patient in need a therapeutically effective amount of a compound of Formula (I) or (II). In one embodiment the cancer is a B-cell proliferative disorder.

In another embodiment the B-cell proliferative disorder is diffuse large B cell lymphoma, follicular lymphoma or chronic lymphocytic leukemia.

In yet a further aspect is a method for treating mastocytosis comprising administering to a patient in need a therapeutically effective amount of a compound of Formula (I) or (II).

In another aspect is a method for treating osteoporosis or bone resorption disorders comprising administering to a patient in need a therapeutically effective amount of a compound of Formula (I) or (II).

In a further aspect is a method for treating an inflammatory disease or condition comprising administering to a patient in need a therapeutically effective amount of a compound of Formula (I) or (II).

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In a further aspect are provided pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In one aspect, provided herein are methods for treating a patient by administering a compound provided herein. In some embodiments, provided herein is a method of inhibiting the activity of tyrosine kinase(s), such as Btk, or of treating a disease, disorder, or condition, which would benefit from inhibition of tyrosine kinase(s), such as Btk, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which would benefit from inhibition of Bruton's tyrosine kinase (Btk) activity.

In some embodiments, compounds provided herein are administered to a human.

In some embodiments, compounds provided herein are orally administered.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of tyrosine kinase(s), such as Btk, are provided.

In another aspect are inhibited tyrosine kinases comprising a Bruton's tyrosine kinase covalently bound to an inhibitor having the structure:

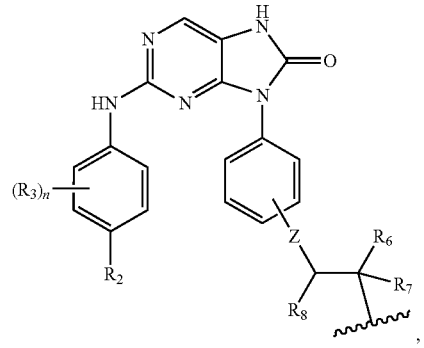

wherein ⌇ indicates the point of attachment between the inhibitor and the tyrosine kinase. In a further embodiment, the inhibitor is covalently bound to a cysteine residue on the tyrosine kinase.

In another aspect are inhibited tyrosine kinases comprising a Bruton's tyrosine kinase, a Bruton's tyrosine kinase homolog, or a Btk tyrosine kinase cysteine homolog thereof covalently bound to an inhibitor having the structure:

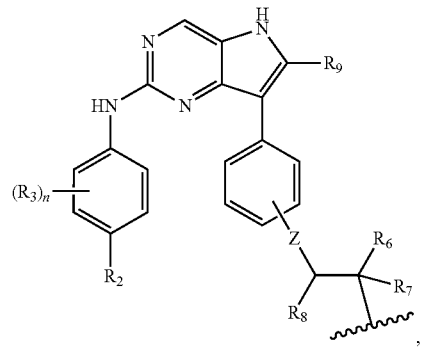

wherein ⌇ indicates the point of attachment between the inhibitor and the tyrosine kinase. In a further embodiment, the inhibitor is covalently bound to a cysteine residue on the tyrosine kinase.

In another aspect are inhibited tyrosine kinases comprising a Bruton's tyrosine kinase, a Bruton's tyrosine kinase homolog, or a Btk tyrosine kinase cysteine homolog thereof covalently bound to an inhibitor having the structure:

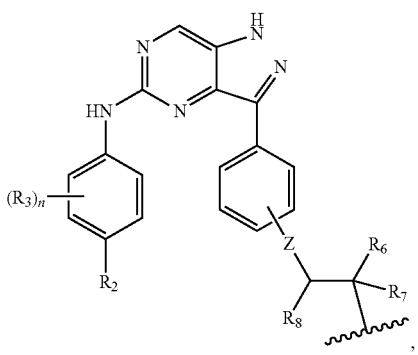

wherein ⌇ indicates the point of attachment between the inhibitor and the tyrosine kinase. In a further embodiment, the inhibitor is covalently bound to a cysteine residue on the tyrosine kinase.

In a further aspect, provided herein is a method for inhibiting Bruton's tyrosine kinase in a subject in need thereof by administering to the subject thereof a composition containing a therapeutically effective amount of at least one compound having the structure of Formula (I), (Ia), (Ib), (Ic), (Id), (II), (IIa), (III), (IIIa), (IV), or (IVa). In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of at least one compound having the structure of Formula (I), (Ia), (Ib), (Ic), (Id), (II), (IIa), (III), (IIIa), (IV), or (IVa). In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of Formula (I), (Ia), (Ib), (Ic), (Id), (II), (IIa), (III), (IIIa), (IV), or (IVa). In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (I), (Ia), (Ib), (Ic), (Id), (II), (IIa), (III), (IIIa), (IV), or (IVa). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (I), (Ia), (Ib), (Ic), (Id), (II), (IIa), (III), (IIIa), (IV), or (IVa). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (I), (Ia), (Ib), (Ic), (Id), (II), (IIa), (III), (IIIa), (IV), or (IVa). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating a heteroimmune condition or disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating an inflammatory disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase. In yet another aspect, provided herein is a method for treating a cancer by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect, provided herein is a method for treating a thromboembolic disorder by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of Formula (I), (Ia), (Ib), (Ic), (Id), (II), (IIa), (III), (IIIa), (IV), or (IVa). In another aspect are methods for modulating, including including reversibly or irreversibly inhibiting, the activity of Btk in a mammal comprising administering to the mammal at least once an effective amount of at least one compound having the structure of Formula (I), (Ia), (Ib), (Ic), (Id), (II), (IIa), (III), (IIIa), (IV), or (IVa). In another aspect are methods for treating Btk-dependent or Btk mediated conditions or diseases, comprising administering to the mammal at least once an effective amount of at least one compound having the structure of Formula (I), (Ia), (Ib), (Ic), (Id), (II), (IIa), (III), (IIIa), (IV), or (IVa).

In another aspect are methods for treating inflammation comprising administering to the mammal at least once an effective amount of at least one compound having the structure of Formula (I), (Ia), (Ib), (Ic), (Id), (II), (IIa), (III), (IIIa), (IV), or (IVa).

A further aspect are methods for the treatment of cancer comprising administering to the mammal at least once an effective amount of at least one compound having the structure of Formula (I), (Ia), (Ib), (Ic), (Id), (II), (IIa), (III), (IIIa), (IV), or (IVa). The type of cancer may include, but is not limited to, pancreatic cancer and other solid or hematological tumors.

In another aspect are methods for treating respiratory diseases comprising administering to the mammal at least once an effective amount of at least one compound having the structure of Formula (I), (Ia), (Ib), (Ic), (Id), (II), (IIa), (III), (IIIa), (IV), or (IVa). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, In another aspect are methods for preventing rheumatoid arthritis and osteoarthritis comprising administering to the mammal at least once an effective amount of at least one compound having the structure of Formula (I), (Ia), (Ib), (Ic), (Id), (II), (IIa), (III), (IIIa), (IV), or (IVa).

In another aspect are methods for treating inflammatory responses of the skin comprising administering to the mammal at least once an effective amount of at least one compound having the structure of Formula (I), (Ia), (Ib), (Ic), (Id), (II), (IIa), (III), (IIIa), (IV), or (IVa). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of Formula (I), (Ia), (Ib), (Ic), (Id), (II), (IIa), (III), (IIIa), (IV), or (IVa).

In another aspect is the use of a compound of Formula (I), (Ia), (Ib), (Ic), (Id), (II), (IIa), (III), (IIIa), (IV), or (IVa) in the manufacture of a medicament for treating an inflammatory disease or condition in an animal in which the activity of Btk or other tyrosine kinases, wherein the other tyrosine kinases share homology with Btk by having a cysteine residue (including a Cys 481 residue) that can form a covalent bond with at least one irreversible inhibitor described herein, contributes to the pathology and/or symptoms of the disease or condition. In one embodiment of this aspect, the tyrosine kinase protein is Btk. In another or further embodiment of this aspect, the inflammatory disease or conditions are respiratory, cardiovascular, or proliferative diseases.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (I) the effective amount of the compound is administered rectally to the mammal.

In any of the aforementioned aspects are further embodiments comprising single administrations of the effective amount of the compound, including further embodiments in which (I) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (I) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the prevention or treatment of Btk-dependent or tyrosine kinase mediated diseases or conditions are further embodiments comprising identifying patients by screening for a tyrosine kinase gene haplotype. In further or alternative embodiments the tyrosine kinase gene haplotype is a tyrosine kinase pathway gene, while in still further or alternative embodiments, the tyrosine kinase gene haplotype is a Btk haplotype.

In a further or alternative embodiment, the compound of formula (I), (Ia), (Ib), (Ic), (Id), (II), (IIa), (III), (IIIa), (IV), or (IVa) are reversible inhibitors of Bruton's tyrosine kinase (Btk), while in still further or alternative embodiments, such reversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In further or alternative embodiment, the compound of formula (I), (Ia), (Ib), (Ic), (Id), (II), (IIa), (III), (IIIa), (IV), or (IVa) are selective reversible inhibitors for Btk over Itk. In further or alternative embodiment, the compound of formula (I), (Ia), (Ib), (Ic), (Id), (II), (IIa), (III), (IIIa), (IV), or (IVa) are selective reversible inhibitors for Btk over Lck. In further or alternative embodiment, the compound of formula (I), (Ia), (Ib), (Ic), (Id), (II), (IIa), (III), (IIIa), (IV), or (IVa) are selective reversible inhibitors for Btk over ABL. In further or alternative embodiment, the compound of (I), (Ia), (Ib), (Ic), (Id), (II), (IIa), (III), (IIIa), (IV), or (IVa) are selective reversible inhibitors for Btk over CMET. In further or alternative embodiment, the compound of formula (I), (Ia), (Ib), (Ic), (Id), (II), (IIa), (III), (IIIa), (IV), or (IVa) are selective reversible inhibitors for Btk over EGFR. In further or alternative embodiment, the compound of formula (I), (Ia), (Ib), (Ic), (Id), (II), (IIa), (III), (IIIa), (IV), or (IVa) are selective reversible inhibitors for Btk over Lyn.

In further or alternative embodiments, the reversible Btk inhibitors are also inhibitors of EGFR.

In a further or alternative embodiment, the compound of Formula (I), (Ia), (Ib), (Ic), (Id), (II), (IIa), (III), (IIIa), (IV), or (IVa) are irreversible inhibitors of Bruton's tyrosine kinase (Btk), while in still further or alternative embodiments, such irreversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In further or alternative embodiment, the compound of Formula (I), (Ia), (Ib), (Ic), (Id), (II), (IIa), (III), (IIIa), (IV), or (IVa) are selective irreversible inhibitors for Btk over Itk. In further or alternative embodiment, the compound of Formula (I), (Ia), (Ib), (Ic), (Id), (II), (IIa), (III), (IIIa), (IV), or (IVa) are selective irreversible inhibitors for Btk over Lck. In further or alternative embodiment, the compound of Formula (I), (Ia), (Ib), (Ic), (Id), (II), (IIa), (III), (IIIa), (IV), or (IVa) are selective irreversible inhibitors for Btk over ABL. In further or alternative embodiment, the compound of (I), (Ia), (Ib), (Ic), (Id), (II), (IIa), (III), (IIIa), (IV), or (IVa) are selective irreversible inhibitors for Btk over CMET. In further or alternative embodiment, the compound of Formula (I), (Ia), (Ib), (Ic), (Id), (II), (IIa), (III), (IIIa), (IV), or (IVa) are selective irreversible inhibitors for Btk over EGFR. In further or alternative embodiment, the compound of Formula (I), (Ia), (Ib), (Ic), (Id), (II), (IIa), (III), (IIIa), (IV), or (IVa) are selective irreversible inhibitors for Btk over Lyn.

In further or alternative embodiments, the irreversible Btk inhibitors are also inhibitors of EGFR.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.
Certain Terminology Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

The alkyl group could also be a "lower alkyl" having 1 to 6 carbon atoms.

As used herein, $C_1$-$C_x$ includes $C_1$-$C_2$, $C_1$-$C_3$ ... $C_1$-$C_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Halo" or "halogen" refers to bromo, chloro, fluoro or iodo substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

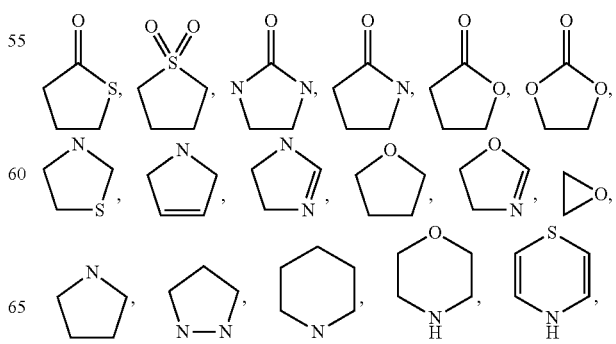

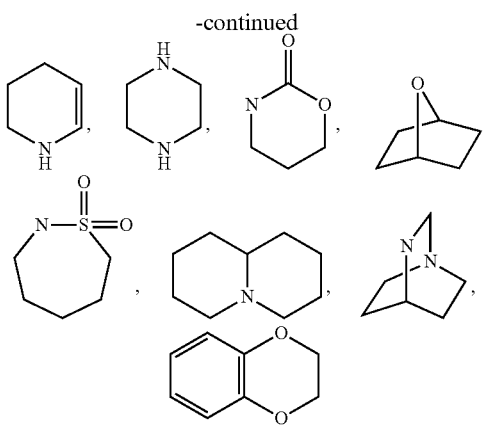

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

An "alkoxy" group refers to a (alkyl)O— group, where alkyl is as defined herein.

An "aryloxy" group refers to an (aryl)O— group, where aryl is as defined herein.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, $-CH_2-O-CH_3$, $-CH_2-CH_2-O-CH_3$, $-CH_2-NH-CH_3$, $-CH_2-CH_2-NH-CH_3$, $-CH_2-N(CH_3)-CH_3$, $-CH_2-CH_2-NH-CH_3$, $-CH_2-CH_2-N(CH_3)-CH_3$, $-CH_2-S-CH_2-CH_3$, $-CH_2-CH_2-$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. In addition, up to two heteroatoms may be consecutive, such as, by way of example, $-CH_2-NH-OCH_3$ and $-CH_2-O-Si(CH_3)_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

An "isocyanato" group refers to a $-NCO$ group.

An "isothiocyanato" group refers to a $-NCS$ group.

The term "moiety" refers to a specific segment or functional group of a molecule. Chemical moieties are often recognized chemical entities embedded in or appended to a molecule.

A "thioalkoxy" or "alkylthio" group refers to a $-S$-alkyl group.

A "alkylthioalkyl" group refers to an alkyl group substituted with a $-S$-alkyl group.

As used herein, the term "O-carboxy" or "acyloxy" refers to a group of formula $RC(=O)O-$.

"Carboxy" means a $-C(O)OH$ radical.

As used herein, the term "acetyl" refers to a group of formula $-C(=O)CH_3$.

"Acyl" refers to the group $-C(O)R$.

As used herein, the term "trihalomethanesulfonyl" refers to a group of formula $X_3CS(=O)_2-$ where X is a halogen.

"Cyanoalkyl" means an alkyl radical, as defined herein, substituted with at least one cyano group.

As used herein, the term "N-sulfonamido" or "sulfonylamino" refers to a group of formula $RS(=O)_2NH-$.

As used herein, the term "O-carbamyl" refers to a group of formula $-OC(=O)NR_2$.

As used herein, the term "N-carbamyl" refers to a group of formula $ROC(=O)NH-$.

As used herein, the term "O-thiocarbamyl" refers to a group of formula $-OC(=S)NR2$.

As used herein, "N-thiocarbamyl" refers to a group of formula $ROC(=S)NH-$.

As used herein, the term "C-amido" refers to a group of formula $-C(=O)NR2$.

"Aminocarbonyl" refers to a $-CONH2$ radical.

As used herein, the term "N-amido" refers to a group of formula $RC(=O)NH-$.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the $-N(alkyl)_xH_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula $-C(O)NHR$ or $-NHC(O)R$, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein by reference in its entirety.

The term "ester" refers to a chemical moiety with formula $-COOR$, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$alkyl), (substituted or unsubstituted $C_3$-$C_6$cycloalkyl), heteroaryl, or heteroalkyl. The protecting groups that may form the protective derivatives of the above substituents are known to those of skill in the art and may be found in references such as Greene and Wuts, above.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The "G" groups presented in any of Formula (A), Formula (B), or Formula (C) are non-limiting examples of Michael acceptor moieties.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Micheal acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (I), (Ia), (Ib), (Ic), (Id), (II), (IIa), (III), (IIIa), (IV), or (IVa), dosed that is delivered into the general circulation of the animal or human being studied. The total exposure $(AUC_{(0-\infty)})$ of a drug when administered intravenously is usually defined as 100% bioavailable (F %). "Oral bioavailability" refers to the extent to which compounds disclosed herein, such as, compounds of any of Formula (I), (Ia), (Ib), (Ic), (Id), (II), (IIa), (III), (IIIa), (IV), or (IVa), are absorbed into the general circulation when the pharmaceutical composition is taken orally as compared to intravenous injection.

"Blood plasma concentration" refers to the concentration of compounds disclosed herein, such as, compounds of any of Formula (I), (Ia), (Ib), (Ic), (Id), (II), (IIa), (III), (IIIa), (IV), or (IVa), in the plasma component of blood of a subject. It is understood that the plasma concentration of compounds of any of Formula (I), (Ia), (Ib), (Ic), (Id), (II), (IIa), (III), (IIIa), (IV), or (IVa), may vary significantly between subjects, due to variability with respect to metabolism and/or possible interactions with other therapeutic agents. In accordance with one embodiment disclosed herein, the blood plasma concentration of the compounds of any of Formula (I), (Ia), (Ib), (Ic), (Id), (II), (IIa), (III), (IIIa), (IV), or (IVa), may vary from subject to subject. Likewise, values such as maximum plasma concentration ($C_{max}$) or time to reach maximum plasma concentration ($T_{max}$), or total area under the plasma concentration time curve $(AUC_{(0-\infty)})$ may vary from subject to subject. Due to this variability, the amount necessary to constitute "a therapeutically effective amount" of a compound of any of Formula (I), (Ia), (Ib), (Ic), (Id), (II), (IIa), (III), (IIIa), (IV), or (IVa), may vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (I), (Ia), (Ib), (Ic), (Id), (II), (IIa), (III), (IIIa), (IV), or (IVa), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor. In contrast, a reversible inhibitor compound upon contact with a target protein does not cause the formation of a new covalent bond with or within the protein and therefore can associate and dissociate from the target protein.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulater refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the IC$_{50}$ refers to an amount, concentration or dosage of a particular test compound that achieves a 50% inhibition of a maximal response, such as inhibition of Btk, in an assay that measures such response.

As used herein, EC$_{50}$ refers to a dosage, concentration or amount of a particular test compound that elicits a dose-dependent response at 50% of maximal expression of a particular response that is induced, provoked or potentiated by the particular test compound.

DETAILED DESCRIPTION OF THE INVENTION

The methods described herein include administering to a subject in need a composition containing a therapeutically effective amount of one or more reversible or irreversible Btk inhibitor compounds described herein. Without being bound by theory, the diverse roles played by Btk signaling in various hematopoietic cell functions, e.g., B-cell receptor activation, suggests that small molecule Btk inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the irreversible Btk inhibitor compounds described herein can be used to inhibit a small subset of other tyrosine kinases that share homology with Btk by having a cysteine residue (including a Cys 481 residue) that can form a covalent bond with the irreversible inhibitor. Thus, a subset of tyrosine kinases other than Btk are also expected to be useful as therapeutic targets in a number of health conditions.

In some embodiments, the methods described herein can be used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/ Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions are known in the art. See, e.g., *Harrison's Principles of Internal Medicine©,*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of reversible or irreversible Btk inhibitor compounds for treating any of the foregoing diseases.

For example, dosing of reversible or irreversible Btk inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837.

In another example, dosing of reversible or irreversible Btk inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an irreversible Btk inhibitor. Cellular assays known in the art can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to a subject can be increased or decreased as needed so as to maintain a level of Btk inhibition optimal for treating the subject's disease state.

Compounds

In the following description of reversible or irreversible Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for Btk (e.g., human Btk) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The Btk inhibitor compounds described herein are selective for Btk and kinases having a cysteine residue in an amino acid sequence position of the tyrosine kinase that is homologous to the amino acid sequence position of cysteine 481 in Btk. Inhibitor compounds described herein include a Michael acceptor moiety.

Generally, a reversible or irreversible inhibitor compound of Btk used in the methods described herein is identified or characterized in an in vitro assay, e.g., an acellular biochemical assay or a cellular functional assay. Such assays are useful to determine an in vitro $IC_{50}$ for a reversible or irreversible Btk inhibitor compound.

For example, an acellular kinase assay can be used to determine Btk activity after incubation of the kinase in the absence or presence of a range of concentrations of a candidate irreversible Btk inhibitor compound. If the candidate compound is in fact an irreversible Btk inhibitor, Btk kinase activity will not be recovered by repeat washing with inhibitor-free medium. See, e.g., J. B. Smaill, et al. (1999), *J. Med. Chem.* 42(10):1803-1815. Further, covalent complex formation between Btk and a candidate irreversible Btk inhibitor is a useful indicator of irreversible inhibition of Btk that can be readily determined by a number of methods known in the art (e.g., mass spectrometry). For example, some irreversible Btk-inhibitor compounds can form a covalent bond with Cys 481 of Btk (e.g., via a Michael reaction).

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate irreversible Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of reversible or irreversible Btk compounds without undue effort.

Reversible or irreversible Btk inhibitor compounds can used for the manufacture of a medicament for treating any of the foregoing conditions (e.g., autoimmune diseases, inflammatory diseases, allergy disorders, B-cell proliferative disorders, or thromboembolic disorders).

In some embodiments, the reversible or irreversible Btk inhibitor compound used for the methods described herein inhibits Btk or a Btk homolog kinase activity with an in vitro $IC_{50}$ of less than about 10 µM. (e.g., less than about 1 µM, less than about 0.5 µM, less than about 0.4 µM, less than about 0.3 µM, less than about 0.1, less than about 0.08 µM, less than about 0.06 µM, less than about 0.05 µM, less than about 0.04 µM, less than about 0.03 µM, less than about 0.02 µM, less than about 0.01, less than about 0.008 µM, less than about 0.006 µM, less than about 0.005 µM, less than about 0.004 µM, less than about 0.003 µM, less than about 0.002 µM, less than about 0.001, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092, or less than about 0.00090 µM).

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Described herein are compounds of any of Formula (I), (Ia), (Ib), (Ic), (Id), (II), (IIa), (III), (IIIa), (IV), and (IVa). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (I), (Ia), (Ib), (Ic), (Id), (II), (IIa), (III), (IIIa), (IV), and (IVa), are also provided.

In another embodiment are compounds having the structure of Formula (I):

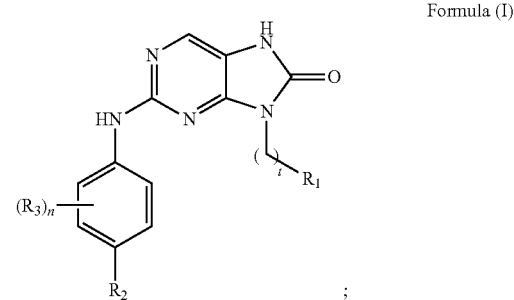

Formula (I)

wherein:
R$_1$ is optionally substituted heteroalkyl, —(C=O)C$_1$-C$_6$ alkyl, —(C=O)OR$_4$, —(C=O)NR$_4$R$_4$, —(C=O)SR$_4$, -G-X, or

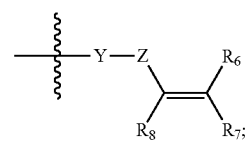

G is optionally substituted alkyl, optionally substituted cycloalkyl, optionally substituted heterocycloalkyl, optionally substituted heteroaryl, or optionally substituted aryl;

X is optionally substituted cycloalkyl, optionally substituted heterocycloalkyl, optionally substituted aryl, optionally substituted heteroaryl, —OR$_4$, —SR$_4$, —NR$_4$R$_4$, or -L$_2$-Ar;

each R$_4$ is each independently H, C$_1$-C$_6$ alkyl, C$_1$-C$_6$ heteroalkyl, C$_3$-C$_6$ cycloalkyl, or C$_2$-C$_6$ heterocycloalkyl;

Y is an optionally substituted group selected from among alkyl, heteroalkyl, cycloalkyl, heterocycloalkyl, aryl, and heteroaryl;

Z is C(=O), OC(=O), N($R_{21}$)C(=O), C(=S), S(=O)$_p$, OS(=O)$_p$, or N($R_{21}$)S(=O)$_p$, where p is 1 or 2;

$R_2$ is hydrogen, halogen, —CN, —NO$_2$, —OH, —OR$_{20}$, —OCF$_3$, —OCH$_2$F, —OCF$_2$H, —CF$_3$, —SR$_{21}$, —N($R_{21}$)S(=O)$_2$R$_{23}$, —S(=O)$_2$N($R_{21}$)($R_{22}$), —S(=O)R$_{23}$, —S(=O)$_2$R$_{23}$, —C(=O)R$_{23}$, —OC(=O)R$_{23}$, —CO$_2$R$_{21}$, —N($R_{21}$)($R_{22}$), substituted or unsubstituted alkyl, substituted or unsubstituted heteroalkyl, substituted or unsubstituted heterocycloalkyl, substituted or unsubstituted cycloalkyl, or -$L_2$-Ar;

$L_2$ is a bond, —CH$_2$—, —CH(OH)—, —C(O)—, —CH$_2$O—, —OCH$_2$—, —SCH$_2$, —CH$_2$S—, —N($R_{21}$)—, —O—, —S—, —S(O)—, —S(O)$_2$—, —N($R_{21}$)S(O)$_2$—, or —S(O)$_2$N($R_{21}$)—;

Ar is a substituted or unsubstituted cycloalkyl, substituted or unsubstituted heterocycloalkyl, substituted or unsubstituted aryl, or a substituted or unsubstituted heteroaryl;

each $R_3$ is each independently halogen, —CN, —NO$_2$, —OH, —OCF$_3$, —OCH$_2$F, —OCF$_2$H, —CF$_3$, —SR$_{21}$, —N($R_{21}$)S(=O)$_2$R$_{23}$, —S(=O)$_2$N($R_{21}$)($R_{22}$), —S(=O)R$_{23}$, —S(=O)$_2$R$_{23}$, —C(=O)R$_{23}$, —OC(=O)R$_{23}$, —CO$_2$R$_{21}$, —N($R_{21}$)($R_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted C$_1$-C$_6$alkyl, substituted or unsubstituted C$_1$-C$_8$heteroalkyl, or substituted or unsubstituted phenyl;

each $R_{21}$ and $R_{22}$ are each independently H, substituted or unsubstituted C$_1$-C$_6$alkyl, or substituted or unsubstituted C$_3$-C$_8$cycloalkyl;

$R_{23}$ is each independently substituted or unsubstituted C$_1$-C$_6$alkyl, or substituted or unsubstituted C$_3$-C$_8$cycloalkyl;

n is 0-4;

t is 0-2;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

each $L_3$ and J are each independently a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, substituted or unsubstituted C$_3$-C$_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl; or a pharmaceutically acceptable solvate, pharmaceutically acceptable salt, or pharmaceutically acceptable prodrug thereof.

In one embodiment is a compound of Formula (I) wherein $R_1$ is optionally substituted heteroalkyl, —(C=O)C$_1$-C$_6$ alkyl, —(C=O)OR$_4$, —(C=O)NR$_4$R$_4$, —(C=O)SR$_4$, -G-X, or

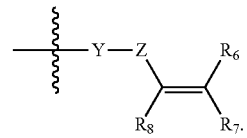

In another embodiment is a compound of Formula (I) wherein $R_1$ is -G-X. In some embodiments is a compound of Formula (I) wherein G is optionally substituted alkyl, optionally substituted cycloalkyl, optionally substituted heterocycloalkyl, optionally substituted heteroaryl, or optionally substituted aryl. In some embodiments is a compound of Formula (I) wherein G is optionally substituted alkyl. In some embodiments is a compound of Formula (I) wherein G is optionally substituted cycloalkyl. In some embodiments is a compound of Formula (I) wherein G is optionally substituted heterocycloalkyl. In some embodiments is a compound of Formula (I) wherein G is optionally substituted heteroaryl. In some embodiments is a compound of Formula (I) wherein G is optionally substituted aryl. In some embodiments is a compound of Formula (I) wherein X is optionally substituted cycloalkyl, optionally substituted heterocycloalkyl, optionally substituted aryl, optionally substituted heteroaryl, —OR$_4$, —SR$_4$, —NR$_4$R$_4$, or -$L_2$-Ar.

In another embodiment is a compound of Formula (I) wherein $R_1$ is

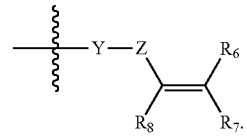

In a further embodiment is a compound of Formula (I) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (I) wherein $R_6$, $R_7$ and $R_8$ are H. In another embodiment is a compound of Formula (I) wherein $R_7$ and $R_8$ are H and $R_6$ is $L_3$-J-W. In a further embodiment, $R_6$ is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted C$_1$-C$_6$alkylC$_3$-C$_6$cycloalkyl, or C$_1$-C$_4$alkyl(C$_2$-C$_7$heterocycloalkyl). In yet a further embodiment is a compound of Formula (I) wherein $R_6$ is substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, or ((C$_1$-C$_6$alkyl)(C$_3$-C$_6$cycloalkyl)amino)C$_1$-C$_6$alkyl. In some embodiments, $R_6$ is substituted or unsubstituted C$_1$-C$_6$alkyl. In some embodiments, $R_6$ is substituted or unsubstituted C$_1$-C$_6$heteroalkyl. In some embodiments, $R_6$ is substituted or unsubstituted (C$_1$-C$_6$dialkylamino)C$_1$-C$_6$alkyl. In some embodiments, $R_6$ is substituted or unsubstituted ((C$_1$-C$_6$alkyl)(C$_3$-C$_6$cycloalkyl)amino)C$_1$-C$_6$alkyl. In some embodiments is a compound of Formula (I) wherein $R_6$ is halogen. In some embodiments is a compound of Formula (I) wherein $R_6$ is —CN.

In another embodiment is a compound of Formula (I) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (I) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (I) wherein $R_7$ is halogen. In some embodiments is a compound of Formula (I) wherein $R_7$ is —CN. In some embodiments is a compound of Formula (I) wherein $R_6$ is H, $R_8$ is halogen, and $R_7$ is $L_3$-J-W. In some embodiments is a compound of Formula (I) wherein $R_6$ is H, $R_8$ is —CN, and $R_7$ is $L_3$-J-W.

In another embodiment is a compound of Formula (I) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (I), wherein W is H. In another embodiment of the aforementioned embodiments is a compound of Formula (I), wherein W is —CN. In another embodiment of the aforementioned embodiments is a compound of Formula (I), wherein W is NR$_{25}$R$_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —CH$_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —CH$_3$ and $R_{26}$ is cyclopropyl. In some embodiments, $R_{25}$ is —CH$_3$ and $R_{26}$ is cyclobutyl.

In another embodiment is a compound of Formula (I) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (I) wherein $R_2$ is halogen, —CN, —NO$_2$, —OH, —OR$_{20}$, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -L$_2$-Ar. In some embodiments is a compound of Formula (I) wherein $R_2$ is halogen, substituted or unsubstituted alkyl, substituted or unsubstituted heteroalkyl, substituted or unsubstituted heterocycloalkyl, substituted or unsubstituted cycloalkyl, or -L$_2$-Ar. In some embodiments is a compound of Formula (I) wherein $R_2$ is halogen. In further embodiments is a compound of Formula (I) wherein $R_2$ is Cl. In further embodiments is a compound of Formula (I) wherein $R_2$ is F. In further embodiments is a compound of Formula (I) wherein $R_2$ is Br. In some embodiments is a compound of Formula (I) wherein $R_2$ is substituted or unsubstituted alkyl. In further embodiments is a compound of Formula (I) wherein $R_2$ is methyl.

In another embodiment is a compound of Formula (I) wherein $R_2$ is -L$_2$-Ar. In some embodiments is a compound of Formula (I) wherein $L_2$ is a bond, —CH$_2$—, —CH(OH)—, —C(O)—, —CH$_2$O—, —OCH$_2$—, —SCH$_2$, —CH$_2$S—, —N(R$_{21}$)—, —O—, —S—, —S(O)—, —S(O)$_2$—, —N(R$_{21}$)S(O)$_2$—, or —S(O)$_2$N(R$_{21}$)—. In some embodiments is a compound of Formula (I) wherein $L_2$ is —CH$_2$—, —CH$_2$O—, —OCH$_2$—, or —O—. In further embodiments is a compound of Formula (I) wherein $L_2$ is —O—. In another embodiment is a compound of Formula (I) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (I) wherein $R_3$ is each independently halogen, —NH$_2$, —N(CH$_3$)$_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In another embodiment of the aforementioned embodiments is a compound of Formula (I) wherein Y is aryl. In another embodiment of the aforementioned embodiments is a compound of Formula (I) wherein Y is heterocycloalkyl. In another embodiment of the aforementioned embodiments is a compound of Formula (I) wherein Y is cycloalkyl. In a further embodiment of the aforementioned embodiments is a compound of Formula (I) wherein t is 0. In a further embodiment of the aforementioned embodiments is a compound of Formula (I) wherein t is 1. In a further embodiment of the aforementioned embodiments is a compound of Formula (I) wherein t is 2.

In a further embodiment of the aforementioned embodiments is a compound of Formula (I), wherein n is 0. In some embodiments of the aforementioned embodiments is a compound of Formula (I), wherein n is 1. In some embodiments of the aforementioned embodiments is a compound of Formula (I), wherein n is 2. In some embodiments of the aforementioned embodiments is a compound of Formula (I), wherein n is 3. In some embodiments of the aforementioned embodiments is a compound of Formula (I), wherein n is 4.

In a further embodiment are compounds having the structure of Formula (Ia):

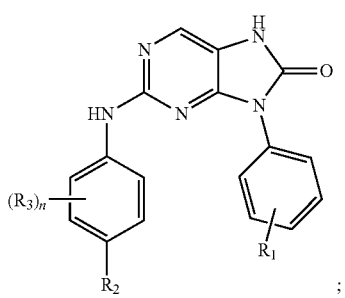

Formula (Ia)

wherein:
$R_1$ is halogen, —CN, —NO$_2$, —OH, —OCF$_3$, —OCH$_2$F, —OCF$_2$H, —CF$_3$, —SR$_{21}$, —N(R$_{21}$)S(═O)$_2$R$_{23}$, —S(═O)$_2$N(R$_{21}$)(R$_{22}$), —S(═O)R$_{23}$, —S(═O)$_2$R$_{23}$, —C(═O)R$_{23}$, —OC(═O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

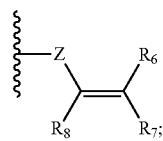

$R_2$ is halogen, —CN, —NO$_2$, —OH, —OR$_{20}$, —OCF$_3$, —OCH$_2$F, —OCF$_2$H, —CF$_3$, —SR$_{21}$, —N(R$_{21}$)S(═O)$_2$R$_{23}$, —S(═O)$_2$N(R$_{21}$)(R$_{22}$), —S(═O)R$_{23}$, —S(═O)$_2$R$_{23}$, —C(═O)R$_{23}$, —OC(═O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -L$_2$-Ar;

L$_2$ is a bond, —CH$_2$—, —CH(OH)—, —C(O)—, —CH$_2$O—, —OCH$_2$—, —SCH$_2$—, —CH$_2$S—, —N(R$_{21}$)—, —O—, —S—, —S(O)—, —S(O)$_2$—, —N(R$_{21}$)S(O)$_2$—, or —S(O)$_2$N(R$_{21}$)—;

Ar is a substituted or unsubstituted cycloalkyl, substituted or unsubstituted heterocycloalkyl, substituted or unsubstituted aryl, or a substituted or unsubstituted heteroaryl;

Z is C(═O), OC(═O), N(R$_{21}$)C(═O), C(═S), S(═O)$_p$, OS(═O)$_x$, or N(R$_{21}$)S(═O)$_p$, where p is 1 or 2;

each $R_3$ is each independently halogen, —CN, —NO$_2$, —OH, —OCF$_3$, —OCH$_2$F, —OCF$_2$H, —CF$_3$, —SR$_{21}$, —N(R$_{21}$)S(═O)$_2$R$_{23}$, —S(═O)$_2$N(R$_{21}$)(R$_{22}$), —S(═O)R$_{23}$, —S(═O)$_2$R$_{23}$, —C(═O)R$_{23}$, —OC(═O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted C$_1$-C$_6$alkyl, substituted or unsubstituted C$_1$-C$_8$heteroalkyl, or substituted or unsubstituted phenyl;

each $R_{21}$ and $R_{22}$ are each independently H, substituted or unsubstituted C$_1$-C$_6$alkyl, or substituted or unsubstituted C$_3$-C$_8$cycloalkyl;

$R_{23}$ is each independently substituted or unsubstituted C$_1$-C$_6$alkyl, or substituted or unsubstituted C$_3$-C$_8$cycloalkyl;

n is 0-4;

$R_6$ is H, halogen, —CN, or L$_3$-J-W;

$R_7$ and $R_8$ are independently H, halogen, —CN, or L$_3$-J-W; or $R_7$ and $R_8$ taken together form a bond;

L$_3$ and J are each independently a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, substituted or unsubstituted C$_3$-C$_{12}$ heteroarylene, —C(═O)—, —O—, or —S—;

each W is H, —CN, or —NR$_{25}$R$_{26}$;

$R_{25}$ and $R_{26}$ are each independently H, substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl; or a pharmaceutically acceptable solvate, pharmaceutically acceptable salt, or pharmaceutically acceptable prodrug thereof.

In one embodiment is a compound of Formula (Ia) wherein $R_1$ is halogen, —CN, —NO$_2$, —OH, —OCF$_3$, —OCH$_2$F, —OCF$_2$H, —CF$_3$, —SR$_{21}$, —N(R$_{21}$)S(═O)$_2$R$_{23}$, —S(═O)$_2$N(R$_{21}$)(R$_{22}$), —S(═O)R$_{23}$, —S(═O)$_2$R$_{23}$, —C(═O)R$_{23}$, —OC(═O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

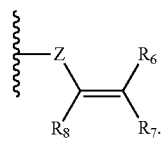

In another embodiment is a compound of Formula (Ia) wherein $R_1$ is halogen, substituted or unsubstituted alkyl, substituted or unsubstituted alkoxy, or substituted or unsubstituted heteroalkyl. In some embodiments is a compound of Formula (Ia) wherein $R_1$ is halogen. In further embodiments is a compound of Formula (Ia) wherein $R_1$ is Cl. In further embodiments is a compound of Formula (Ia) wherein $R_1$ is F. In further embodiments is a compound of Formula (Ia) wherein $R_1$ is Br. In some embodiments is a compound of Formula (Ia) wherein $R_1$ is substituted or unsubstituted alkyl. In further embodiments is a compound of Formula (Ia) wherein $R_1$ is methyl. In some embodiments is a compound of Formula (Ia) wherein $R_1$ is substituted or unsubstituted alkoxy. In some embodiments is a compound of Formula (Ia) wherein $R_1$ is substituted or unsubstituted heteroalkyl.

In another embodiment is a compound of Formula (Ia) wherein $R_1$ is

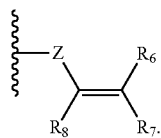

In a further embodiment is a compound of Formula (Ia) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (Ia) wherein $R_6$, $R_7$ and $R_8$ are H. In another embodiment is a compound of Formula (Ia) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Ia) wherein $R_6$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted $(C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (Ia) wherein $R_6$ is halogen. In some embodiments is a compound of Formula (Ia) wherein $R_6$ is —CN.

In another embodiment is a compound of Formula (Ia) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Ia) wherein $R_7$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted $(C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (Ia) wherein $R_7$ is halogen. In some embodiments is a compound of Formula (Ia) wherein $R_7$ is —CN. In some embodiments is a compound of Formula (Ia) wherein $R_6$ is H, $R_8$ is halogen, and $R_7$ is $L_3$-J-W. In some embodiments is a compound of Formula (Ia) wherein $R_6$ is H, $R_8$ is —CN, and $R_7$ is $L_3$-J-W.

In another embodiment is a compound of Formula (Ia) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (Ia), wherein W is H. In another embodiment of the aforementioned embodiments is a compound of Formula (Ia), wherein W is —CN. In another embodiment of the aforementioned embodiments is a compound of Formula (Ia), wherein W is NR$_{25}$R$_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —CH$_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —CH$_3$ and $R_{26}$ is cyclopropyl. In some embodiments, $R_{25}$ is —CH$_3$ and $R_{26}$ is cyclobutyl.

In another embodiment is a compound of Formula (Ia) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (Ia) wherein $R_2$ is halogen, —CN, —$NO_2$, —OH, —$OR_{20}$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Ia) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Ia) wherein $R_2$ is halogen. In further embodiments is a compound of Formula (Ia) wherein $R_2$ is Cl. In further embodiments is a compound of Formula (Ia) wherein $R_2$ is F. In further embodiments is a compound of Formula (Ia) wherein $R_2$ is Br. In some embodiments is a compound of Formula (Ia) wherein $R_2$ is substituted or unsubstituted alkyl. In further embodiments is a compound of Formula (Ia) wherein $R_2$ is methyl.

In another embodiment is a compound of Formula (Ia) wherein $R_2$ is -$L_2$-Ar. In some embodiments is a compound of Formula (Ia) wherein $L_2$ is a bond, —$CH_2$—, —CH(OH)—, —C(O)—, —$CH_2O$—, —$OCH_2$—, —$SCH_2$—, —$CH_2S$—, —$N(R_{21})$—, —O—, —S—, —S(O)—, —$S(O)_2$—, —$N(R_{21})S(O)_2$—, or —$S(O)_2N(R_{21})$—. In some embodiments is a compound of Formula (Ia) wherein $L_2$ is —$CH_2$—, —$CH_2O$—, —$OCH_2$—, or —O—. In further embodiments is a compound of Formula (Ia) wherein $L_2$ is —O—. In another embodiment is a compound of Formula (Ia) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (Ia) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (Ia), wherein n is 0. In some embodiments of the aforementioned embodiments is a compound of Formula (Ia), wherein n is 1. In some embodiments of the aforementioned embodiments is a compound of Formula (Ia), wherein n is 2. In some embodiments of the aforementioned embodiments is a compound of Formula (Ia), wherein n is 3. In some embodiments of the aforementioned embodiments is a compound of Formula (Ia), wherein n is 4.

In a further embodiment are compounds having the structure of Formula (Ib):

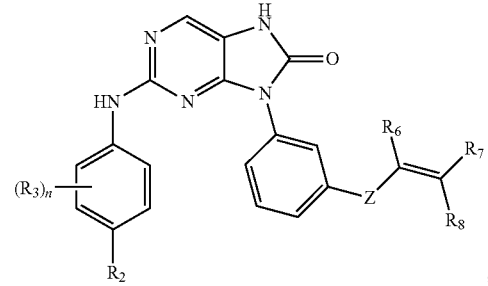

Formula (Ib)

wherein:
$R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar;

$L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—;

Ar is a substituted or unsubstituted cycloalkyl, substituted or unsubstituted heterocycloalkyl, substituted or unsubstituted aryl, or a substituted or unsubstituted heteroaryl;

Z is C(=O), OC(=O), $N(R_{21})C(=O)$, C(=S), $S(=O)_p$, $OS(=O)_x$, or $N(R_{21})S(=O)_p$, where p is 1 or 2;

each $R_3$ is each independently halogen, —CN, —$NO_2$, —OH, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

$L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —$NR_{25}R_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (Ib) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (Ib) wherein $R_6$, $R_7$ and $R_8$ are H. In another embodiment is a compound of Formula (Ib) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Ib) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (Ib) wherein $R_6$ is halogen. In some embodiments is a compound of Formula (Ib) wherein $R_6$ is —CN.

In another embodiment is a compound of Formula (Ib) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Ib) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (Ib) wherein $R_7$ is halogen. In some embodiments is a compound of Formula (Ib) wherein $R_7$ is —CN. In some embodiments is a compound of Formula (Ib) wherein $R_6$ is H, $R_8$ is halogen, and $R_7$ is $L_3$-J-W. In some embodiments is a compound of Formula (Ib) wherein $R_6$ is H, $R_8$ is —CN, and $R_7$ is $L_3$-J-W.

In another embodiment is a compound of Formula (Ib) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (Ib), wherein W is H. In another embodiment of the aforementioned embodiments is a compound of Formula (Ib), wherein W is —CN. In another embodiment of the aforementioned embodiments is a compound of Formula (Ib), wherein W is NR$_{25}$R$_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —CH$_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —CH$_3$ and $R_{26}$ is cyclopropyl. In some embodiments, $R_{25}$ is —CH$_3$ and $R_{26}$ is cyclobutyl.

In another embodiment is a compound of Formula (Ib) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (Ib) wherein $R_2$ is halogen, —CN, —NO$_2$, —OH, —OR$_{20}$, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -L$_2$-Ar. In some embodiments is a compound of Formula (Ib) wherein $R_2$ is halogen, substituted or unsubstituted alkyl, substituted or unsubstituted heteroalkyl, substituted or unsubstituted heterocycloalkyl, substituted or unsubstituted cycloalkyl, or -L$_2$-Ar. In some embodiments is a compound of Formula (Ib) wherein $R_2$ is halogen. In further embodiment is a compound of Formula (Ib) wherein $R_2$ is Cl. In some embodiment is a compound of Formula (Ib) wherein $R_2$ is F. In further embodiments is a compound of Formula (Ib) wherein $R_2$ is Br. In some embodiments is a compound of Formula (Ib) wherein $R_2$ is substituted or unsubstituted alkyl. In further embodiments is a compound of Formula (Ib) wherein $R_2$ is methyl.

In another embodiment is a compound of Formula (Ib) wherein $R_2$ is -$L_2$-Ar. In some embodiments is a compound of Formula (Ib) wherein $L_2$ is a bond, —$CH_2$—, —CH(OH)—, —C(O)—, —$CH_2$O—, —OCH$_2$—, —SCH$_2$—, —$CH_2$S—, —N($R_{21}$)—, —O—, —S—, —S(O)—, —S(O)$_2$—, —N($R_{21}$)S(O)$_2$—, or —S(O)$_2$N($R_{21}$)—. In some embodiments is a compound of Formula (Ib) wherein $L_2$ is —$CH_2$—, —$CH_2$O—, —OCH$_2$—, or —O—. In further embodiments is a compound of Formula (Ib) wherein $L_2$ is —O—. In another embodiment is a compound of Formula (Ib) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (Ib) wherein $R_3$ is each independently halogen, —NH$_2$, —N(CH$_3$)$_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (Ib), wherein n is 0. In some embodiments of the aforementioned embodiments is a compound of Formula (Ib), wherein n is 1. In some embodiments of the aforementioned embodiments is a compound of Formula (Ib), wherein n is 2. In some embodiments of the aforementioned embodiments is a compound of Formula (Ib), wherein n is 3. In some embodiments of the aforementioned embodiments is a compound of Formula (Ib), wherein n is 4.

In a further embodiment are compounds having the structure of Formula (Ic):

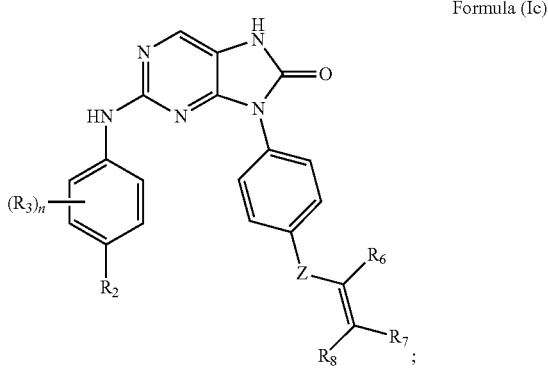

Formula (Ic)

wherein:
$R_2$ is halogen, —CN, —NO$_2$, —OH, —OR$_{20}$, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -L$_2$-Ar;

$L_2$ is a bond, —CH$_2$—, —CH(OH)—, —C(O)—, —CH$_2$O—, —OCH$_2$—, —SCH$_2$—, —CH$_2$S—, —N(R$_{21}$)—, —O—, —S—, —S(O)—, —S(O)$_2$—, —N(R$_{21}$)S(O)$_2$—, or —S(O)$_2$N(R$_{21}$)—;

Ar is a substituted or unsubstituted cycloalkyl, substituted or unsubstituted heterocycloalkyl, substituted or unsubstituted aryl, or a substituted or unsubstituted heteroaryl;

Z is C(=O), OC(=O), N(R$_{21}$)C(=O), C(=S), S(=O)$_p$, OS(=O)$_x$, or N(R$_{21}$)S(=O)$_p$, where p is 1 or 2;

each $R_3$ is each independently halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted C$_1$-C$_6$alkyl, substituted or unsubstituted C$_1$-C$_8$heteroalkyl, or substituted or unsubstituted phenyl;

each $R_{21}$ and $R_{22}$ are each independently H, substituted or unsubstituted C$_1$-C$_6$alkyl, or substituted or unsubstituted C$_3$-C$_8$cycloalkyl;

$R_{23}$ is each independently substituted or unsubstituted C$_1$-C$_6$alkyl, or substituted or unsubstituted C$_3$-C$_8$cycloalkyl;

n is 0-4;

$R_6$ is H, halogen, —CN, or L$_3$-J-W;

$R_7$ and $R_8$ are independently H, halogen, —CN, or L$_3$-J-W; or $R_7$ and $R_8$ taken together form a bond;

$L_3$ and J are each independently a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, substituted or unsubstituted C$_3$-C$_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl; or a pharmaceutically acceptable solvate, pharmaceutically acceptable salt, or pharmaceutically acceptable prodrug thereof.

In one embodiment is a compound of Formula (Ic) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (Ic) wherein $R_6$, $R_7$ and $R_8$ are H. In another embodiment is a compound of Formula (Ic) wherein $R_7$ and $R_8$ are H and $R_6$ is L$_3$-J-W. In a further embodiment, $R_6$ is H, substituted or unsubstituted C$_1$-C$_6$alkyl, substituted or unsubstituted C$_1$-C$_6$heteroalkyl, (C$_1$-C$_6$dialkylamino)C$_1$-C$_6$alkyl, ((C$_1$-C$_6$alkyl)(C$_3$-C$_6$cycloalkyl)amino)C$_1$-C$_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In yet a further embodiment is a compound of Formula (Ic) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (Ic) wherein $R_6$ is halogen. In some embodiments is a compound of Formula (Ic) wherein $R_6$ is —CN.

In another embodiment is a compound of Formula (Ic) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Ic) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (Ic) wherein $R_7$ is halogen. In some embodiments is a compound of Formula (Ic) wherein $R_7$ is —CN. In some embodiments is a compound of Formula (Ic) wherein $R_6$ is H, $R_8$ is halogen, and $R_7$ is $L_3$-J-W. In some embodiments is a compound of Formula (Ic) wherein $R_6$ is H, $R_8$ is —CN, and $R_7$ is $L_3$-J-W.

In another embodiment is a compound of Formula (Ic) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —$CH_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —$CH_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (Ic), wherein W is H. In another embodiment of the aforementioned embodiments is a compound of Formula (Ic), wherein W is —CN. In another embodiment of the aforementioned embodiments is a compound of Formula (Ic), wherein W is $NR_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (Ic) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (Ic) wherein $R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Ic) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Ic) wherein $R_2$ is halogen. In further embodiments is a compound of Formula (Ic) wherein $R_2$ is Cl. In further embodiments is a compound of Formula (Ic) wherein $R_2$ is F. In further embodiments is a compound of Formula (Ic) wherein $R_2$ is Br. In some embodiments is a compound of Formula (Ic) wherein $R_2$ is substituted or unsubstituted alkyl. In further embodiments is a compound of Formula (Ic) wherein $R_2$ is methyl.

In another embodiment is a compound of Formula (Ic) wherein $R_2$ is -$L_2$-Ar. In some embodiments is a compound of Formula (Ic) wherein $L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—. In some embodiments is a compound of Formula (Ic) wherein $L_2$ is —$CH_2$—, —$CH_2O$—, —$OCH_2$—, or —O—. In further embodiments is a compound of Formula (Ic) wherein $L_2$ is —O—. In another embodiment is a compound of Formula (Ic) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (Ic) wherein $R_3$ is each independently halogen, $-NH_2$, $-N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (Ic), wherein n is 0. In some embodiments of the aforementioned embodiments is a compound of Formula (Ic), wherein n is 1. In some embodiments of the aforementioned embodiments is a compound of Formula (Ic), wherein n is 2. In some embodiments of the aforementioned embodiments is a compound of Formula (Ic), wherein n is 3. In some embodiments of the aforementioned embodiments is a compound of Formula (Ic), wherein n is 4.

In another embodiment are compounds having the structure of Formula (Id):

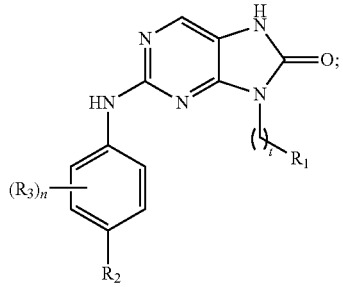

Formula (Id)

wherein:
$R_1$ is

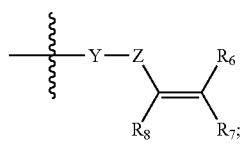

Y is an optionally substituted heterocycloalkyl;
Z is $C(=O)$, $OC(=O)$, $N(R_{21})C(=O)$, $C(=S)$, $S(=O)_p$, $OS(=O)_p$, or $N(R_{21})S(=O)_p$, where p is 1 or 2;
$R_2$ is hydrogen, halogen, $-CN$, $-NO_2$, $-OH$, $-OR_{20}$, $-OCF_3$, $-OCH_2F$, $-OCF_2H$, $-CF_3$, $-SR_{21}$, $-N(R_{21})S(=O)_2R_{23}$, $-S(=O)_2N(R_{21})(R_{22})$, $-S(=O)R_{23}$, $-S(=O)_2R_{23}$, $-C(=O)R_{23}$, $-OC(=O)R_{23}$, $-CO_2R_{21}$, $-N(R_{21})(R_{22})$, substituted or unsubstituted alkyl, substituted or unsubstituted heteroalkyl, substituted or unsubstituted heterocycloalkyl, substituted or unsubstituted cycloalkyl, or $-L_2$-Ar;
$L_2$ is a bond, $-CH_2-$, $-CH(OH)-$, $-C(O)-$, $-CH_2O-$, $-OCH_2-$, $-SCH_2$, $-CH_2S-$, $-N(R_{21})-$, $-O-$, $-S-$, $-S(O)-$, $-S(O)_2-$, $-N(R_{21})S(O)_2-$, or $-S(O)_2N(R_{21})-$;

Ar is a substituted or unsubstituted cycloalkyl, substituted or unsubstituted heterocycloalkyl, substituted or unsubstituted aryl, or a substituted or unsubstituted heteroaryl;

each $R_3$ is each independently halogen, $-CN$, $-NO_2$, $-OH$, $-OCF_3$, $-OCH_2F$, $-OCF_2H$, $-CF_3$, $-SR_{21}$, $-N(R_{21})S(=O)_2R_{23}$, $-S(=O)_2N(R_{21})(R_{22})$, $-S(=O)R_{23}$, $-S(=O)_2R_{23}$, $-C(=O)R_{23}$, $-OC(=O)R_{23}$, $-CO_2R_{21}$, $-N(R_{21})(R_{22})$, substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;
t is 0;
$R_6$ is H, halogen, $-CN$, or $L_3$-J-W;
$R_7$ and $R_8$ are independently H, halogen, $-CN$, or $L_3$-J-W; or $R_7$ and $R_8$ taken together form a bond;

each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, $-C(=O)-$, $-O-$, or $-S-$;

each W is H, $-CN$, or $-NR_{25}R_{26}$;
$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (Id) wherein Z is $C(=O)$, $NHC(=O)$, $N(CH_3)C(=O)$, or $S(=O)_2$. In some embodiments, Z is $C(=O)$. In some embodiments, Z is $NHC(=O)$. In some embodiments, Z is $N(CH_3)C(=O)$. In some embodiments, Z is $S(=O)_2$.

In some embodiments is a compound of Formula (Id) wherein Y is piperidine. In some embodiments is a compound of Formula (Id) wherein Y is pyrrolidine. In some embodiments is a compound of Formula (Id) wherein Y is azetidine.

In another embodiment is a compound of Formula (Id) wherein $R_6$, $R_7$ and $R_8$ are H. In another embodiment is a compound of Formula (Id) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, $((C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Id) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (Id) wherein $R_6$ is halogen. In some embodiments is a compound of Formula (Id) wherein $R_6$ is —CN.

In another embodiment is a compound of Formula (Id) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (Id) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (Id) wherein $R_7$ is halogen. In some embodiments is a compound of Formula (Id) wherein $R_7$ is —CN. In some embodiments is a compound of Formula (Id) wherein $R_6$ is H, $R_8$ is halogen, and $R_7$ is $L_3$-J-W. In some embodiments is a compound of Formula (Id) wherein $R_6$ is H, $R_8$ is —CN, and $R_7$ is $L_3$-J-W.

In another embodiment is a compound of Formula (Id) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —$CH_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —$CH_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (Id), wherein W is H. In another embodiment of the aforementioned embodiments is a compound of Formula (Id), wherein W is —CN. In another embodiment of the aforementioned embodiments is a compound of Formula (Id), wherein W is $NR_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (Id) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (Id) wherein $R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Id) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (Id) wherein $R_2$ is halogen. In further embodiments is a compound of Formula (Id) wherein $R_2$ is Cl. In further embodiments is a compound of Formula (Id) wherein $R_2$ is F. In further embodiments is a compound of Formula (Id) wherein $R_2$ is Br. In some embodiments is a compound of Formula (Id) wherein $R_2$ is substituted or unsubstituted alkyl. In further embodiments is a compound of Formula (Id) wherein $R_2$ is methyl.

In another embodiment is a compound of Formula (Id) wherein $R_2$ is -$L_2$-Ar. In some embodiments is a compound of Formula (Id) wherein $L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—. In some embodiments is a compound of Formula (Id) wherein $L_2$ is —$CH_2$—, —$CH_2O$—, —$OCH_2$—, or —O—. In further embodiments is a compound of Formula (Id) wherein $L_2$ is —O—. In another embodiment is a compound of Formula (Id) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (Id) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (Id), wherein n is 0. In some embodiments of the aforementioned embodiments is a compound of Formula (Id), wherein n is 1. In some embodiments of the aforementioned embodiments is a compound of Formula (Id), wherein n is 2. In some embodiments of the aforementioned embodiments is a compound of Formula (Id), wherein n is 3. In some embodiments of the aforementioned embodiments is a compound of Formula (Id), wherein n is 4.

In another embodiment are compounds having the structure of Formula (II):

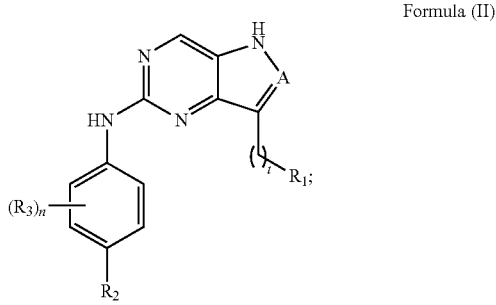

Formula (II)

wherein:

A is =C($R_9$)—, or =N—;

$R_1$ is substituted or unsubstituted alkoxy, substituted or unsubstituted heteroalkyl, substituted or unsubstituted heterocycloalkyl, substituted or unsubstituted cycloalkyl, substituted or unsubstituted heteroaryl, substituted aryl, —(C=O)$C_1$-$C_6$ alkyl, —(C=O)$OR_4$, —(C=O)$NR_4R_4$, —(C=O)$SR_4$, -G-X, —Y-$L_2$-Ar, or

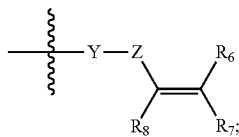

G is optionally substituted alkyl;

X is optionally substituted cycloalkyl, optionally substituted heterocycloalkyl, optionally substituted aryl, optionally substituted heteroaryl, —$OR_4$, —$SR_4$, —$NR_4R_4$, or -$L_2$-Ar;

each $R_4$ is each independently H, $C_1$-$C_6$ alkyl, $C_1$-$C_6$ heteroalkyl, $C_3$-$C_6$ cycloalkyl, or $C_2$-$C_6$ heterocycloalkyl;

Y is an optionally substituted group selected from among alkyl, heteroalkyl, cycloalkyl, heterocycloalkyl, aryl, and heteroaryl;

$R_2$ is hydrogen, halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar;

$L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—;

Ar is a substituted or unsubstituted cycloalkyl, substituted or unsubstituted heterocycloalkyl, substituted or unsubstituted aryl, or a substituted or unsubstituted heteroaryl;

Z is C(=O), OC(=O), N($R_{21}$)C(=O), C(=S), S(=O)$_p$, OS(=O)$_x$, or N($R_{21}$)S(=O)$_p$, where p is 1 or 2;

each $R_3$ is each independently halogen, —CN, —$NO_2$, —OH, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;

$R_9$ is H, halogen, —CN, —OH, —$NH_2$, —SH, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —$NR_{25}R_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (II) wherein A is =C(H)— or =N—. In some embodiments is a compound of Formula (II) wherein A is =N—. In some embodiments is a compound of Formula (II) wherein A is =C($R_9$)—. In some embodiments is a compound of Formula (II) wherein $R_9$ is H, halogen, substituted or unsubstituted $C_1$-$C_6$alkyl, substituted or unsubstituted $C_1$-$C_4$alkoxy, or substituted or unsubstituted $C_1$-$C_6$heteroalkyl. In some embodiments is a compound of Formula (II) wherein $R_9$ is H. In some embodiments is a compound of Formula (II) wherein $R_9$ is halogen. In some embodiments is a compound of Formula (II) wherein $R_9$ is substituted or unsubstituted $C_1$-$C_6$alkyl. In some embodiments is a compound of Formula (II) wherein $R_9$ is substituted or unsubstituted $C_1$-$C_4$alkoxy. In some embodiments is a compound of Formula (II) wherein $R_9$ is substituted or unsubstituted $C_1$-$C_6$heteroalkyl.

In another embodiment is a compound of Formula (II) wherein $R_1$ is substituted or unsubstituted alkoxy, substituted or unsubstituted heteroalkyl, substituted or unsubstituted heterocycloalkyl, substituted or unsubstituted cycloalkyl, substituted or unsubstituted heteroaryl, substituted aryl, —(C=O)$C_1$-$C_6$ alkyl, —(C=O)O$R_4$, —(C=O)N$R_4R_4$, —(C=O)S$R_4$, -G-X, —Y-$L_2$-Ar, or

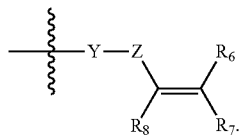

In another embodiment is a compound of Formula (II) wherein $R_1$ is -G-X. In some embodiments is a compound of Formula (II) wherein G is optionally substituted alkyl, and X is optionally substituted cycloalkyl, optionally substituted heterocycloalkyl, optionally substituted aryl, optionally substituted heteroaryl, —O$R_4$, —S$R_4$, —N$R_4R_4$, or -$L_2$-Ar.

In another embodiment is a compound of Formula (II) wherein $R_1$ is

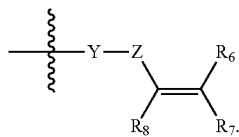

In a further embodiment is a compound of Formula (II) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (II) wherein $R_6$, $R_7$ and $R_8$ are H. In another embodiment is a compound of Formula (II) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (II) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (II) wherein $R_6$ is halogen. In some embodiments is a compound of Formula (II) wherein $R_6$ is —CN.

In another embodiment is a compound of Formula (II) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (II) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (II) wherein $R_7$ is halogen. In some embodiments is a compound of Formula (II) wherein $R_7$ is —CN. In some embodiments is a compound of Formula (II) wherein $R_6$ is H, $R_8$ is halogen, and $R_7$ is $L_3$-J-W. In some embodiments is a compound of Formula (II) wherein $R_6$ is H, $R_8$ is —CN, and $R_7$ is $L_3$-J-W.

In another embodiment is a compound of Formula (II) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (II), wherein W is H. In another embodiment of the aforementioned embodiments is a compound of Formula (II), wherein W is —CN. In another embodiment of the aforementioned embodiments is a compound of Formula (II), wherein W is N$R_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (II) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is $(C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (II) wherein $R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (II) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (II) wherein $R_2$ is halogen. In further embodiments is a compound of Formula (II) wherein $R_2$ is Cl. In further embodiments is a compound of Formula (II) wherein $R_2$ is F. In further embodiments is a compound of Formula (II) wherein $R_2$ is Br. In some embodiments is a compound of Formula (II) wherein $R_2$ is substituted or unsubstituted alkyl. In further embodiments is a compound of Formula (II) wherein $R_2$ is methyl.

In another embodiment is a compound of Formula (II) wherein $R_2$ is -$L_2$-Ar. In some embodiments is a compound of Formula (II) wherein $L_2$ is a bond, —$CH_2$—, —CH(OH)—, —C(O)—, —$CH_2O$—, —$OCH_2$—, —$SCH_2$—, —$CH_2S$—, —$N(R_{21})$—, —O—, —S—, —S(O)—, —$S(O)_2$—, —$N(R_{21})S(O)_2$—, or —$S(O)_2N(R_{21})$—. In some embodiments is a compound of Formula (II) wherein $L_2$ is —$CH_2$—, —$CH_2O$—, —$OCH_2$—, or —O—. In further embodiments is a compound of Formula (II) wherein $L_2$ is —O—. In another embodiment is a compound of Formula (II) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (II) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In another embodiment of the aforementioned embodiments is a compound of Formula (II) wherein Y is aryl. In another embodiment of the aforementioned embodiments is a compound of Formula (II) wherein Y is heterocycloalkyl. In another embodiment of the aforementioned embodiments is a compound of Formula (II) wherein Y is cycloalkyl. In a further embodiment of the aforementioned embodiments is a compound of Formula (II) wherein t is 0. In a further embodiment of the aforementioned embodiments is a compound of Formula (II) wherein t is 1. In a further embodiment of the aforementioned embodiments is a compound of Formula (II) wherein t is 2.

In a further embodiment of the aforementioned embodiments is a compound of Formula (II), wherein n is 0. In some embodiments of the aforementioned embodiments is a compound of Formula (II), wherein n is 1. In some embodiments of the aforementioned embodiments is a compound of Formula (II), wherein n is 2. In some embodiments of the aforementioned embodiments is a compound of Formula (II), wherein n is 3. In some embodiments of the aforementioned embodiments is a compound of Formula (II), wherein n is 4.

In another embodiment are compounds having the structure of Formula (IIa):

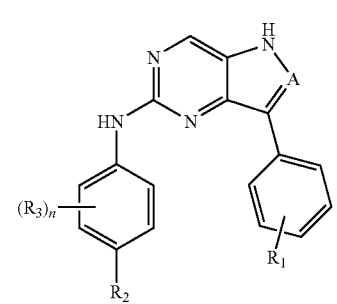

Formula (IIa)

wherein:
A is =C($R_9$)—, or =N—;
$R_1$ is halogen, —CN, —$NO_2$, —OH, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted alkoxy, substituted or unsubstituted heteroalkyl, substituted or unsubstituted heterocycloalkyl, substituted or unsubstituted cycloalkyl, or

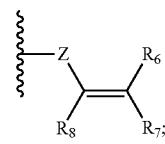

$R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S$ (=O)₂R₂₃, —S(=O)₂N(R₂₁)(R₂₂), —S(=O)R₂₃, —S(=O)₂R₂₃, —C(=O)R₂₃, —OC(=O)R₂₃, —CO₂R₂₁, —N(R₂₁)(R₂₂), substituted or unsubstituted alkyl, substituted or unsubstituted heteroalkyl, substituted or unsubstituted heterocycloalkyl, substituted or unsubstituted cycloalkyl, or -L₂-Ar;

L₂ is a bond, —CH₂—, —CH(OH)—, —C(O)—, —CH₂O—, —OCH₂—, —SCH₂—, —CH₂S—, —N(R₂₁)—, —O—, —S—, —S(O)—, —S(O)₂—, —N(R₂₁)S(O)₂—, or —S(O)₂N(R₂₁)—;

Ar is a substituted or unsubstituted cycloalkyl, substituted or unsubstituted heterocycloalkyl, substituted or unsubstituted aryl, or a substituted or unsubstituted heteroaryl;

Z is C(=O), OC(=O), N(R₂₁)C(=O), C(=S), S(=O)ₚ, OS(=O)ₓ, or N(R₂₁)S(=O)ₚ, where p is 1 or 2;

each R₃ is each independently halogen, —CN, —NO₂, —OH, —OCF₃, —OCH₂F, —OCF₂H, —CF₃, —SR₂₁, —N(R₂₁)S(=O)₂R₂₃, —S(=O)₂N(R₂₁)(R₂₂), —S(=O)R₂₃, —S(=O)₂R₂₃, —C(=O)R₂₃, —OC(=O)R₂₃, —CO₂R₂₁, —N(R₂₁)(R₂₂), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

R₂₀ is substituted or unsubstituted C₁-C₆alkyl, substituted or unsubstituted C₁-C₈heteroalkyl, or substituted or unsubstituted phenyl;

each R₂₁ and R₂₂ are each independently H, substituted or unsubstituted C₁-C₆alkyl, or substituted or unsubstituted C₃-C₈cycloalkyl;

R₂₃ is each independently substituted or unsubstituted C₁-C₆alkyl, or substituted or unsubstituted C₃-C₈cycloalkyl;

n is 0-4;

R₉ is H, halogen, —CN, —OH, —NH₂, —SH, substituted or unsubstituted C₁-C₆alkyl, substituted or unsubstituted C₁-C₄alkoxy, substituted or unsubstituted C₁-C₆heteroalkyl, substituted or unsubstituted phenyl, substituted or unsubstituted heteroaryl, or substituted or unsubstituted C₃-C₈cycloalkyl;

R₆ is H, halogen, —CN, or L₃-J-W;

R₇ and R₈ are independently H, halogen, —CN, or L₃-J-W; or R₇ and R₈ taken together form a bond;

L₃ and J are each independently a bond, substituted or unsubstituted C₁-C₆ alkylene, substituted or unsubstituted C₃-C₆ cycloalkylene, substituted or unsubstituted C₁-C₆ heteroalkylene, substituted or unsubstituted C₂-C₇ heterocycloalkylene, substituted or unsubstituted C₆-C₁₂ arylene, substituted or unsubstituted C₃-C₁₂ heteroarylene, —C(=O)—, —O—, or —S—;

each W is H, —CN, or —NR₂₅R₂₆;

R₂₅ and R₂₆ are each independently H, substituted or unsubstituted C₁-C₆ alkyl, substituted or unsubstituted C₃-C₆ cycloalkyl, substituted or unsubstituted C₁-C₆ heteroalkyl, substituted or unsubstituted C₂-C₇ heterocycloalkyl, substituted or unsubstituted C₆-C₁₂ aryl, or substituted or unsubstituted C₃-C₁₂ heteroaryl; or a pharmaceutically acceptable solvate, pharmaceutically acceptable salt, or pharmaceutically acceptable prodrug thereof.

In one embodiment is a compound of Formula (IIa) wherein A is =C(H)— or =N—. In some embodiments is a compound of Formula (IIa) wherein A is =N—. In some embodiments is a compound of Formula (IIa) wherein A is =C(R₉)—. In some embodiments is a compound of Formula (IIa) wherein R₉ is H, halogen, substituted or unsubstituted C₁-C₆alkyl, substituted or unsubstituted C₁-C₄alkoxy, or substituted or unsubstituted C₁-C₆heteroalkyl. In some embodiments is a compound of Formula (IIa) wherein R₉ is H. In some embodiments is a compound of Formula (IIa) wherein R₉ is halogen. In some embodiments is a compound of Formula (IIa) wherein R₉ is substituted or unsubstituted C₁-C₆alkyl. In some embodiments is a compound of Formula (IIa) wherein R₉ is substituted or unsubstituted C₁-C₄alkoxy. In some embodiments is a compound of Formula (IIa) wherein R₉ is substituted or unsubstituted C₁-C₆heteroalkyl.

In another embodiment is a compound of Formula (IIa) wherein R₁ is halogen, —CN, —NO₂, —OH, —OCF₃, —OCH₂F, —OCF₂H, —CF₃, —SR₂₁, —N(R₂₁)S(=O)₂R₂₃, —S(=O)₂N(R₂₁)(R₂₂), —S(=O)R₂₃, —S(=O)₂R₂₃, —C(=O)R₂₃, —OC(=O)R₂₃, —CO₂R₂₁, —N(R₂₁)(R₂₂), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

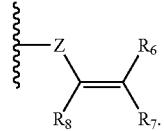

In another embodiment is a compound of Formula (IIa) wherein R₁ is halogen, substituted or unsubstituted alkyl, substituted or unsubstituted alkoxy, or substituted or unsubstituted heteroalkyl. In some embodiments is a compound of Formula (IIa) wherein R₁ is halogen. In further embodiments is a compound of Formula (IIa) wherein R₁ is Cl. In further embodiments is a compound of Formula (IIa) wherein R₁ is F. In further embodiments is a compound of Formula (IIa) wherein R₁ is Br. In some embodiments is a compound of Formula (IIa) wherein R₁ is substituted or unsubstituted alkyl. In further embodiments is a compound of Formula (IIa) wherein R₁ is methyl. In some embodiments is a compound of Formula (IIa) wherein R₁ is substituted or unsubstituted alkoxy. In some embodiments is a compound of Formula (IIa) wherein R₁ is substituted or unsubstituted heteroalkyl.

In another embodiment is a compound of Formula (IIa) wherein R₁ is

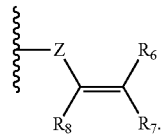

In a further embodiment is a compound of Formula (IIa) wherein Z is C(=O), NHC(=O), N(CH₃)C(=O), or S(=O)₂. In some embodiments, Z is C(=O). In some embodiments, Z is NHC(=O). In some embodiments, Z is N(CH₃)C(=O). In some embodiments, Z is S(=O)₂.

In another embodiment is a compound of Formula (IIa) wherein R₆, R₇ and R₈ are H. In another embodiment is a compound of Formula (IIa) wherein R₇ and R₈ are H and R₆ is L₃-J-W. In a further embodiment, R₆ is H, substituted or unsubstituted C₁-C₆alkyl, substituted or unsubstituted C₁-C₆heteroalkyl, (C₁-C₆dialkylamino)C₁-C₆alkyl, ((C₁-C₆alkyl)(C₃-C₆cycloalkyl)amino)C₁-C₆alkyl, substituted or unsubstituted $C_1$-$C_6$alkyl$C_3$-$C_6$cycloalkyl, or $C_1$-$C_4$alkyl ($C_2$-$C_7$heterocycloalkyl). In yet a further embodiment is a compound of Formula (IIa) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (IIa) wherein $R_6$ is halogen. In some embodiments is a compound of Formula (IIa) wherein $R_6$ is —CN.

In another embodiment is a compound of Formula (IIa) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IIa) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (IIa) wherein $R_7$ is halogen. In some embodiments is a compound of Formula (IIa) wherein $R_7$ is —CN. In some embodiments is a compound of Formula (IIa) wherein $R_6$ is H, $R_8$ is halogen, and $R_7$ is $L_3$-J-W. In some embodiments is a compound of Formula (IIa) wherein $R_6$ is H, $R_8$ is —CN, and $R_7$ is $L_3$-J-W.

In another embodiment is a compound of Formula (IIa) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —$CH_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —$CH_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (IIa), wherein W is H. In another embodiment of the aforementioned embodiments is a compound of Formula (IIa), wherein W is —CN. In another embodiment of the aforementioned embodiments is a compound of Formula (IIa), wherein W is $NR_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (IIa) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (IIa) wherein $R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})$ $S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (IIa) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (IIa) wherein $R_2$ is halogen. In further embodiments is a compound of Formula (IIa) wherein $R_2$ is Cl. In further embodiments is a compound of Formula (IIa) wherein $R_2$ is F. In further embodiments is a compound of Formula (IIa) wherein $R_2$ is Br. In some embodiments is a compound of Formula (IIa) wherein $R_2$ is substituted or unsubstituted alkyl. In further embodiments is a compound of Formula (IIa) wherein $R_2$ is methyl.

In another embodiment is a compound of Formula (IIa) wherein $R_2$ is -$L_2$-Ar. In some embodiments is a compound of Formula (IIa) wherein $L_2$ is a bond, —$CH_2$—, —CH (OH)—, —C(O)—, —$CH_2O$—, —$OCH_2$—, —$SCH_2$, —$CH_2S$—, —N($R_{21}$)—, —O—, —S—, —S(O)—, —S (O)$_2$—, —N($R_{21}$)S(O)$_2$—, or —S(O)$_2$N($R_{21}$)—. In some embodiments is a compound of Formula (IIa) wherein $L_2$ is —$CH_2$—, —$CH_2O$—, —$OCH_2$—, or —O—. In further embodiments is a compound of Formula (IIa) wherein $L_2$ is —O—. In another embodiment of Formula (IIa) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (IIa) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (IIa), wherein n is 0. In some embodiments of the aforementioned embodiments is a compound of Formula (IIa), wherein n is 1. In some embodiments of the aforementioned embodiments is a compound of Formula (IIa), wherein n is 2. In some embodiments of the aforementioned embodiments is a compound of Formula (IIa), wherein n is 3. In some embodiments of the aforementioned embodiments is a compound of Formula (IIa), wherein n is 4.

In another embodiment are compounds having the structure of Formula (III):

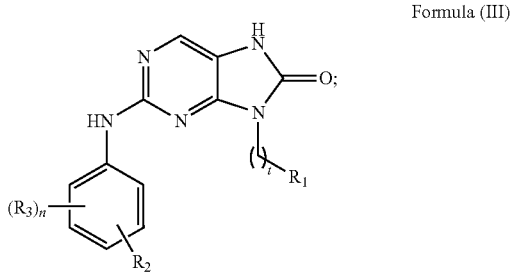

Formula (III)

wherein:
$R_1$ is —Y-$L_2$-Ar, or an optionally substituted group selected from among alkyl, heteroalkyl, cycloalkyl, heterocycloalkyl, aryl, and heteroaryl;
$R_2$ is

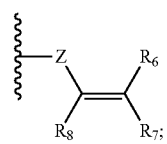

Y is an optionally substituted group selected from among alkyl, heteroalkyl, cycloalkyl, heterocycloalkyl, aryl, and heteroaryl;
Z is C(=O), OC(=O), N($R_{21}$)C(=O), C(=S), S(=O)$_p$, OS(=O)$_p$, or N($R_{21}$)S(=O)$_p$, where p is 1 or 2;
$L_2$ is a bond, —$CH_2$—, —CH(OH)—, —C(O)—, —$CH_2$O—, —O$CH_2$—, —S$CH_2$—, —$CH_2$S—, —N($R_{21}$)—, —O—, —S—, —S(O)—, —S(O)$_2$—, —N($R_{21}$)S(O)$_2$—, or —S(O)$_2$N($R_{21}$)—;

Ar is a substituted or unsubstituted cycloalkyl, substituted or unsubstituted heterocycloalkyl, substituted or unsubstituted aryl, or a substituted or unsubstituted heteroaryl;
each $R_3$ is each independently halogen, —CN, —$NO_2$, —OH, —$OCF_3$, —$OCH_2$F, —$OCF_2$H, —$CF_3$, —$SR_{21}$, —N($R_{21}$)S(=O)$_2R_{23}$, —S(=O)$_2$N($R_{21}$)($R_{22}$), —S(=O)$R_{23}$, —S(=O)$_2R_{23}$, —C(=O)$R_{23}$, —OC(=O)$R_{23}$, —$CO_2R_{21}$, —N($R_{21}$)($R_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;
each $R_{21}$ and $R_{22}$ are each independently H, substituted or unsubstituted $C_1$-$C_6$alkyl, or substituted or unsubstituted $C_3$-$C_8$cycloalkyl;
$R_{23}$ is each independently substituted or unsubstituted $C_1$-$C_6$alkyl, or substituted or unsubstituted $C_3$-$C_8$cycloalkyl;
n is 0-4;
t is 0-2;
$R_6$ is H, halogen, —CN, or $L_3$-J-W;
$R_7$ and $R_8$ are independently H, halogen, —CN, or $L_3$-J-W; or $R_7$ and $R_8$ taken together form a bond;
each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;
each W is H, —CN, or —$NR_{25}R_{26}$;
$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or
a pharmaceutically acceptable solvate, pharmaceutically acceptable salt, or pharmaceutically acceptable prodrug thereof.

In one embodiment is a compound of Formula (III) wherein $R_1$ is —Y-$L_2$-Ar, or an optionally substituted group selected from among alkyl, heteroalkyl, cycloalkyl, heterocycloalkyl, aryl, and heteroaryl. In another embodiment is a compound of Formula (III) wherein $R_1$ is —Y-$L_2$-Ar. In another embodiment is a compound of Formula (III) wherein $R_1$ is —Y-$L_2$-Ar, Y is phenyl, $L_2$ is —O—, and Ar is phenyl. In some embodiments is a compound of Formula (III) wherein $R_1$ is optionally substituted alkyl, optionally substituted cycloalkyl, optionally substituted heterocycloalkyl, optionally substituted heteroaryl, or optionally substituted aryl. In some embodiments is a compound of Formula (III) wherein $R_1$ is optionally substituted alkyl. In some embodiments is a compound of Formula (III) wherein $R_1$ is optionally substituted cycloalkyl. In some embodiments is a compound of Formula (III) wherein $R_1$ is optionally substituted heterocycloalkyl. In some embodiments is a compound of Formula (III) wherein $R_1$ is optionally substituted heteroaryl. In some embodiments is a compound of Formula (III) wherein $R_1$ is optionally substituted aryl.

In another embodiment is a compound of Formula (III) wherein $R_2$ is

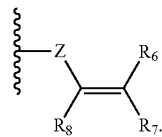

In a further embodiment is a compound of Formula (III) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (III) wherein $R_6$, $R_7$ and $R_8$ are H. In another embodiment is a compound of Formula (III) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (III) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (III) wherein $R_6$ is halogen. In some embodiments is a compound of Formula (III) wherein $R_6$ is —CN.

In another embodiment is a compound of Formula (III) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (III) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (III) wherein $R_7$ is halogen. In some embodiments is a compound of Formula (III) wherein $R_7$ is —CN. In some embodiments is a compound of Formula (III) wherein $R_6$ is H, $R_8$ is halogen, and $R_7$ is $L_3$-J-W. In some embodiments is a compound of Formula (III) wherein $R_6$ is H, $R_8$ is —CN, and $R_7$ is $L_3$-J-W.

In another embodiment is a compound of Formula (III) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (III), wherein W is H. In another embodiment of the aforementioned embodiments is a compound of Formula (III), wherein W is —CN. In another embodiment of the aforementioned embodiments is a compound of Formula (III), wherein W is NR$_{25}$R$_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —CH$_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —CH$_3$ and $R_{26}$ is cyclopropyl. In some embodiments, $R_{25}$ is —CH$_3$ and $R_{26}$ is cyclobutyl.

In another embodiment is a compound of Formula (III) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (III) wherein $R_3$ is each independently halogen, —NH$_2$, —N(CH$_3$)$_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In another embodiment of the aforementioned embodiments is a compound of Formula (III) wherein t is 0. In a further embodiment of the aforementioned embodiments is a compound of Formula (III) wherein t is 1. In a further embodiment of the aforementioned embodiments is a compound of Formula (III) wherein t is 2.

In a further embodiment of the aforementioned embodiments is a compound of Formula (III), wherein n is 0. In some embodiments of the aforementioned embodiments is a compound of Formula (III), wherein n is 1. In some embodiments of the aforementioned embodiments is a compound of Formula (III), wherein n is 2. In some embodiments of the aforementioned embodiments is a compound of Formula (III), wherein n is 3. In some embodiments of the aforementioned embodiments is a compound of Formula (III), wherein n is 4.

In another embodiment are compounds having the structure of Formula (IIIa):

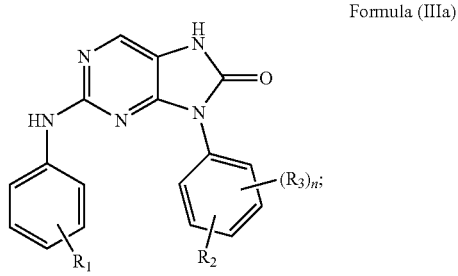

Formula (IIIa)

wherein:
$R_1$ is halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

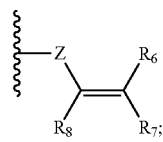

$R_2$ is halogen, —CN, —NO$_2$, —OH, —OR$_{20}$, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -L$_2$-Ar;
$L_2$ is a bond, —CH$_2$—, —CH(OH)—, —C(O)—, —CH$_2$O—, —OCH$_2$—, —SCH$_2$—, —CH$_2$S—, —N(R$_{21}$)—, —O—, —S—, —S(O)—, —S(O)$_2$—, —N(R$_{21}$)S(O)$_2$—, or —S(O)$_2$N(R$_{21}$)—;
Ar is a substituted or unsubstituted cycloalkyl, substituted or unsubstituted heterocycloalkyl, substituted or unsubstituted aryl, or a substituted or unsubstituted heteroaryl;

Z is C(=O), OC(=O), N(R$_{21}$)C(=O), C(=S), S(=O)$_p$, OS(=O)$_x$, or N(R$_{21}$)S(=O)$_p$, where p is 1 or 2;
each $R_3$ is each independently halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;
$R_{20}$ is substituted or unsubstituted C$_1$-C$_6$alkyl, substituted or unsubstituted C$_1$-C$_8$heteroalkyl, or substituted or unsubstituted phenyl;
each $R_{21}$ and $R_{22}$ are each independently H, substituted or unsubstituted C$_1$-C$_6$alkyl, or substituted or unsubstituted C$_3$-C$_8$cycloalkyl;
$R_{23}$ is each independently substituted or unsubstituted C$_1$-C$_6$alkyl, or substituted or unsubstituted C$_3$-C$_8$cycloalkyl;
n is 0-4;
$R_6$ is H, halogen, —CN, or L$_3$-J-W;
$R_7$ and $R_8$ are independently H, halogen, —CN, or L$_3$-J-W; or R$_7$ and R$_8$ taken together form a bond;
$L_3$ and J are each independently a bond, substituted or unsubstituted C$_1$-C$_6$ alkylene, substituted or unsubstituted C$_3$-C$_6$ cycloalkylene, substituted or unsubstituted C$_1$-C$_6$ heteroalkylene, substituted or unsubstituted C$_2$-C$_7$ heterocycloalkylene, substituted or unsubstituted C$_6$-C$_{12}$ arylene, substituted or unsubstituted C$_3$-C$_{12}$ heteroarylene, —C(=O)—, —O—, or —S—;
each W is H, —CN, or —NR$_{25}$R$_{26}$;
$R_{25}$ and $R_{26}$ are each independently H, substituted or unsubstituted C$_1$-C$_6$ alkyl, substituted or unsubstituted C$_3$-C$_6$ cycloalkyl, substituted or unsubstituted C$_1$-C$_6$ heteroalkyl, substituted or unsubstituted C$_2$-C$_7$ heterocycloalkyl, substituted or unsubstituted C$_6$-C$_{12}$ aryl, or substituted or unsubstituted C$_3$-C$_{12}$ heteroaryl; or
a pharmaceutically acceptable solvate, pharmaceutically acceptable salt, or pharmaceutically acceptable prodrug thereof.

In one embodiment is a compound of Formula (IIIa) wherein $R_1$ is halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

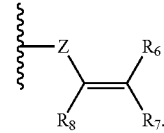

In another embodiment is a compound of Formula (IIIa) wherein $R_1$ is halogen, substituted or unsubstituted alkyl, substituted or unsubstituted alkoxy, or substituted or unsubstituted heteroalkyl. In some embodiments is a compound of Formula (IIIa) wherein $R_1$ is halogen. In further embodiments is a compound of Formula (IIIa) wherein $R_1$ is Cl. In further embodiments is a compound of Formula (IIIa) wherein $R_1$ is F. In further embodiments is a compound of Formula (IIIa) wherein $R_1$ is Br. In some embodiments is a compound of Formula (IIIa) wherein $R_1$ is substituted or unsubstituted alkyl. In further embodiments is a compound of Formula (IIIa) wherein $R_1$ is methyl. In some embodiments is a compound of Formula (IIIa) wherein $R_1$ is substituted or unsubstituted alkoxy. In some embodiments is a compound of Formula (IIIa) wherein $R_1$ is substituted or unsubstituted heteroalkyl.

In another embodiment is a compound of Formula (IIIa) wherein $R_1$ is

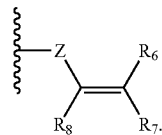

In a further embodiment is a compound of Formula (IIIa) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (IIIa) wherein $R_6$, $R_7$ and $R_8$ are H. In another embodiment is a compound of Formula (IIIa) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, $((C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IIIa) wherein $R_6$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or $((C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted $(C_1$-$C_6$dialkylamino)$C_1$-$C_6$alkyl. In some embodiments, $R_6$ is substituted or unsubstituted $((C_1$-$C_6$alkyl)($C_3$-$C_6$cycloalkyl)amino)$C_1$-$C_6$alkyl. In some embodiments is a compound of Formula (IIIa) wherein $R_6$ is halogen. In some embodiments is a compound of Formula (IIIa) wherein $R_6$ is —CN.

In another embodiment is a compound of Formula (IIIa) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, $((C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IIIa) wherein $R_7$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or $((C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted $(C_1$-$C_6$dialkylamino)$C_1$-$C_6$alkyl. In some embodiments, $R_7$ is substituted or unsubstituted $((C_1$-$C_6$alkyl)($C_3$-$C_6$cycloalkyl)amino)$C_1$-$C_6$alkyl. In some embodiments is a compound of Formula (IIIa) wherein $R_7$ is halogen. In some embodiments is a compound of Formula (IIIa) wherein $R_7$ is —CN. In some embodiments is a compound of Formula (IIIa) wherein $R_6$ is H, $R_8$ is halogen, and $R_7$ is $L_3$-J-W. In some embodiments is a compound of Formula (IIIa) wherein $R_6$ is H, $R_8$ is —CN, and $R_7$ is $L_3$-J-W.

In another embodiment is a compound of Formula (IIIa) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —CH$_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (IIIa), wherein W is H. In another embodiment of the aforementioned embodiments is a compound of Formula (IIIa), wherein W is —CN. In another embodiment of the aforementioned embodiments is a compound of Formula (IIIa), wherein W is NR$_{25}$R$_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —CH$_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —CH$_3$ and $R_{26}$ is cyclopropyl. In some embodiments, $R_{25}$ is —CH$_3$ and $R_{26}$ is cyclobutyl.

In another embodiment is a compound of Formula (IIIa) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, $((C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, $(C_1$-$C_6$dialkylamino)$C_1$-$C_6$alkyl, or $((C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is $(C_1$-$C_6$dialkylamino)$C_1$-$C_6$alkyl. In some embodiments, $R_6$ is $((C_1$-$C_6$alkyl)($C_3$-$C_6$cycloalkyl)amino)$C_1$-$C_6$alkyl.

In some embodiments is a compound of Formula (IIIa) wherein $R_2$ is halogen, —CN, —NO$_2$, —OH, —OR$_{20}$, —OCF₃, —OCH₂F, —OCF₂H, —CF₃, —SR₂₁, —N(R₂OS(=O)₂R₂₃, —S(=O)₂N(R₂₁)(R₂₂), —S(=O)R₂₃, —S(=O)₂R₂₃, —C(=O)R₂₃, —OC(=O)R₂₃, —CO₂R₂₁, —N(R₂₁)(R₂₂), substituted or unsubstituted alkyl, substituted or unsubstituted heteroalkyl, substituted or unsubstituted heterocycloalkyl, substituted or unsubstituted cycloalkyl, or -L₂-Ar. In some embodiments is a compound of Formula (IIIa) wherein R₂ is halogen, substituted or unsubstituted alkyl, substituted or unsubstituted heteroalkyl, substituted or unsubstituted heterocycloalkyl, substituted or unsubstituted cycloalkyl, or -L₂-Ar. In some embodiments is a compound of Formula (IIIa) wherein R₂ is halogen. In further embodiments is a compound of Formula (IIIa) wherein R₂ is Cl. In further embodiments is a compound of Formula (IIIa) wherein R₂ is F. In further embodiments is a compound of Formula (IIIa) wherein R₂ is Br. In some embodiments is a compound of Formula (IIIa) wherein R₂ is substituted or unsubstituted alkyl. In further embodiments is a compound of Formula (IIIa) wherein R₂ is methyl.

In another embodiment is a compound of Formula (IIIa) wherein R₂ is -L₂-Ar. In some embodiments is a compound of Formula (IIIa) wherein L₂ is a bond, —CH₂—, —CH(OH)—, —C(O)—, —CH₂O—, —OCH₂—, —SCH₂, —CH₂S—, —N(R₂₁)—, —O—, —S—, —S(O)—, —S(O)₂—, —N(R₂₁)S(O)₂—, or —S(O)₂N(R₂₁)—. In some embodiments is a compound of Formula (IIIa) wherein L₂ is —CH₂—, —CH₂O—, —OCH₂—, or —O—. In further embodiments is a compound of Formula (IIIa) wherein L₂ is —O—. In another embodiment is a compound of Formula (IIIa) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (IIIa) wherein R₃ is each independently halogen, —NH₂, —N(CH₃)₂, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, R₃ is substituted or unsubstituted alkyl. In some embodiments, R₃ is substituted or unsubstituted cycloalkyl. In some embodiments, R₃ is substituted or unsubstituted heterocycloalkyl. In some embodiments, R₃ is halogen. In further embodiments, R₃ is F, Cl or Br.

In a further embodiment of the aforementioned embodiments is a compound of Formula (IIIa), wherein n is 0. In some embodiments of the aforementioned embodiments is a compound of Formula (IIIa), wherein n is 1. In some embodiments of the aforementioned embodiments is a compound of Formula (IIIa), wherein n is 2. In some embodiments of the aforementioned embodiments is a compound of Formula (IIIa), wherein n is 3. In some embodiments of the aforementioned embodiments is a compound of Formula (IIIa), wherein n is 4.

In another embodiment are compounds having the structure of Formula (IV):

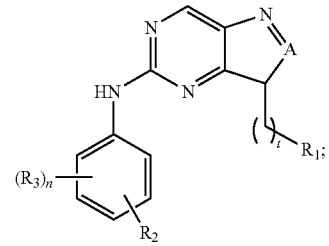

Formula (IV)

wherein:
A is =C(R₉)—, or =N—;
R₁ is —Y-L₂-Ar, or an optionally substituted group selected from among alkyl, heteroalkyl, cycloalkyl, heterocycloalkyl, aryl, and heteroaryl;
R₂ is

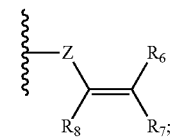

Y is an optionally substituted group selected from among alkyl, heteroalkyl, cycloalkyl, heterocycloalkyl, aryl, and heteroaryl;
Z is C(=O), OC(=O), N(R₂₁)C(=O), C(=S), S(=O)ₚ, OS(=O)ₚ, or N(R₂₁)S(=O)ₚ, where p is 1 or 2;
L₂ is a bond, —CH₂—, —CH(OH)—, —C(O)—, —CH₂O—, —OCH₂—, —SCH₂, —CH₂S—, —N(R₂₁)—, —O—, —S—, —S(O)—, —S(O)₂—, —N(R₂₁)S(O)₂—, or —S(O)₂N(R₂₁)—;
Ar is a substituted or unsubstituted cycloalkyl, substituted or unsubstituted heterocycloalkyl, substituted or unsubstituted aryl, or a substituted or unsubstituted heteroaryl;
each R₃ is each independently halogen, —CN, —NO₂, —OH, —OCF₃, —OCH₂F, —OCF₂H, —CF₃, —SR₂₁, —N(R₂₁)S(=O)₂R₂₃, —S(=O)₂N(R₂₁)(R₂₂), —S(=O)R₂₃, —S(=O)₂R₂₃, —C(=O)R₂₃, —OC(=O)R₂₃, —CO₂R₂₁, —N(R₂₁)(R₂₂), substituted or unsubstituted alkyl, substituted or unsubstituted alkoxy, substituted or unsubstituted heteroalkyl, substituted or unsubstituted heterocycloalkyl, or substituted or unsubstituted cycloalkyl;
R₉ is H, halogen, —CN, —OH, —NH₂, —SH, substituted or unsubstituted C₁-C₆alkyl, substituted or unsubstituted C₁-C₄alkoxy, substituted or unsubstituted C₁-C₆heteroalkyl, substituted or unsubstituted phenyl, substituted or unsubstituted heteroaryl, or substituted or unsubstituted C₃-C₈cycloalkyl;
each R₂₁ and R₂₂ are each independently H, substituted or unsubstituted C₁-C₆alkyl, or substituted or unsubstituted C₃-C₈cycloalkyl;
R₂₃ is each independently substituted or unsubstituted C₁-C₆alkyl, or substituted or unsubstituted C₃-C₈cycloalkyl;
n is 0-4;
t is 0-2;
R₆ is H, halogen, —CN, or L₃-J-W;
R₇ and R₈ are independently H, halogen, —CN, or L₃-J-W; or R₇ and R₈ taken together form a bond;

each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (IV) wherein A is =C(H)— or =N—. In some embodiments is a compound of Formula (IV) wherein A is =N—. In some embodiments is a compound of Formula (IV) wherein A is =C(R$_9$)—. In some embodiments is a compound of Formula (IV) wherein $R_9$ is H, halogen, substituted or unsubstituted $C_1$-$C_6$alkyl, substituted or unsubstituted $C_1$-$C_4$alkoxy, or substituted or unsubstituted $C_1$-$C_6$heteroalkyl. In some embodiments is a compound of Formula (IV) wherein $R_9$ is H. In some embodiments is a compound of Formula (IV) wherein $R_9$ is halogen. In some embodiments is a compound of Formula (IV) wherein $R_9$ is substituted or unsubstituted $C_1$-$C_6$alkyl. In some embodiments is a compound of Formula (IV) wherein $R_9$ is substituted or unsubstituted $C_1$-$C_4$alkoxy. In some embodiments is a compound of Formula (IV) wherein $R_9$ is substituted or unsubstituted $C_1$-$C_6$heteroalkyl.

In one embodiment is a compound of Formula (IV) wherein $R_1$ is —Y-$L_2$-Ar, or an optionally substituted group selected from among alkyl, heteroalkyl, cycloalkyl, heterocycloalkyl, aryl, and heteroaryl. In another embodiment is a compound of Formula (IV) wherein $R_1$ is —Y-$L_2$-Ar. In another embodiment is a compound of Formula (IV) wherein $R_1$ is —Y-$L_2$-Ar, Y is phenyl, $L_2$ is —O—, and Ar is phenyl. In some embodiments is a compound of Formula (IV) wherein $R_1$ is optionally substituted alkyl, optionally substituted cycloalkyl, optionally substituted heterocycloalkyl, optionally substituted heteroaryl, or optionally substituted aryl. In some embodiments is a compound of Formula (IV) wherein $R_1$ is optionally substituted alkyl. In some embodiments is a compound of Formula (IV) wherein $R_1$ is optionally substituted cycloalkyl. In some embodiments is a compound of Formula (IV) wherein $R_1$ is optionally substituted heterocycloalkyl. In some embodiments is a compound of Formula (IV) wherein $R_1$ is optionally substituted heteroaryl. In some embodiments is a compound of Formula (IV) wherein $R_1$ is optionally substituted aryl.

In another embodiment is a compound of Formula (IV) wherein $R_2$ is

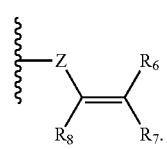

In a further embodiment is a compound of Formula (IV) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (IV) wherein $R_6$, $R_7$ and $R_8$ are H. In another embodiment is a compound of Formula (IV) wherein $R_7$ and $R_8$ are H and $R_6$ is $L_3$-J-W. In a further embodiment, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IV) wherein $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is substituted or unsubstituted ($C_1$-$C_6$dialkylamino)$C_1$-$C_6$alkyl. In some embodiments, $R_6$ is substituted or unsubstituted (($C_1$-$C_6$alkyl)($C_3$-$C_6$cycloalkyl)amino)$C_1$-$C_6$alkyl. In some embodiments is a compound of Formula (IV) wherein $R_6$ is halogen. In some embodiments is a compound of Formula (IV) wherein $R_6$ is —CN.

In another embodiment is a compound of Formula (IV) wherein $R_6$ and $R_8$ are H and $R_7$ is $L_3$-J-W. In a further embodiment, $R_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IV) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (IV) wherein $R_7$ is halogen. In some embodiments is a compound of Formula (IV) wherein $R_7$ is —CN. In some embodiments is a compound of Formula (IV) wherein $R_6$ is H, $R_8$ is halogen, and $R_7$ is $L_3$-J-W. In some embodiments is a compound of Formula (IV) wherein $R_6$ is H, $R_8$ is —CN, and $R_7$ is $L_3$-J-W.

In another embodiment is a compound of Formula (IV) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —CH$_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —$CH_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (IV), wherein W is H. In another embodiment of the aforementioned embodiments is a compound of Formula (IV), wherein W is —CN. In another embodiment of the aforementioned embodiments is a compound of Formula (IV), wherein W is $NR_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (IV) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (IV) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In another embodiment of the aforementioned embodiments is a compound of Formula (IV) wherein t is 0. In a further embodiment of the aforementioned embodiments is a compound of Formula (IV) wherein t is 1. In a further embodiment of the aforementioned embodiments is a compound of Formula (IV) wherein t is 2.

In a further embodiment of the aforementioned embodiments is a compound of Formula (IV), wherein n is 0. In some embodiments of the aforementioned embodiments is a compound of Formula (IV), wherein n is 1. In some embodiments of the aforementioned embodiments is a compound of Formula (IV), wherein n is 2. In some embodiments of the aforementioned embodiments is a compound of Formula (IV), wherein n is 3. In some embodiments of the aforementioned embodiments is a compound of Formula (IV), wherein n is 4.

In another embodiment are compounds having the structure of Formula (IVa):

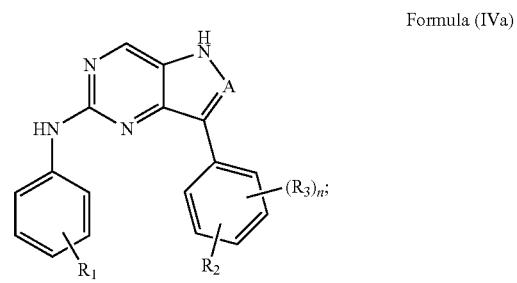

Formula (IVa)

wherein:
A is =C($R_9$)—, or =N—;
$R_1$ is halogen, —CN, —$NO_2$, —OH, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted alkoxy, substituted or unsubstituted heteroalkyl, substituted or unsubstituted heterocycloalkyl, substituted or unsubstituted cycloalkyl, or

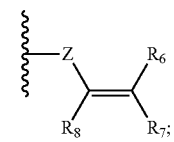

$R_2$ is halogen, —CN, —$NO_2$, —OH, —$OR_{20}$, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar;
$L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—;
Ar is a substituted or unsubstituted cycloalkyl, substituted or unsubstituted heterocycloalkyl, substituted or unsubstituted aryl, or a substituted or unsubstituted heteroaryl;
Z is C(=O), OC(=O), $N(R_{21})C(=O)$, C(=S), $S(=O)_p$, $OS(=O)_x$, or $N(R_{21})S(=O)_p$, where p is 1 or 2;
each $R_3$ is each independently halogen, —CN, —$NO_2$, —OH, —$OCF_3$, —$OCH_2F$, —$OCF_2H$, —$CF_3$, —$SR_{21}$, —$N(R_{21})S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;

$R_9$ is H, halogen, —CN, —OH, —NH$_2$, —SH, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

$L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl; or a pharmaceutically acceptable solvate, pharmaceutically acceptable salt, or pharmaceutically acceptable prodrug thereof.

In one embodiment is a compound of Formula (IVa) wherein A is =C(H)— or =N—. In some embodiments is a compound of Formula (IVa) wherein A is =N—. In some embodiments is a compound of Formula (IVa) wherein A is =C(R$_9$)—. In some embodiments is a compound of Formula (IVa) wherein R$_9$ is H, halogen, substituted or unsubstituted $C_1$-$C_6$alkyl, substituted or unsubstituted $C_1$-$C_4$alkoxy, or substituted or unsubstituted $C_1$-$C_6$heteroalkyl. In some embodiments is a compound of Formula (IVa) wherein R$_9$ is H. In some embodiments is a compound of Formula (IVa) wherein R$_9$ is halogen. In some embodiments is a compound of Formula (IVa) wherein R$_9$ is substituted or unsubstituted $C_1$-$C_6$alkyl. In some embodiments is a compound of Formula (IVa) wherein R$_9$ is substituted or unsubstituted $C_1$-$C_4$alkoxy. In some embodiments is a compound of Formula (IVa) wherein R$_9$ is substituted or unsubstituted $C_1$-$C_6$heteroalkyl.

In another embodiment is a compound of Formula (IVa) wherein R$_1$ is halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, substituted or unsubstituted cycloalkyl, or

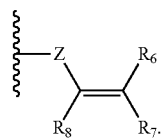

In another embodiment is a compound of Formula (IVa) wherein R$_1$ is halogen, substituted or unsubstituted alkyl, substituted or unsubstituted alkoxy, or substituted or unsubstituted heteroalkyl. In some embodiments is a compound of Formula (IVa) wherein R$_1$ is halogen. In further embodiments is a compound of Formula (IVa) wherein R$_1$ is Cl. In further embodiments is a compound of Formula (IVa) wherein R$_1$ is F. In further embodiments is a compound of Formula (IVa) wherein R$_1$ is Br. In some embodiments is a compound of Formula (IVa) wherein R$_1$ is substituted or unsubstituted alkyl. In further embodiments is a compound of Formula (IVa) wherein R$_1$ is methyl. In some embodiments is a compound of Formula (IVa) wherein R$_1$ is substituted or unsubstituted alkoxy. In some embodiments is a compound of Formula (IVa) wherein R$_1$ is substituted or unsubstituted heteroalkyl.

In another embodiment is a compound of Formula (IVa) wherein R$_1$ is

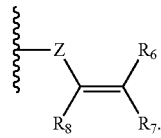

In a further embodiment is a compound of Formula (IVa) wherein Z is C(=O), NHC(=O), N(CH$_3$)C(=O), or S(=O)$_2$. In some embodiments, Z is C(=O). In some embodiments, Z is NHC(=O). In some embodiments, Z is N(CH$_3$)C(=O). In some embodiments, Z is S(=O)$_2$.

In another embodiment is a compound of Formula (IVa) wherein R$_6$, R$_7$ and R$_8$ are H. In another embodiment is a compound of Formula (IVa) wherein R$_7$ and R$_8$ are H and R$_6$ is $L_3$-J-W. In a further embodiment, R$_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In yet a further embodiment is a compound of Formula (IVa) wherein R$_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, R$_6$ is substituted or unsubstituted $C_1$-$C_6$alkyl. In some embodiments, R$_6$ is substituted or unsubstituted $C_1$-$C_6$heteroalkyl. In some embodiments, R$_6$ is substituted or unsubstituted ($C_1$-$C_6$dialkylamino)$C_1$-$C_6$alkyl. In some embodiments, R$_6$ is substituted or unsubstituted (($C_1$-$C_6$alkyl)($C_3$-$C_6$cycloalkyl)amino)$C_1$-$C_6$alkyl. In some embodiments is a compound of Formula (IVa) wherein R$_6$ is halogen. In some embodiments is a compound of Formula (IVa) wherein R$_6$ is —CN.

In another embodiment is a compound of Formula (IVa) wherein R$_6$ and R$_8$ are H and R$_7$ is $L_3$-J-W. In a further embodiment, R$_7$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-

$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl($C_2$-$C_7$heterocycloalkyl). In yet a further embodiment is a compound of Formula (IVa) wherein $R_7$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_7$ is substituted or unsubstituted $C_1$-$C_6$alkyl. In some embodiments, $R_7$ is substituted or unsubstituted $C_1$-$C_6$heteroalkyl. In some embodiments, $R_7$ is substituted or unsubstituted ($C_1$-$C_6$dialkylamino)$C_1$-$C_6$alkyl. In some embodiments, $R_7$ is substituted or unsubstituted (($C_1$-$C_6$alkyl)($C_3$-$C_6$cycloalkyl)amino)$C_1$-$C_6$alkyl. In some embodiments is a compound of Formula (IVa) wherein $R_7$ is halogen. In some embodiments is a compound of Formula (IVa) wherein $R_7$ is —CN. In some embodiments is a compound of Formula (IVa) wherein $R_6$ is H, $R_8$ is halogen, and $R_7$ is $L_3$-J-W. In some embodiments is a compound of Formula (IVa) wherein $R_6$ is H, $R_8$ is —CN, and $R_7$ is $L_3$-J-W.

In another embodiment is a compound of Formula (IVa) wherein $R_6$ and $R_8$ are H; $R_7$ is $L_3$-J-W; $L_3$ is a bond, substituted or unsubstituted $C_1$-$C_6$ alkylene, or substituted or unsubstituted $C_3$-$C_6$ cycloalkylene; and J is a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In further embodiments, $L_3$ is a bond. In further embodiments, $L_3$ is substituted or unsubstituted $C_3$-$C_6$ cycloalkylene. In further embodiments, $L_3$ is substituted or unsubstituted $C_1$-$C_6$ alkylene. In yet a further embodiment, $L_3$ is —$CH_2$—. In further embodiments, J is substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, or substituted or unsubstituted $C_3$-$C_{12}$ heteroarylene. In some embodiments, J is substituted or unsubstituted $C_1$-$C_6$ alkylene. In further embodiments, J is —$CH_2$—. In some embodiments, J is substituted or unsubstituted $C_1$-$C_6$ cycloalkylene. In further embodiments, J is cyclopropyl. In some embodiments, J is substituted or unsubstituted $C_2$-$C_7$ heterocycloalkylene. In further embodiments, J is pyrrolidinyl, piperidinyl, piperizinyl, morpholinyl, imidazolyl, or pyridinyl. In a further embodiment of the aforementioned embodiments is a compound of Formula (IVa), wherein W is H. In another embodiment of the aforementioned embodiments is a compound of Formula (IVa), wherein W is —CN. In another embodiment of the aforementioned embodiments is a compound of Formula (IVa), wherein W is $NR_{25}R_{26}$. In a further embodiment, $R_{25}$ is H, substituted or unsubstituted $C_1$-$C_6$ alkyl, or substituted or unsubstituted $C_3$-$C_6$ cycloalkyl; and $R_{26}$ is substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl. In some embodiments, $R_{25}$ and $R_{26}$ are —$CH_3$. In some embodiments, $R_{25}$ and $R_{26}$ are cyclopropyl. In some embodiments, $R_{25}$ is H and $R_{26}$ is cyclopropyl. In some embodiments, $R_{25}$ is H and $R_{26}$ is cyclobutyl. In some embodiments, $R_{25}$ is —$CH_3$ and $R_{26}$ is cyclopropyl. In some embodiments, $R_{25}$ is —$CH_3$ and $R_{26}$ is cyclobutyl.

In another embodiment is a compound of Formula (IVa) wherein $R_7$ and $R_8$ taken together form a bond; and $R_6$ is $L_3$-J-W. In further embodiments, $R_6$ is H, substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, (($C_1$-$C_6$alkyl)($C_3$-$C_6$cycloalkyl)amino)$C_1$-$C_6$alkyl, substituted or unsubstituted $C_1$-$C_6$alkyl$C_3$-$C_6$cycloalkyl, or $C_1$-$C_4$alkyl ($C_2$-$C_7$heterocycloalkyl). In further embodiments, $R_6$ is substituted or unsubstituted $C_1$-$C_6$alkyl, substituted or unsubstituted $C_1$-$C_6$heteroalkyl, ($C_1$-$C_6$dialkylamino)$C_1$-$C_6$alkyl, or (($C_1$-$C_6$alkyl)($C_3$-$C_6$cycloalkyl)amino)$C_1$-$C_6$alkyl. In some embodiments, $R_6$ is substituted or unsubstituted $C_1$-$C_6$alkyl. In some embodiments, $R_6$ is substituted or unsubstituted $C_1$-$C_6$heteroalkyl. In some embodiments, $R_6$ is ($C_1$-$C_6$dialkylamino)$C_1$-$C_6$alkyl. In some embodiments, $R_6$ is (($C_1$-$C_6$alkyl)($C_3$-$C_6$cycloalkyl)amino)$C_1$-$C_6$alkyl.

In some embodiments is a compound of Formula (IVa) wherein $R_2$ is halogen, —CN, —$NO_2$, —OH, —$OR_{26}$, —$OCF_3$, —$OCH_2F$, —$OCF_2H$, —$CF_3$, —$SR_{21}$, —$N(R_{21})$ $S(=O)_2R_{23}$, —$S(=O)_2N(R_{21})(R_{22})$, —$S(=O)R_{23}$, —$S(=O)_2R_{23}$, —$C(=O)R_{23}$, —$OC(=O)R_{23}$, —$CO_2R_{21}$, —$N(R_{21})(R_{22})$, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (IVa) wherein $R_2$ is halogen, substituted or unsubstituted alkyl, substituted or unsubstituted heteroalkyl, substituted or unsubstituted heterocycloalkyl, substituted or unsubstituted cycloalkyl, or -$L_2$-Ar. In some embodiments is a compound of Formula (IVa) wherein $R_2$ is halogen. In further embodiments is a compound of Formula (IVa) wherein $R_2$ is Cl. In further embodiments is a compound of Formula (IVa) wherein $R_2$ is F. In further embodiments is a compound of Formula (IVa) wherein $R_2$ is Br. In some embodiments is a compound of Formula (IVa) wherein $R_2$ is substituted or unsubstituted alkyl. In further embodiments is a compound of Formula (IVa) wherein $R_2$ is methyl.

In another embodiment is a compound of Formula (IVa) wherein $R_2$ is -$L_2$-Ar. In some embodiments is a compound of Formula (IVa) wherein $L_2$ is a bond, —$CH_2$—, —CH(OH)—, —C(O)—, —$CH_2O$—, —$OCH_2$—, —$SCH_2$, —$CH_2S$—, —$N(R_{21})$—, —O—, —S—, —S(O)—, —$S(O)_2$—, —$N(R_{21})S(O)_2$—, or —$S(O)_2N(R_{21})$—. In some embodiments is a compound of Formula (IVa) wherein $L_2$ is —$CH_2$—, —$CH_2O$—, —$OCH_2$—, or —O—. In further embodiments is a compound of Formula (IVa) wherein $L_2$ is —O—. In another embodiment is a compound of Formula (IVa) wherein Ar is substituted or unsubstituted aryl, or substituted or unsubstituted heteroaryl. In a further embodiment, Ar is substituted or unsubstituted aryl. In yet a further embodiment, Ar is phenyl. In another embodiment, Ar is substituted or unsubstituted heteroaryl. In a further embodiment, Ar is indolyl, oxazolyl, furanyl, thienyl, pyrrolyl, pyrazolyl, pyridinyl, pyrazinyl, pyrimidinyl, pyridazinyl, quinazolinyl, quinoxalinyl, quinolinyl, or isoquinolinyl.

In some embodiments is a compound of Formula (IVa) wherein $R_3$ is each independently halogen, —$NH_2$, —$N(CH_3)_2$, substituted or unsubstituted alkyl, substituted or unsubstituted alkoxy, substituted or unsubstituted heteroalkyl, substituted or unsubstituted heterocycloalkyl, or substituted or unsubstituted cycloalkyl. In some embodiments, $R_3$ is substituted or unsubstituted alkyl. In some embodiments, $R_3$ is substituted or unsubstituted cycloalkyl. In some embodiments, $R_3$ is substituted or unsubstituted heterocycloalkyl. In some embodiments, $R_3$ is halogen. In further embodiments, $R_3$ is F, Cl or Br.

In a further embodiment of the aforementioned embodiments is a compound of Formula (IVa), wherein n is 0. In some embodiments of the aforementioned embodiments is a compound of Formula (IVa), wherein n is 1. In some embodiments of the aforementioned embodiments is a compound of Formula (IVa), wherein n is 2. In some embodiments of the aforementioned embodiments is a compound of Formula (IVa), wherein n is 3. In some embodiments of the aforementioned embodiments is a compound of Formula (IVa), wherein n is 4.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of compounds of Formula (I), (Ia), (Ib), (Ic), (Id), (II), (IIa), (III), (IIIa), (IV), and (IVa) include, but are not limited to, compounds selected from the group consisting of:

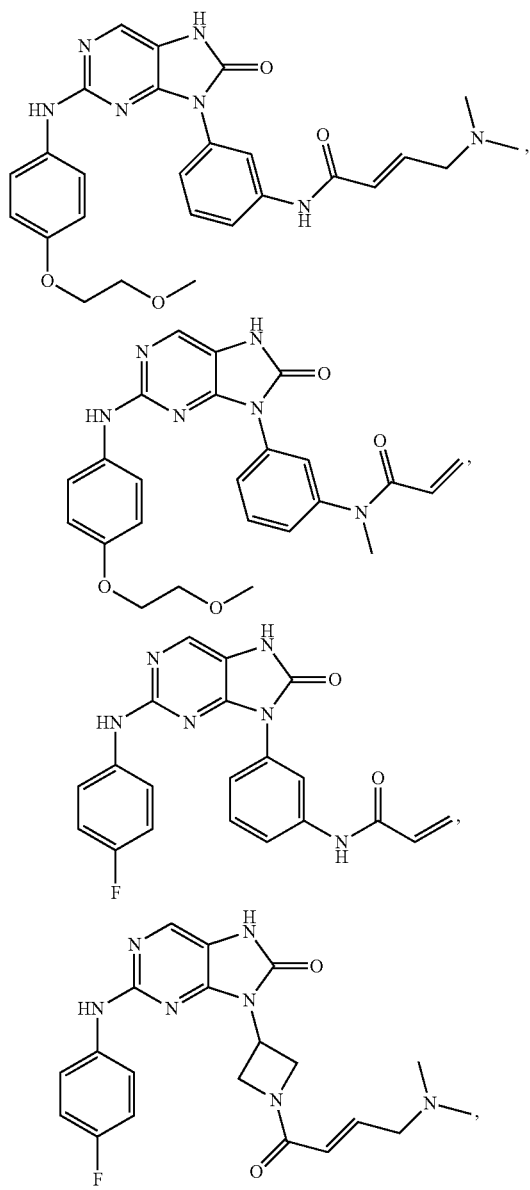

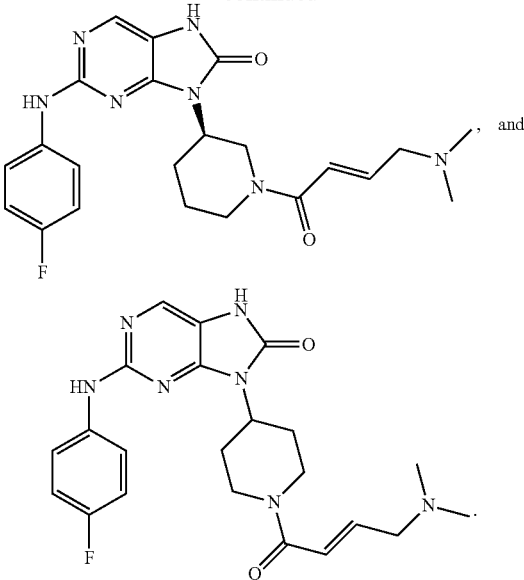

Throughout the specification, groups and substituents thereof can be chosen by one skilled in the field to provide stable moieties and compounds.

In another aspect is a pharmaceutical composition comprising a therapeutically effective amount of a compound of Formula (I), (Ia), (Ib), (Ic), (Id), (II), (IIa), (III), (IIIa), (IV), or (IVa) and a pharmaceutically acceptable excipient. In one embodiment, the pharmaceutical composition comprising the compound of Formula (I), (Ia), (Ib), (Ic), (Id), (II), (IIa), (III), (IIIa), (IV), or (IVa) is formulated for a route of administration selected from oral administration, parenteral administration, buccal administration, nasal administration, topical administration, or rectal administration. In another aspect is a method for treating an autoimmune disease or condition comprising administering to a patient in need a therapeutically effective amount of a compound of Formula (I), (Ia), (Ib), (Ic), (Id), (II), (IIa), (III), (IIIa), (IV), or (IVa). In one embodiment the autoimmune disease is selected from rheumatoid arthritis or lupus. In a further aspect is a method for treating a heteroimmune disease or condition comprising administering to a patient in need a therapeutically effective amount of a compound of Formula (I), (Ia), (Ib), (Ic), (Id), (II), (IIa), (III), (IIIa), (IV), or (IVa). In yet another embodiment is a method for treating a cancer comprising administering to a patient in need a therapeutically effective amount of a compound of Formula (I), (Ia), (Ib), (Ic), (Id), (II), (IIa), (III), (IIIa), (IV), or (IVa). In one embodiment the cancer is a B-cell proliferative disorder.

In another embodiment the B-cell proliferative disorder is diffuse large B cell lymphoma, follicular lymphoma or chronic lymphocytic leukemia.

In yet a further aspect is a method for treating mastocytosis comprising administering to a patient in need a therapeutically effective amount of a compound of Formula (I), (Ia), (Ib), (Ic), (Id), (II), (IIa), (III), (IIIa), (IV), or (IVa).

In another aspect is a method for treating osteoporosis or bone resorption disorders comprising administering to a patient in need a therapeutically effective amount of a compound of Formula (I), (Ia), (Ib), (Ic), (Id), (II), (IIa), (III), (IIIa), (IV), or (IVa).

In a further aspect is a method for treating an inflammatory disease or condition comprising administering to a patient in need a therapeutically effective amount of a compound of Formula (I), (Ia), (Ib), (Ic), (Id), (II), (IIa), (III), (IIIa), (IV), or (IVa).

In some embodiments, the compounds of Formula (I), (Ia), (Ib), (Ic), (Id), (II), (IIa), (III), (IIIa), (IV), and (IVa) reversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

In some embodiments, the compounds of Formula (I), (Ia), (Ib), (Ic), (Id), (II), (IIa), (III), (IIIa), (IV), and (IVa) irreversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

Preparation of Compounds

Compounds of any of Formula (I), (Ia), (Ib), (Ic), (Id), (II), (IIa), (III), (IIIa), (IV), or (IVa) may be synthesized using standard synthetic reactions known to those of skill in the art or using methods known in the art. The reactions can be employed in a linear sequence to provide the compounds or they may be used to synthesize fragments which are subsequently joined by the methods known in the art.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds

Compounds disclosed herein have a structure of Formula (I), (Ia), (Ib), (Ic), (Id), (II), (IIa), (III), (IIIa), (IV), or (IVa). It is understood that when reference is made to compounds described herein, it is meant to include compounds of any of Formula (I), (Ia), (Ib), (Ic), (Id), (II), (IIa), (III), (IIIa), (IV), or (IVa), as well as to all of the specific compounds that fall within the scope of these generic formulae, unless otherwise indicated.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (I), (Ia), (Ib), (Ic), (Id), (II), (IIa), (III), (IIIa), (IV), or (IVa) in unoxidized form can be prepared from N-oxides of compounds of any of Formula (I), (Ia), (Ib), (Ic), (Id), (II), (IIa), (III), (IIIa), (IV), or (IVa) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Sites on the aromatic ring portion of compounds of any of Formula (I), (Ia), (Ib), (Ic), (Id), (II), (IIa), (III), (IIIa), (IV), or (IVa) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (I), (Ia), (Ib), (Ic), (Id), (II), (IIa), (III), (IIIa), (IV), or (IVa), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination"

means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (I), (Ia), (Ib), (Ic), (Id), (II), (IIa), (III), (IIIa), (IV), or (IVa), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (I) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula (I), (Ia), (Ib), (Ic), (Id), (II), (IIa), (III), (IIIa), (IV), or (IVa), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (I), (Ia), (Ib), (Ic), (Id), (II), (IIa), (III), (IIIa), (IV), or (IVa) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (I), (Ia), (Ib), (Ic), (Id), (II), (IIa), (III), (IIIa), (IV), or (IVa), with one or more pharmaceutical excipients to form a bulk blend composition. When referring to these bulk blend compositions as homogeneous, it is meant that the particles of the compound of any of Formula (I), (Ia), (Ib), (Ic), (Id), (II), (IIa), (III), (IIIa), (IV), or (IVa), are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (I), (Ia), (Ib), (Ic), (Id), (II), (IIa), (III), (IIIa), (IV), or (IVa). In one embodiment, some or all of the particles of the compound of any of Formula (I), (Ia), (Ib), (Ic), (Id), (II), (IIa), (III), (IIIa), (IV), or (IVa), are coated. In another embodiment, some or all of the particles of the compound of any of Formula (I), (Ia), (Ib), (Ic), (Id), (II), (IIa), (III), (IIIa), (IV), or (IVa), are microencapsulated. In still another embodiment, the particles of the compound of any of Formula (I), (Ia), (Ib), (Ic), (Id), (II), (IIa), (III), (IIIa), (IV), or (IVa), are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (I), (Ia), (Ib), (Ic), (Id), (II), (IIa), (III), (IIIa), (IV), or (IVa), from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of of any of Formula (I), (Ia), (Ib), (Ic), (Id), (II), (IIa), (III), (IIIa), (IV), or (IVa), from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula (I), (Ia), (Ib), (Ic), (Id), (II), (IIa), (III), (IIIa), (IV), or (IVa), described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (I), (Ia), (Ib), (Ic), (Id), (II), (IIa), (III), (IIIa), (IV), or (IVa), and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (I), (Ia), (Ib), (Ic), (Id), (II), (IIa), (III), (IIIa), (IV), or (IVa), which sufficiently isolate the compound of any of Formula (I), (Ia), (Ib), (Ic), (Id), (II), (IIa), (III), (IIIa), (IV), or (IVa), from other non-compatible excipients. Materials compatible with compounds of any of Formula (I), (Ia), (Ib), (Ic), (Id), (II), (IIa), (III), (IIIa), (IV), or (IVa), are those that delay the release of the compounds of of any of Formula (I), (Ia), (Ib), (Ic), (Id), (II), (IIa), (III), (IIIa), (IV), or (IVa), in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula (I), (Ia), (Ib), (Ic), (Id), (II), (IIa), (III), (IIIa), (IV), or (IVa), may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of Formula (I), (Ia), (Ib), (Ic), (Id), (II), (IIa), (III), (IIIa), (IV), or (IVa), are microencapsulated prior to being formulated into one of the above forms. In still another embodiment, some or most of the particles are coated prior to being further formulated by using standard coating procedures, such as those described in *Remington's Pharmaceutical Sciences*, 20th Edition (2000).

In other embodiments, the solid dosage formulations of the compounds of any of Formula (I), (Ia), (Ib), (Ic), (Id), (II), (IIa), (III), (IIIa), (IV), or (IVa), are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula (I), (Ia), (Ib), (Ic), (Id), (II), (IIa), (III), (IIIa), (IV), or (IVa), described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound of Formula (A), are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms including formulations described herein, which include a compound of any of Formula (I), (Ia), (Ib), (Ic), (Id), (II), (IIa), (III), (IIIa), (IV), or (IVa), can be further formulated to provide a controlled release of the compound of Formula (A). Controlled release refers to the release of the compound of any of Formula (I), (Ia), (Ib), (Ic), (Id), (II), (IIa), (III), (IIIa), (IV), or (IVa), from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (A), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (I), (Ia), (Ib), (Ic), (Id), (II), (IIa), (III), (IIIa), (IV), or (IVa), may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form including at least two groups of particles, (i.e. multiparticulate) each containing the formulation described herein. The first group of particles provides a substantially immediate dose of the compound of any of Formula (I), (Ia), (Ib), (Ic), (Id), (II), (IIa), (III), (IIIa), (IV), or (IVa), upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (I), (Ia), (Ib), (Ic), (Id), (II), (IIa), (III), (IIIa), (IV), or (IVa), in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (I).

Many other types of controlled release systems known to those of ordinary skill in the art and are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds of any of Formula (I), (Ia), (Ib), (Ic), (Id), (II), (IIa), (III), (IIIa), (IV), or (IVa), described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compound of Formula (A), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include a compound of any of Formula (I), (Ia), (Ib), (Ic), (Id), (II), (IIa), (III), (IIIa), (IV), or (IVa), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (I), (Ia), (Ib), (Ic), (Id), (II), (IIa), (III), (IIIa), (IV), or (IVa), described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula (I), (Ia), (Ib), (Ic), (Id), (II), (IIa), (III), (IIIa), (IV), or (IVa), may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (I), (Ia), (Ib), (Ic), (Id), (II), (IIa), (III), (IIIa), (IV), or (IVa), is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (I), (Ia), (Ib), (Ic), (Id), (II), (IIa), (III), (IIIa), (IV), or (IVa), and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of any of Formula (I); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (I), (Ia), (Ib), (Ic), (Id), (II), (IIa), (III), (IIIa), (IV), or (IVa). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula (I), (Ia), (Ib), (Ic), (Id), (II), (IIa), (III), (IIIa), (IV), or (IVa), suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the inhibition of Btk or a homolog thereof, or for the treatment of diseases or conditions that would benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (I), (Ia), (Ib), (Ic), (Id), (II), (IIa), (III), (IIIa), (IV), or (IVa), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The reversible or irreversible Btk inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one reversible or irreversible Btk inhibitor compound described herein in combination with another therapeutic agent. By way of example only, if one of the side effects experienced by a patient upon receiving one of the reversible or irreversible Btk inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), (Ia), (Ib), (Ic), (Id), (II), (IIa), (III), (IIIa), (IV), or (IVa) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with a Reversible or Irreversible Btk Inhibitor Compound Where the subject is suffering from or at risk of suffering from an autoimmune disease, an inflammatory disease, or an allergy disease, a reversible or irreversible Btk inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subjected can be treated with a reversible or irreversible Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a reversible or irreversible Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a reversible or irreversible Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a reversible or irreversible Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816;

crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; Rh retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a reversible or irreversible Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomustine, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a reversible or irreversible Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a reversible or irreversible Btk inhibitor compound include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a reversible or irreversible Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a reversible or irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a reversible or irreversible Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Btk, or in which Btk is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Synthesis of (E)-4-(dimethylamino)-N-(3-(2-(4-(2-methoxyethoxy)phenylamino)-8-oxo-7H-purin-9(8H)-yl)phenyl)but-2-enamide (6)

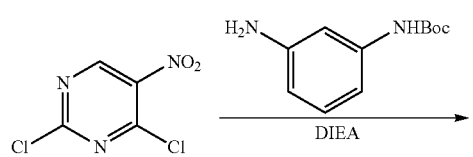

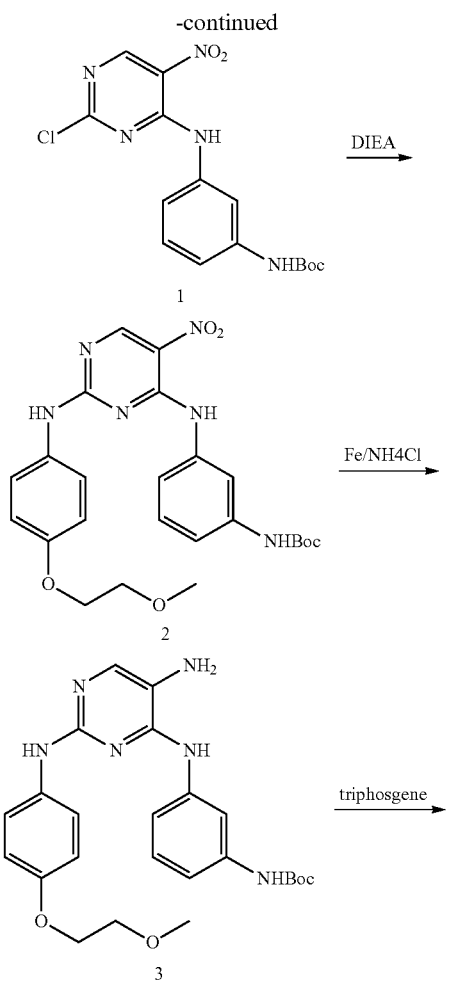

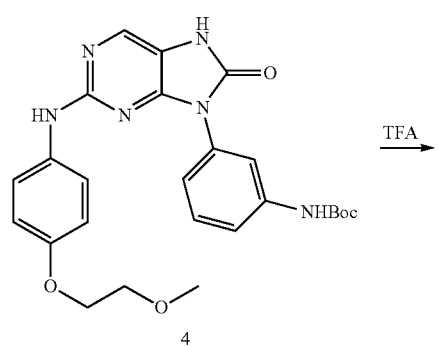

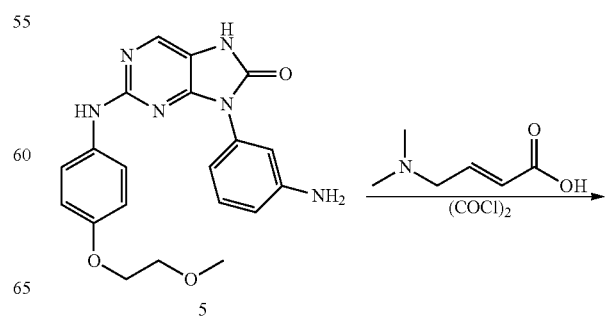

-continued

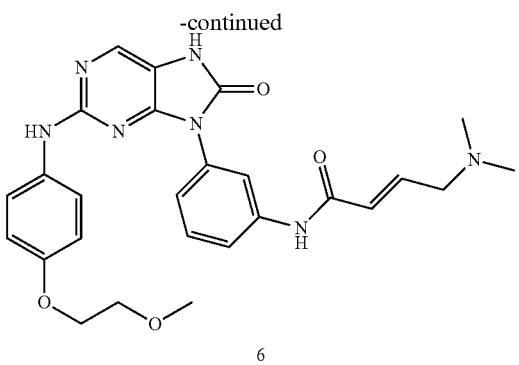

6

To a solution of 2,4-dichloro-5-nitropyrimidine (582 mg, 3 mmol) in THF (5 mL) was added DIEA (775 mg, 6 mmol) and tert-butyl 3-aminophenylcarbamate (625 mg, 3 mmol, in 2 mL THF) at −78° C. under $N_2$ atmosphere. After stirring at −78° C. for 30 min, the reaction was warmed up to r. t. and stirred overnight. The reaction was quenched with water (10 mL) and extracted with IPA/DCM (15:85) (5 mL×3). The combined organic layer was washed with brine, and dried over $Na_2SO_4$. The solvents were removed under vacuum and the residue was purified by flash chromatography (silica gel, 0 to 5% ethyl acetate in PE/DCM (1/1) with 0.5% TEA) to provide tert-butyl 3-(2-chloro-5-nitropyrimidin-4-ylamino)phenylcarbamate (1) (1.087 g, 99%) as an orange solid. LC-MS (ESI) m/z (M/M+2) 366.2/368.2.

To a solution of tert-butyl 3-(2-chloro-5-nitropyrimidin-4-ylamino)phenylcarbamate (1) (430 mg, 1.37 mmol) in THF (10 mL) was added DIEA (530 mg, 4.1 mmol) and 4-(2-methoxyethoxy)aniline (39) (274 mg, 1.64 mmol) at r.t. under $N_2$ atmosphere. The resulting mixture was stirred at r.t. overnight. The solvent was removed and the residue was purified by flash column chromatography (silica gel, 0 to 5% ethyl acetate in PE/DCM (1/1), with 0.5% TEA) to provide tert-butyl 3-(2-(4-(2-methoxyethoxyl)phenylamino)-5-nitropyrimidin-4-ylamino)phenylcarbamate (2) (559 mg, 96%) as a yellow solid. LC-MS (ESI) m/z (M+1) 497.1.

A suspension of tert-butyl 3-(2-(4-(2-methoxyethoxyl)phenylamino)-5-nitropyrimidin-4-ylamino)phenylcarbamate (2) (559 mg, 1.13 mmol), Fe powder (629 mg, 11.26 mmol) and $NH_4Cl$ (1.205 g, 22.52 mmol) in THF/MeOH/$H_2O$ (30 mL/15 mL/8 mL) was stirred at 50° C. for one hour under $N_2$ atmosphere. The reaction mixture was then filtered through a pad of celite and the solvents were removed under reduced pressure. The crude product was purified by column chromatography (silica gel, 0 to 50% MeOH in DCM/MeOH with 0.5% TEA) to provide tert-butyl 3-(5-amino-2-(4-(2-methoxyethoxyl)phenylamino)pyrimidin-4-ylamino)phenylcarbamate (3) (405 mg, 77%) as a solid. LC-MS (ESI) m/z (M+1) 467.1.

At 0° C. under $N_2$ atmosphere, to a solution of tert-butyl 3-(5-amino-2-(4-(2-methoxyethoxyl)phenylamino)pyrimidin-4-ylamino)phenylcarbamate (3) (405 mg, 0.868 mmol) and TEA (264 mg, 2.605 mmol) in DCM (20 mL) was added a solution of triphosgene (129 mg, 0.434 mmol) in 5 mL of DCM dropwise. The resulting mixture was stirred at 0° C. for one hour before quenched with saturated aqueous $NaHCO_3$. The reaction mixture was extracted with DCM. The combined organic extract was dried over $Na_2SO_4$, filtered and concentrated in vacuo. The crude product was purified by column chromatography (silica gel, 5 to 9% MeOH in DCM, with 0.5% TEA) to provide tert-butyl 3-(2-(4-(2-methoxyeth-oxy)phenylamino)-8-oxo-7H-purin-9(8H)-yl)phenylcarbamate (4) (312 mg, 73%) as a solid. LC-MS (ESI) m/z (M+1) 493.2.

To a solution of tert-butyl 3-(2-(4-(2-methoxyethoxyl)phenylamino)-8-oxo-7H-purin-9(8H)-yl)phenylcarbamate (4) (312 mg, 0.633 mmol) in DCM (5 mL) was added TFA (5 mL). The resulting mixture was stirred at r.t. for one hour. Excess TFA was removed under vacuum and neutralized by saturated aqueous $NaHCO_3$. The product was extracted with IPA/DCM (15:85) (5 mL×3). The combined organic layer was dried over $Na_2SO_4$ and concentrated to afford 9-(3-aminophenyl)-2-(4-(2-methoxyethoxyl)phenylamino)-7H-purin-8(9H)-one (5) (221 mg, 89%) as a white solid. LC-MS (ESI) m/z (M+1) 393.1.

(E)-4-(dimethylamino)-N-(3-(2-(4-(2-methoxyethoxyl)phenylamino)-8-oxo-7H-purin-9(8H)-yl)phenyl)but-2-enamide (6) (20 mg, 7%) was obtained as a white solid from 9-(3-aminophenyl)-2-(4-(2-methoxyethoxyl)phenylamino)-7H-purin-8(9H)-one (5) (221 mg) and (E)-4-(dimethylamino)but-2-enoic acid HCl salt (112 mg) under standard conditions. LC-MS (ESI) m/z (M+1) 504.2. $^1$H NMR (400 MHz, DMSO) δ 11.14 (br, 1H), 10.28 (s, 1H), 9.11 (s, 1H), 8.01 (s, 1H), 7.97 (s, 1H), 7.67 (d, J=7.9 Hz, 1H), 7.60-7.54 (m, 2H), 7.49-7.43 (m, 1H), 7.35-7.23 (m, 1H), 6.80-6.67 (m, 3H), 6.29 (d, J=15.5 Hz, 1H), 4.02-3.92 (m, 2H), 3.62-3.56 (m, 2H), 3.28 (s, 3H), 3.05 (d, J=5.5 Hz, 2H), 2.16 (s, 6H).

Example 2

Synthesis of N-(3-(2-(4-(2-methoxyethoxyl)phenylamino)-8-oxo-7H-purin-9(8H)-yl)phenyl)-N-methylacrylamide (13)

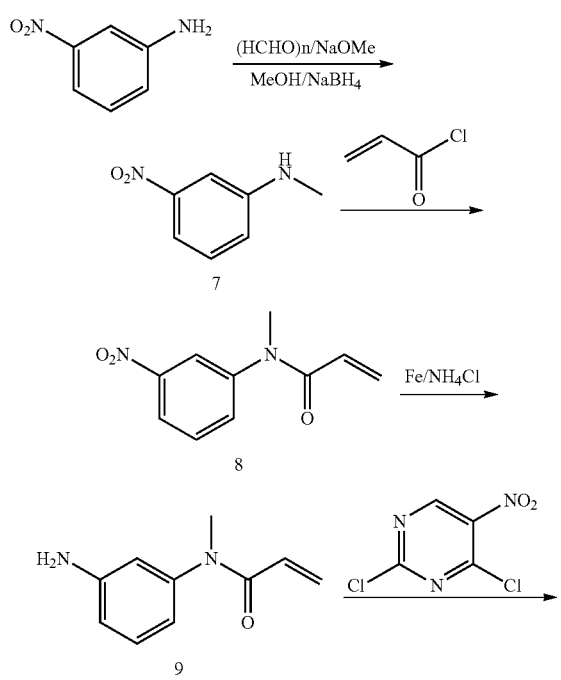

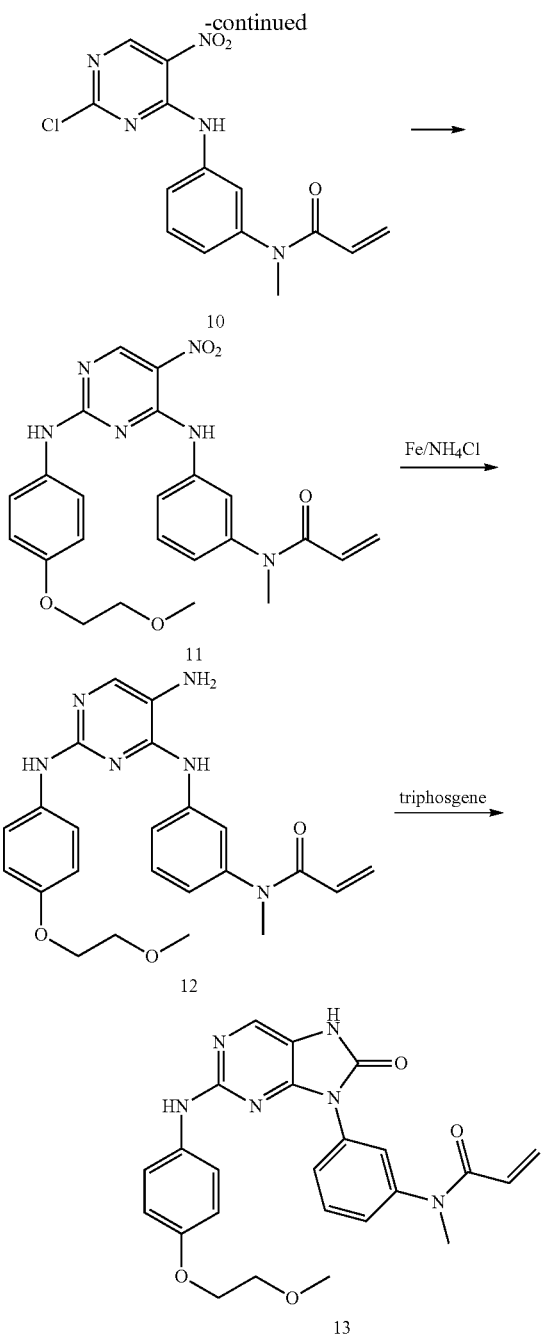

To a solution of 3-nitroaniline (2.07 g, 15 mmol) and (HCHO)$_n$ (675 mg) in MeOH (50 mL) was added NaOMe (4.05 g, 75 mmol) uner N$_2$ atmosphere. The resulting suspension was stirred at r.t. for 3 hrs before introducing NaBH$_4$ (570 mg, 15 mmol). The reaction mixture was then heated to reflux for 3 hrs. The solvent was removed under vacuum and the residue was partitioned between EA (100 mL) and water (100 mL). The layers were separated, the organic layer was dried over Na$_2$SO$_4$ and concentrated in vacuo. The residue was purified by column chromatography (silica gel, 0 to 10% ethyl acetate in petroleum ether) to provide N-methyl-3-nitroaniline (7) (2.11 g, 92%) as a white solid.

At 0° C., to a solution of N-methyl-3-nitroaniline (7) (2.11 g, 13.87 mmol) and TEA (4.21 g, 41.60 mmol) in DCM (50 mL) was added acryloyl chloride (1.51 g, 16.64 mmol). The resulting mixture was stirred at r.t. overnight and was then quenched with water (20 mL). The product was extracted with DCM (10 mL×2). The combined organic layer was washed with brine, dried over Na$_2$SO$_4$ and purified by column chromatography (silica gel, 0 to 35% ethyl acetate in petroleum ether) to provide N-methyl-N-(3-nitrophenyl)acrylamide (8) (1.809 g, 63%) as an oil. LC-MS (ESI) m/z (M+1) 207.1.

To a solution of N-methyl-N-(3-nitrophenyl)acrylamide (8) (1.81 g, 8.77 mmol) in THF/MeOH/H$_2$O (30 mL/15 mL/8 mL) was added Fe powder (4.90 g, 87.73 mmol) and NH$_4$Cl (9.385 g, 175.46 mmol). The resulting suspension was stirred at 80° C. for 2 hr then filtered through a pad of celite. The solvents were removed under reduced pressure and the residue was purified by column chromatography (silica gel, 1 to 60% ethyl acetate in petroleum ether, with 0.5% TEA) to afford N-(3-aminophenyl)-N-methylacrylamide (9) (1.236 g, 80%) as a yellow oil. LC-MS (ESI) m/z (M+1) 177.2.

N-(3-(2-Chloro-5-nitropyrimidin-4-ylamino)phenyl)-N-methylacrylamide (10) (396 mg, 59%) was obtained as a yellow solid from N-(3-aminophenyl)-N-methylacrylamide (9) (352 mg, 2 mmol) and 2,4-dichloro-5-nitropyrimidine (388 mg, 2 mmol) following a similar procedure outlined in Example 1. LC-MS (ESI) m/z (M/M+2) 334.0/336.0.

To a solution of N-(3-(2-chloro-5-nitropyrimidin-4-ylamino)phenyl)-N-methylacryl amide (396 mg, 1.19 mmol) and 4-(2-methoxyethoxy)aniline (39) (218 mg, 1.42 mmol) in n-BuOH (5 mL) was added 2 drops of conc. HCl. The resulting mixture was heated to 120° C. for 2 hrs in a microwave reactor. The solvents were removed and the residue was purified by flash chromatography (silica gel, 0 to 70% ethyl acetate in petroleum, with 0.5% TEA) to provide N-(3-(2-(4-(2-methoxyethoxyl)phenylamino)-5-nitropyrimidin-4-ylamino)phenyl)-N-methylacrylamide (11) (221 mg, 41%) as a yellow solid. LC-MS (ESI) m/z (M+1) 465.1.

N-(3-(5-Amino-2-(4-(2-methoxyethoxyl)phenylamino)pyrimidin-4-ylamino)phenyl)-N-methylacrylamide (12) (quant. yield) was obtained as a brown solid from N-(3-(2-(4-(2-methoxyethoxyl)phenylamino)-5-nitropyrimidin-4-ylamino)phenyl)-N-methylacrylamide (11) (221 mg), following a similar procedure outlined in Example 1. LC-MS (ESI) m/z (M+1) 435.0.

N-(3-(2-(4-(2-Methoxyethoxyl)phenylamino)-8-oxo-7H-purin-9(8H)-yl)phenyl)-N-methylacrylamide (13) was obtained as a white solid (32 mg, 14%) from N-(3-(5-amino-2-(4-(2-methoxyethoxyl)phenylamino)pyrimidin-4-ylamino)phenyl)-N-methylacrylamide (12) (221 mg) following a similar procedure outlined in Example 1. LC-MS (ESI) m/z (M+1) 461.1. $^1$H NMR (400 MHz, DMSO) δ 11.23 (s, 1H), 9.12 (s, 1H), 8.02 (s, 1H), 7.73-7.66 (m, 2H), 7.61 (t, J=7.9 Hz, 1H), 7.53 (d, J=9.0 Hz, 2H), 7.33 (d, J=7.8 Hz, 1H), 6.77 (d, J=9.1 Hz, 1H), 6.19 (s, 2H), 5.65-5.54 (m, 1H), 4.02-3.95 (m, 2H), 3.63-3.59 (m, 2H), 3.34-3.25 (m, 6H).

Example 3

Synthesis of N-(3-(2-(4-fluorophenylamino)-8-oxo-7H-purin-9(8H)-yl)phenyl)acrylamide (17)

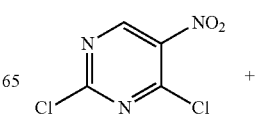

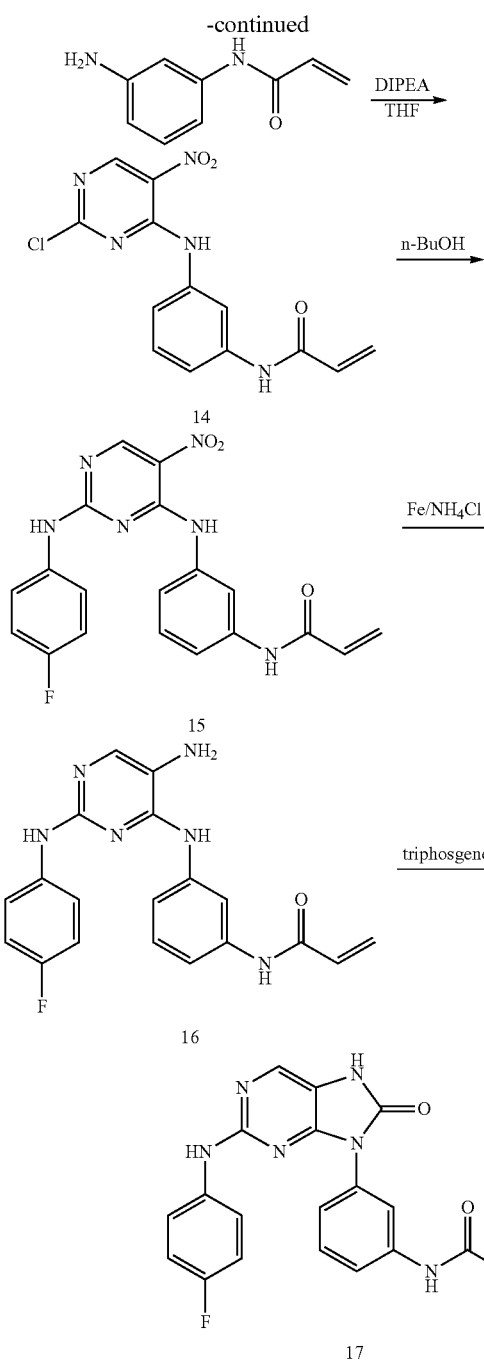

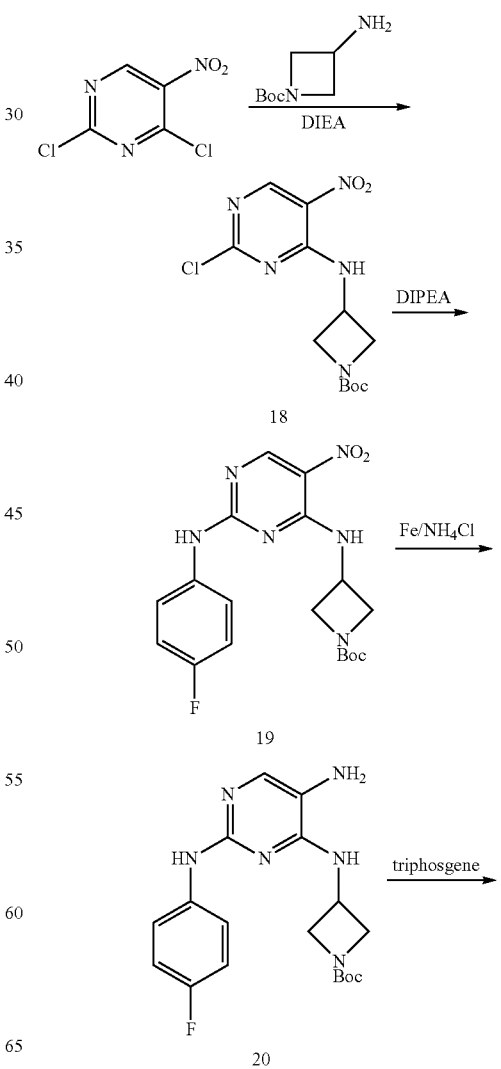

as a yellow solid from N-(3-(2-(4-fluorophenylamino)-5-nitropyrimidin-4-ylamino)phenyl)acrylamide (15) (174 mg, 0.441 mmol), following a similar procedure outlined in Example 2. LC-MS (ESI) m/z (M+1) 365.1.

N-(3-(2-(4-Fluorophenylamino)-8-oxo-7H-purin-9(8H)-yl)phenyl)acrylamide (17) (7 mg, 12%) was obtained as a white solid from N-(3-(5-amino-2-(4-fluorophenylamino)pyrimidin-4-ylamino)phenyl)acrylamide (16) (52 mg, 0.143 mmol) following a similar procedure outlined in Example 2. LC-MS (ESI) m/z (M+1) 391.1. $^1$H NMR (400 MHz, DMSO) δ 11.22 (s, 1H), 10.36 (s, 1H), 9.35 (s, 1H), 8.04 (s, 1H), 7.96 (s, 1H), 7.73-7.66 (m, 3H), 7.53-7.46 (m, 1H), 7.36-7.30 (m, 1H), 7.02-6.96 (m, 2H), 6.50-6.42 (m, 1H), 6.30-6.23 (m, 1H), 5.80-5.76 (m, 1H).

Example 4

Synthesis of (E)-9-(1-(4-(dimethylamino)but-2-enoyl)azetidin-3-yl)-2-(4-fluorophenylamino)-7H-purin-8(9H)-one (23)

N-(3-(2-Chloro-5-nitropyrimidin-4-ylamino)phenyl)acrylamide (14) (240 mg, 75%) was obtained as a red solid from 2,4-dichloro-5-nitropyrimidine (194 mg, 1 mmol) and N-(3-aminophenyl)acrylamide (162 mg, 1 mmol), following a similar procedure outlined in Example 1. LC-MS (ESI) m/z (M/M+2) 320.0/322.0.

N-(3-(2-(4-Fluorophenylamino)-5-nitropyrimidin-4-ylamino)phenyl)acrylamide (15) (174 mg, 59%) was obtained as a yellow solid from N-(3-(2-chloro-5-nitropyrimidin-4-ylamino)phenyl)acrylamide (14) (240 mg, 0.751 mmol) and 4-fluoroaniline (100 mg, 0.901 mmol), following a similar procedure outlined in Example 2. LC-MS (ESI) m/z (M+1) 395.0.

N-(3-(5-Amino-2-(4-fluorophenylamino)pyrimidin-4-ylamino)phenyl)acrylamide (16) (52 mg, 32%) was obtained

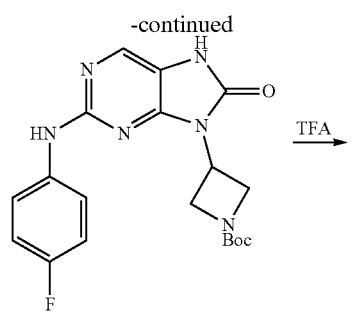

21

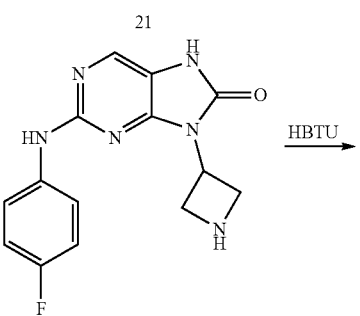

22

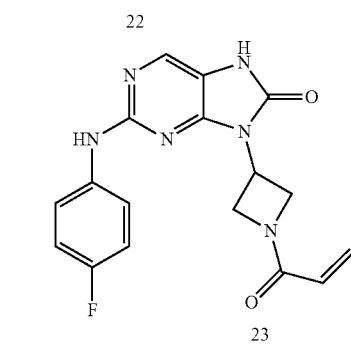

23 tert-Butyl 3-(2-chloro-5-nitropyrimidin-4-ylamino)azetidine-1-carboxylate (18) (758 mg, 77%) was obtained from 2,4-dichloro-5-nitropyrimidine (582 mg, 3 mmol) and tert-butyl 3-aminoazetidine-1-carboxylate (516 mg, 3 mmol), following a similar procedure outlined in Example 1.

tert-Butyl 3-(2-(4-fluorophenylamino)-5-nitropyrimidin-4-ylamino)azetidine-1-carboxylate (19) (579 mg, 62%) was obtained from tert-butyl 3-(2-chloro-5-nitropyrimidin-4-ylamino)azetidine-1-carboxylate (18) (758 mg, 2.3 mmol) and 4-fluoroaniline (306 mg, 2.75 mmol), following a similar procedure outlined in Example 1. LC-MS (ESI): m/z (M+1) 405.1.

tert-Butyl 3-(5-amino-2-(4-fluorophenylamino)pyrimidin-4-ylamino)azetidine-1-carboxylate (20) (536 mg, quant. yield) was obtained from tert-butyl 3-(2-(4-fluorophenylamino)-5-nitropyrimidin-4-ylamino)azetidine-1-carboxylate (19) (579 mg, 1.43 mmol), following a similar procedure outlined in Example 1. LC-MS (ESI): m/z (M+1) 375.1.

tert-Butyl 3-(2-(4-fluorophenylamino)-8-oxo-7H-purin-9(8H)-yl)azetidine-1-carboxylate (21) (400 mg, 70%) was obtained from tert-butyl 3-(5-amino-2-(4-fluorophenylamino)pyrimidin-4-ylamino)azetidine-1-carboxylate (20) (536 mg, 1.429 mmol), following a similar procedure outlined in Example 1. LC-MS (ESI): m/z (M+1) 401.1.

9-(Azetidin-3-yl)-2-(4-fluorophenylamino)-7H-purin-8(9H)-one (22) (300 mg, quant. yield) was obtained from tert-butyl 3-(2-(4-fluorophenylamino)-8-oxo-7H-purin-9(8H)-yl)azetidine-1-carboxylate (21) (400 mg), following a similar procedure outlined in Example 1. LC-MS (ESI): m/z (M+1) 301.1.

(E)-9-(1-(4-(Dimethylamino)but-2-enoyl)azetidin-3-yl)-2-(4-fluorophenylamino)-7H-purin-8(9H)-one (23) (13 mg, 3%) was obtained as a white solid from tert-butyl 9-(azetidin-3-yl)-2-(4-fluorophenylamino)-7H-purin-8(9H)-one (300 mg, 1.00 mmol) (22) and (E)-4-(dimethylamino)but-2-enoic acid HCl salt (181.5 mg, 1.09 mmol) following standard conditions. LC-MS (ESI): m/z (M+1) 412.3. $^1$H NMR (400 MHz, DMSO) δ 9.39 (s, 1H), 8.23 (s, 1H), 7.99 (s, 1H), 7.67 (dd, J=9.2, 4.9 Hz, 2H), 6.96 (t, J=8.9 Hz, 2H), 6.74-6.58 (m, 1H), 6.15 (d, J=15.4 Hz, 1H), 5.31-5.18 (m, 1H), 4.85-4.76 (m, 1H), 4.67-4.50 (m, 2H), 4.34-4.23 (m, 1H), 3.07-2.98 (m, 2H), 2.10 (s, 6H).

Example 5

Synthesis of (R,E)-9-(1-(4-(dimethylamino)but-2-enoyl)piperidin-3-yl)-2-(4-fluorophenylamino)-7H-purin-8(9H)-one (29)

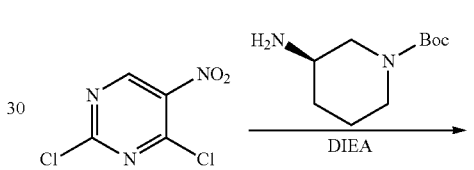

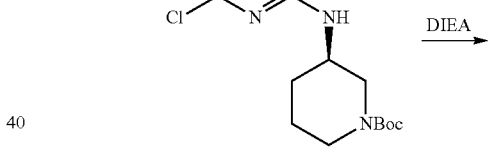

24

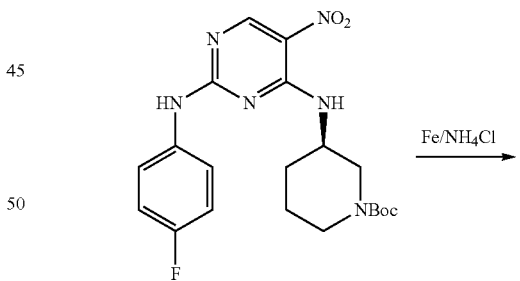

25

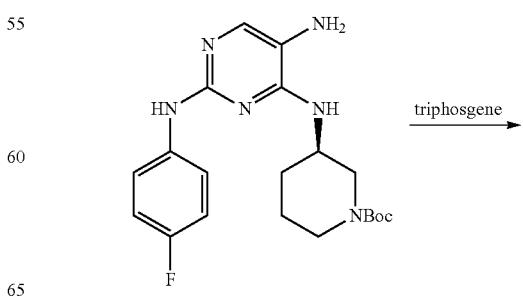

26

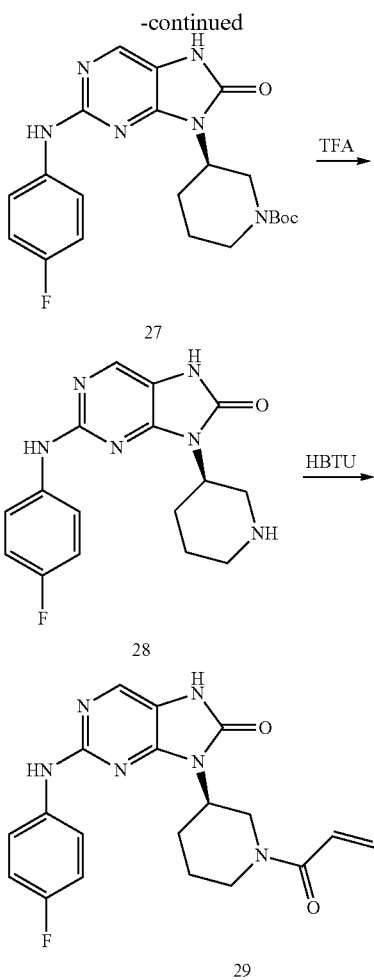

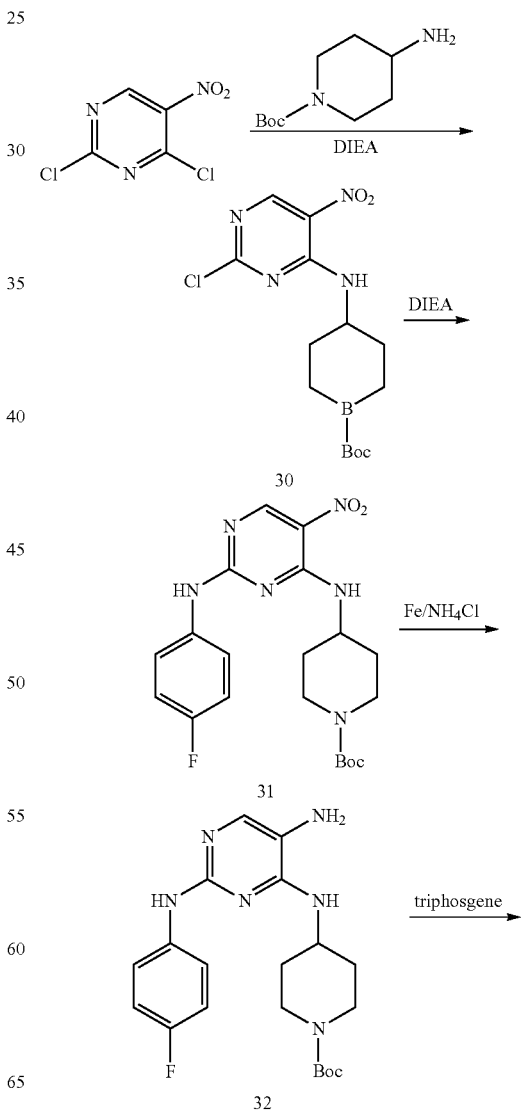

(R)-tert-Butyl 3-(2-chloro-5-nitropyrimidin-4-ylamino)piperidine-1-carboxylate (24) (480 mg, 62%) was obtained from 2,4-dichloro-5-nitropyrimidine (388 mg, 2 mmol) and (R)-tert-butyl 3-aminopiperidine-1-carboxylate (400 mg, 2 mmol), following a procedure outlined in Example 1. LC-MS (ESI): m/z (M/M+2) 357.0/359.0.

(R)-tert-Butyl 3-(2-(4-fluorophenylamino)-5-nitropyrimidin-4-ylamino)piperidine-1-carboxylate (25) (290 mg, quant. yield) was obtained from (R)-tert-butyl 3-(2-chloro-5-nitropyrimidin-4-ylamino)piperidine-1-carboxylate (24) (240 mg, 0.67 mmol) and 4-fluoroaniline (89.6 mg, 0.806 mmol), following a similar procedure outlined in Example 1. LC-MS (ESI): m/z (M+1) 433.2.

(R)-tert-Butyl 3-(5-amino-2-(4-fluorophenylamino)pyrimidin-4-ylamino)piperidine-1-carboxylate (26) (230 mg, 83%) was obtained from (R)-tert-butyl 3-(2-(4-fluorophenylamino)-5-nitropyrimidin-4-ylamino)piperidine-1-carboxylate (25) (300 mg, 0.69 mmol), following a similar procedure outlined in Example 1. LC-MS (ESI): m/z (M+1) 403.2.

(R)-tert-Butyl 3-(2-(4-fluorophenylamino)-8-oxo-7H-purin-9(8H)-yl)piperidine-1-carboxylate (27) (150 mg, 61%) was obtained from (R)-tert-butyl 3-(5-amino-2-(4-fluorophenylamino)pyrimidin-4-ylamino)piperidine-1-carboxylate (26) (230 mg, 0.57 mmol), following a similar procedure outlined in Example 1. LC-MS (ESI): m/z (M−1) 427.0.

(R)-2-(4-Fluorophenylamino)-9-(piperidin-3-yl)-7H-purin-8(9H)-one (28) (60 mg, 53%) was obtained from (R)-tert-butyl 3-(2-(4-fluorophenylamino)-8-oxo-7H-purin-9(8H)-yl)piperidine-1-carboxylate (27) (150 mg), following a similar procedure outlined in Example 1. LC-MS (ESI): m/z (M+1) 329.0.

(R,E)-9-(1-(4-(Dimethylamino)but-2-enoyl)piperidin-3-yl)-2-(4-fluorophenylamino)-7H-purin-8(9H)-one (29) (6.5 mg, 8%) was obtained as a white solid from (R)-2-(4-fluorophenylamino)-9-(piperidin-3-yl)-7H-purin-8(9H)-one (28) (60 mg, 0.183 mmol) and (E)-4-(dimethylamino)but-2-enoic acid HCl salt (33.1 mg, 0.2 mmol) following standard conditions. LC-MS (ESI): m/z (M+1) 440.4. $^1$H NMR (400 MHz, DMSO) δ 10.99 (s, 1H), 9.29 (s, 1H), 7.94 (s, 1H), 7.76-7.67 (m, 2H), 7.07 (t, J=9.0 Hz, 2H), 6.61 (s, 2H), 4.59-4.43 (m, 1H), 4.20-4.04 (m, 2H), 3.40-3.32 (m, 1H), 3.06-2.94 (m, 3H), 2.58-2.51 (m, 1H), 2.15-2.07 (m, 6H), 1.93-1.83 (m, 2H), 1.54-1.39 (m, 1H).

Example 6

Synthesis of (E)-9-(1-(4-(dimethylamino)but-2-enoyl)piperidin-4-yl)-2-(4-fluorophenylamino)-7H-purin-8(9H)-one (35)

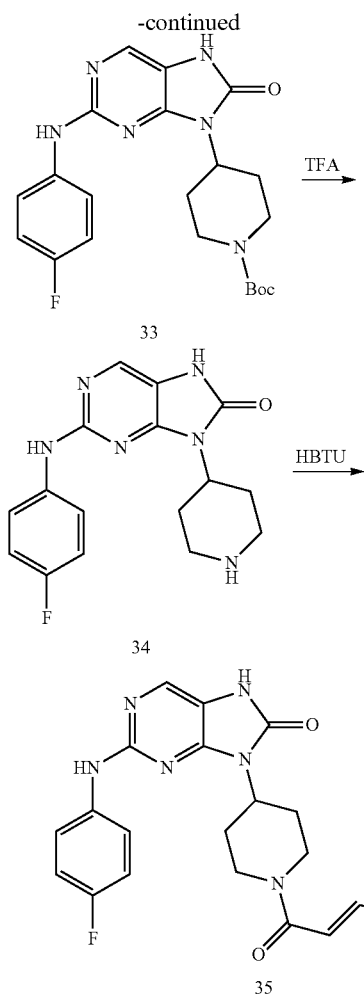

dine-1-carboxylate (33) (106 mg, 0.25 mmol), following a similar procedure outlined in Example 1. LC-MS (ESI): m/z (M+1) 329.2.

(E)-9-(1-(4-(Dimethylamino)but-2-enoyl)piperidin-4-yl)-2-(4-fluorophenylamino)-7H-purin-8(9H)-one (35) (13 mg, 12%) was obtained as a white solid from 2-(4-fluorophenylamino)-9-(piperidin-4-yl)-7H-purin-8(9H)-one (34) (82 mg, 0.25 mmol) and (E)-4-(dimeth-ylamino)but-2-enoic acid HCl salt (45 mg, 0.27 mmol) following standard conditions. LC-MS (ESI): m/z (M+1) 440.4. $^1$H NMR (400 MHz, DMSO) δ 10.98 (s, 1H), 9.32 (s, 1H), 7.93 (s, 1H), 7.67 (dd, J=9.1, 4.9 Hz, 2H), 7.02 (t, J=8.9 Hz, 2H), 6.75-6.61 (m, 2H), 4.68-4.17 (m, 3H), 3.14-3.09 (m, 3H), 2.77-2.69 (m, 1H), 2.42-2.33 (m, 2H), 2.19 (s, 6H), 1.82-1.75 (m, 2H).

Example 7

Synthesis of N-(3-(2-(4-(2-methoxyethoxy)phenylamino)-8-oxo-7H-purin-9(8H)-yl)phenyl)acrylamide (43)

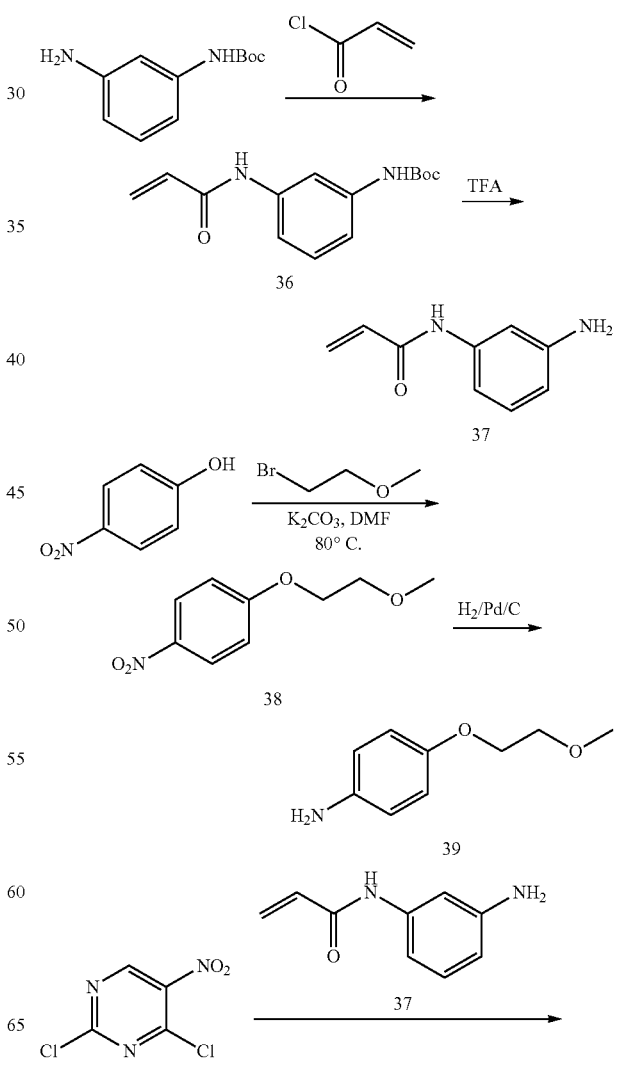

tert-Butyl 4-(2-chloro-5-nitropyrimidin-4-ylamino)piperidine-1-carboxylate (30) (500 mg, 68%) was obtained from 2,4-dichloro-5-nitropyrimidine (500 mg, 2.58 mmol) and tert-butyl 4-aminopiperidine-1-carboxylate (435 mg, 2.06 mmol), following a similar procedure outlined in Example 1. LC-MS (ESI): m/z (M/M+2) 358.1/360.1.

tert-Butyl 4-(2-(4-fluorophenylamino)-5-nitropyrimidin-4-ylamino)piperidine-1-carboxylate (31) (900 mg, 93%) was obtained from tert-butyl 4-(2-chloro-5-nitropyrimidin-4-ylamino)piperidine-1-carboxylate (30) (800 mg, 2.24 mmol) and 4-fluoroaniline (298 mg, 2.68 mmol), following a similar procedure outlined in Example 1. LC-MS (ESI): m/z (M+1) 433.2.

tert-Butyl 4-(5-amino-2-(4-fluorophenylamino)pyrimidin-4-ylamino)piperidine-1-carboxylate (32) (500 mg, 60%) was obtained from tert-butyl 4-(2-(4-fluorophenylamino)-5-nitropyrimidin-4-ylamino)piperidine-1-carboxylate (31) (900 mg, 2.08 mmol), following a similar procedure outlined in Example 1. LC-MS (ESI): m/z (M+1) 403.2.

tert-Butyl 4-(2-(4-fluorophenylamino)-8-oxo-7H-purin-9(8H)-yl)piperidine-1-carboxylate (33) (106 mg, 20%) was obtained from tert-butyl 4-(5-amino-2-(4-fluorophenylamino)pyrimidin-4-ylamino)piperidine-1-carboxylate (32) (500 mg, 1.24 mmol), following a similar procedure outlined in Example 1. LC-MS (ESI): m/z (M+1) 429.3.

2-(4-Fluorophenylamino)-9-(piperidin-4-yl)-7H-purin-8(9H)-one (34) (quant.) was obtained from tert-butyl 4-(2-(4-fluorophenylamino)-8-oxo-7H-purin-9(8H)-yl) piperi-

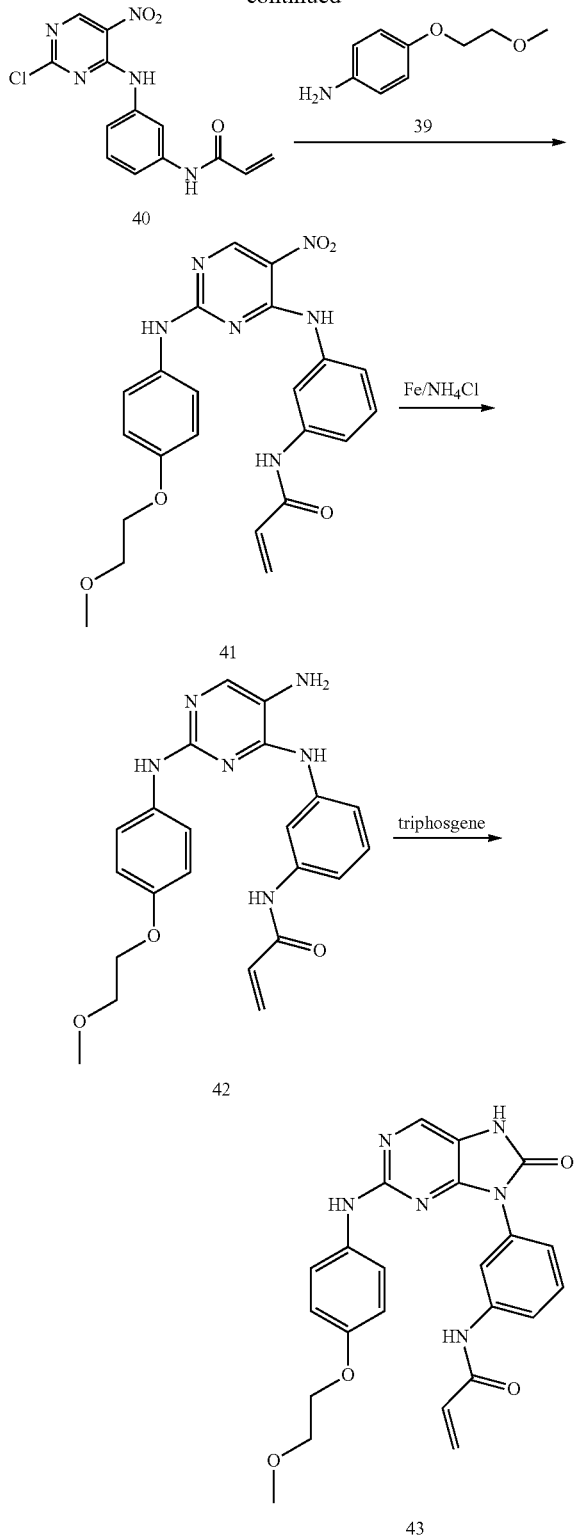

NaHCO₃, brine, dried over Na₂SO₄, and concentrated in reduced pressure to give N-(3-aminophenyl)acrylamide (37) (400 mg, 87%) as a white solid. LC-MS (ESI): m/z (M+1) 163.

To a solution of 4-nitrophenol (2.78 g, 20 mmol) and 2-bromoethyl methyl ether (3.6 g, 26 mmol) in DMF (10 mL) were added K₂CO₃ (5.52 g, 40 mmol) and the reaction was stirred at 80° C. for 5 h. The mixture was cooled down to rt and then quenched with H₂O (30 mL) and EtOAc (40 mL). The layers were separated and the aqueous layer was extracted with EtOAc (2×25 mL). The combined organic extracts were washed with brine (2×20 mL), dried (Na₂SO₄) and concentrated to afford 1-(2-methoxyethoxy)-4-nitrobenzene (38) (3.9 g, 100%) as a yellow solid.

1-(2-methoxyethoxy)-4-nitrobenzene (38) (3.9 g, 20 mmol), MeOH (80 mL), and 10% Pd on activated carbon (400 mg) were charged in a hydrogenation vessel and the reaction mixture was stirred at rt overnight under H₂ atmosphere. The mixture was filtered through the celite. The filtrate was concentrated in vacuo to afford 4-(2-methoxyethoxy)aniline (39) (3.1 g, 93%) as a black oil. LC-MS (ESI): m/z (M+1) 168.1.

To a stirred solution of 2,4-dichloro-5-nitropyrimidine (478 mg, 2.47 mmol) and DIPEA (636 mg, 4.93 mmol) in THF (5 mL) at −78° C. was added a solution of N-(3-aminophenyl)acrylamide (37) (400 mg, 2.47 mmol) in THF (5 mL). The mixture was allowed to warm to room temperature and stirred overnight. The solvent was removed in vacuo and the residue was purified by column chromatography (silica gel, 0 to 50% ethyl acetate in petroleum ether) to give N-(3-(2-chloro-5-nitropyrimidin-4-ylamino)phenyl) acrylamide (40) (600 mg, 76%). LC-MS (ESI): m/z (M+1) 320.3.

A sealed tube was charged with N-(3-(2-chloro-5-nitropyrimidin-4-ylamino)phenyl) acrylamide (40) (878 mg, 2.99 mmol), 4-(2-methoxyethoxy)aniline (39) (551 mg, 3.59 mmol), a drop of conc. HCl and n-BuOH (3 mL). The mixture was stirred at 120° C. under microwave for 45 mins. The reaction mixture was cooled down to −5° C. and a precipitate was generated. The precipitate was collected by filtration and dried to afford N-(3-(2-(4-(2-methoxyethoxyl)phenylamino)-5-nitropyrimidin-4-ylamino)phenyl)acrylamide (41) (945 mg, 70%) as a gray solid. LC-MS (ESI): m/z (M+1) 451.1.

N-(3-(5-Amino-2-(4-(2-methoxyethoxyl)phenylamino) pyrimidin-4-ylamino)phenyl)acrylamide (42) (400 mg, 46%) was obtained as a yellow solid from N-(3-(2-(4-(2-methoxyethoxyl)phenylamino)-5-nitropyrimidin-4-ylamino)phenyl)acrylamide (41) (945 mg, 2.1 mmol), following a similar procedure outlined in Example 1. LC-MS (ESI): m/z (M+1) 421.3.

N-(3-(2-(4-(2-Methoxyethoxyl)phenylamino)-8-oxo-7H-purin-9(8H)-yl)phenyl)acrylamide (43) (10 mg, 9%) was obtained as a yellow solid from N-(3-(5-amino-2-(4-(2-methoxyethoxyl)phenylamino)pyrimidin-4-ylamino)phenyl)acrylamide (42) (100 mg, 0.24 mmol), following a similar procedure outlined in Example 1. LC-MS (ESI): m/z (M+1) 447.3. ¹H NMR (400 MHz, DMSO) δ 11.21 (s, 1H), 10.37 (s, 1H), 9.19 (s, 1H), 7.99 (m, 2H), 7.71 (d, J=7.5 Hz, 1H), 7.55 (d, J=8.8 Hz, 2H), 7.49 (t, J=7.9 Hz, 1H), 7.32 (d, J=7.7 Hz, 1H), 6.77 (d, J=8.6 Hz, 2H), 6.46 (dd, J=17.1, 10.0 Hz, 1H), 6.27 (d, J=16.7 Hz, 1H), 5.78 (d, J=10.0 Hz, 1H), 4.00-3.96 (m, 2H), 3.62-3.57 (m, 2H), 3.28 (s, 3H).

To a solution of tert-butyl 3-aminophenylcarbamate (600 mg, 2.88 mmol) and Et₃N (582 mg, 5.76 mmol) in DCM (10 mL) at 0° C. was added acryloyl chloride (313 mg, 3.45 mmol). The mixture was stirred at rt for 2 hours before TFA (2.5 mL) was introduced. The mixture was stirred at rt for 1 hour before the solvent was removed in vacuo. The residue was dissolved in EA (20 mL) and washed with aqueous

Example 8

Synthesis of (E)-4-(dimethylamino)-N-(3-(2-(4-fluorophenylamino)-8-oxo-7H-purin-9(8H)-yl)phenyl)but-2-enamide (48)

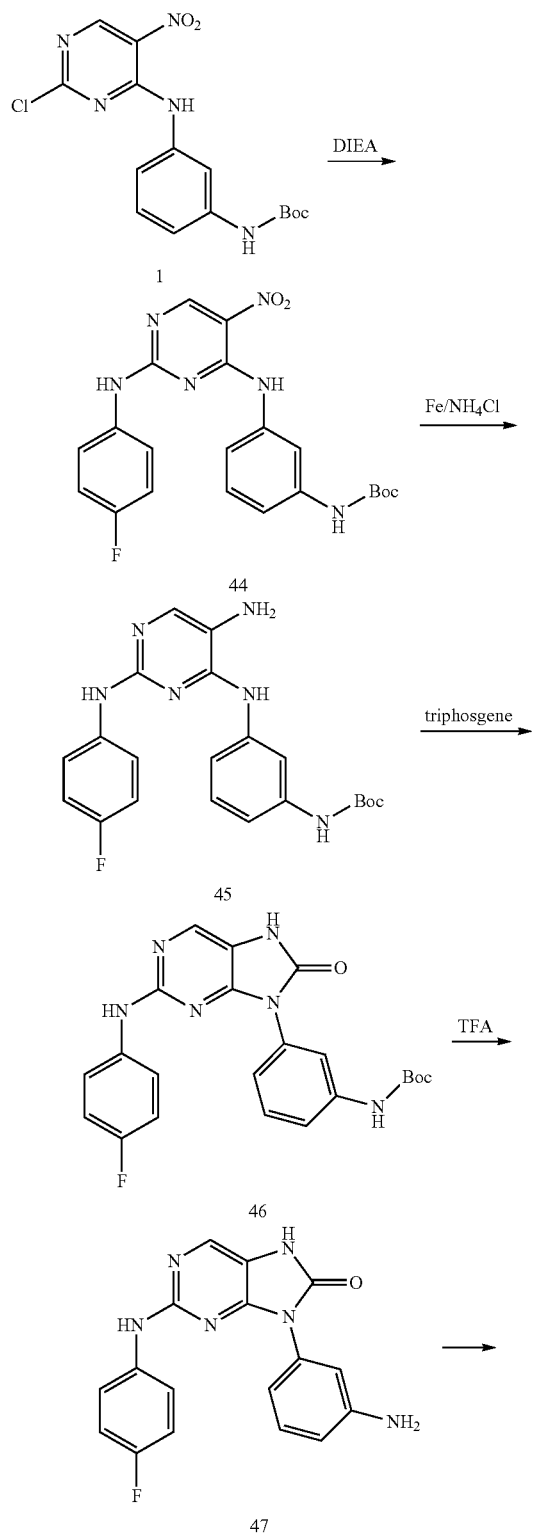

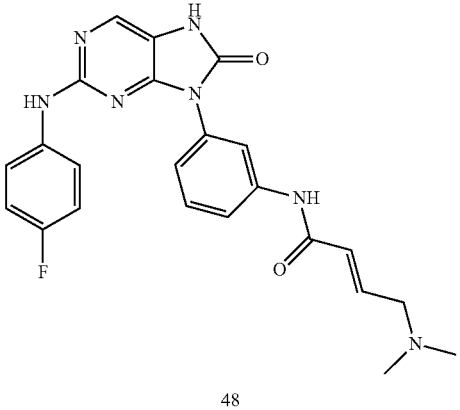 [SMILES: CN(C)C/C=C/C(=O)Nc1cccc(-n2c(=O)[nH]c3cnc(Nc4ccc(F)cc4)nc32)c1]

tert-Butyl 3-(2-(4-fluorophenylamino)-5-nitropyrimidin-4-ylamino)phenylcarbamate (44) (575 mg, quant. yield) was obtained from tert-butyl 3-(2-chloro-5-nitropyrimidin-4-ylamino)phenylcarbamate (1) (366 mg, 1 mmol) and 4-fluoroaniline (133 mg, 1.2 mmol), following a similar procedure outlined in Example 1. LC-MS (ESI): m/z (M+1) 441.0.

tert-Butyl 3-(5-amino-2-(4-fluorophenylamino)pyrimidin-4-ylamino)phenylcarbamate (45) (590 mg, 72%) was obtained from tert-butyl 3-(2-(4-fluorophenylamino)-5-nitropyrimidin-4-ylamino)phenylcarbamate (881 mg, 2 mmol) (44), following a similar procedure outlined in Example 1. LC-MS (ESI): m/z (M+1) 411.0.

tert-Butyl 3-(2-(4-fluorophenylamino)-8-oxo-7H-purin-9(8H)-yl)phenylcarbamate (46) (515 mg, 82%) was obtained from tert-butyl 3-(5-amino-2-(4-fluorophenylamino)pyrimidin-4-ylamino)phenylcarbamate (590 mg, 1.437 mmol) (45) and triphosgene (192 mg, 0.6 mmol), following a similar procedure outlined in Example 1. LC-MS (ESI): m/z (M+1) 437.0.

9-(3-Aminophenyl)-2-(4-fluorophenylamino)-7H-purin-8(9H)-one (47) (396 mg, 99%) was obtained from tert-butyl 3-(2-(4-fluorophenylamino)-8-oxo-7H-purin-9(8H)-yl)phenylcarbamate (46) (515 mg, 1.18 mmol), following a similar procedure outlined in Example 1. LC-MS (ESI): m/z (M+1) 337.1.

(E)-4-(Dimethylamino)-N-(3-(2-(4-fluorophenylamino)-8-oxo-7H-purin-9(8H)-yl)phenyl)but-2-enamide (48) (25 mg, 19%) was obtained as a white solid from 9-(3-aminophenyl)-2-(4-fluorophenylamino)-7H-purin-8(9H)-one (100 mg, 0.297 mmol) (47) and (E)-4-(dimeth-ylamino)but-2-enoic acid HCl salt (100 mg, 0.594 mmol) following a similar procedure outlined in Example 1. LC-MS (ESI): m/z (M+1) 448.1. $^1$H NMR (400 MHz, DMSO) δ 11.30-11.13 (br, 1H), 10.28 (s, 1H), 9.34 (s, 1H), 8.16 (s, 1H), 8.04 (s, 1H), 7.97 (s, 1H), 7.73-7.63 (m, 3H), 7.47 (t, J=8.2 Hz, 1H), 7.30 (d, J=7.3 Hz, 1H), 6.98 (t, J=8.9 Hz, 2H), 6.80-6.67 (m, 1H), 6.29 (d, J=15.5 Hz, 1H), 3.06 (d, J=5.2 Hz, 2H), 2.49-2.46 (s, 6H).

Example 9

Synthesis of N-(3-(5-(4-(2-methoxyethoxyl)phenylamino)-1H-pyrazolo[4,3-d]pyrimidin-3-yl)phenyl)acrylamide (54)

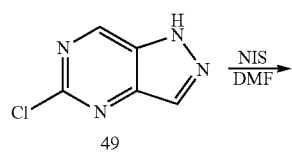

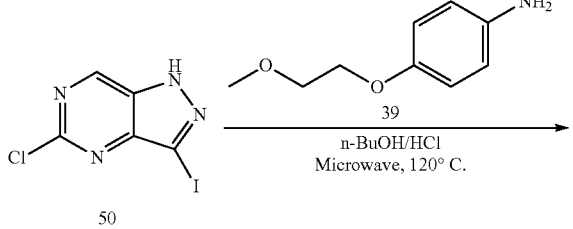

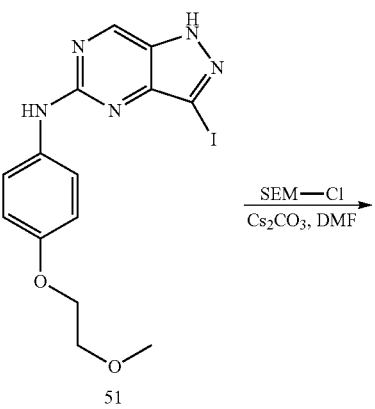

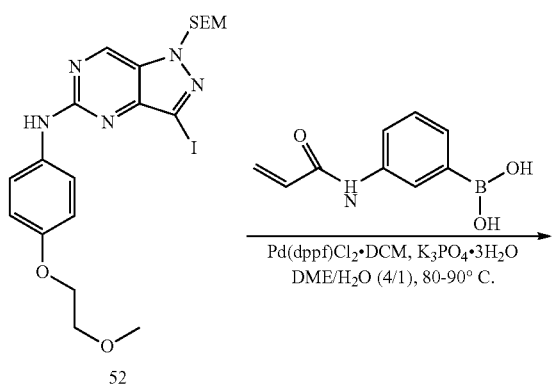

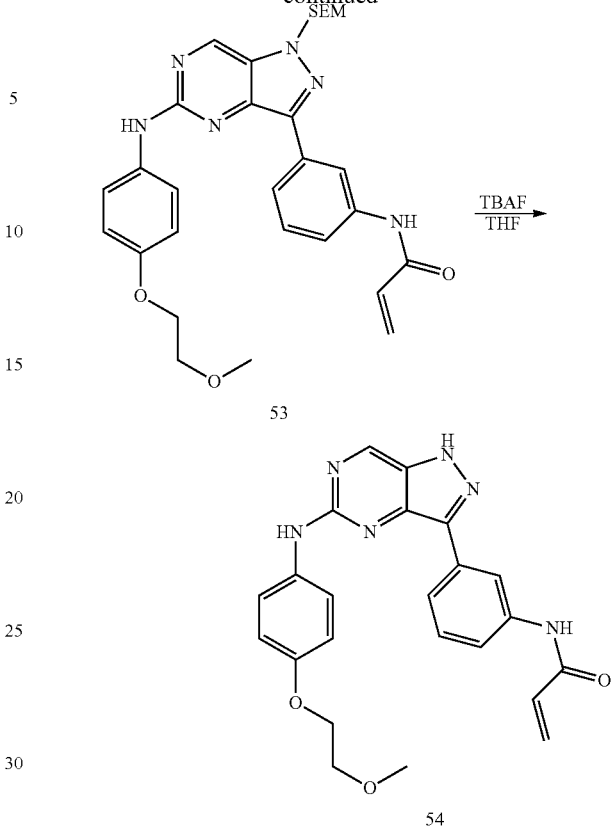

To a solution of 5-chloro-1H-pyrazolo[4,3-d]pyrimidine (49) (310 mg, 2 mmol) in DMF (5 mL) was added NIS (540 mg, 2.4 mmol). The resulting mixture was stirred at r.t. for 5 hrs. The solvent was removed in vacuo before water (1 mL) was introduced. The newly generated precipitate was filtered and dried to give crude 5-chloro-3-iodo-1H-pyrazolo[4,3-d]pyrimidine (50) (500 mg, 89%) as a light yellow solid. LC-MS (ESI): m/z (M/M+2) 280.4/282.4.

3-Iodo-N-(4-(2-methoxyethoxyl)phenyl)-1H-pyrazolo[4,3-d]pyrimidin-5-amine (51) (542 mg, yield 73%) was obtained as a light yellow solid from 5-chloro-3-iodo-1H-pyrazolo[4,3-d]pyrimidine (50) (500 mg, 1.8 mmol) and 4-(2-methoxyethoxy)aniline (39) (334 mg, 2 mmol), following a similar procedure outlined in Example 2. LC-MS (ESI): m/z (M+1) 412.0.

To a suspension of 3-iodo-N-(4-(2-methoxyethoxyl)phenyl)-1H-pyrazolo[4,3-d]pyrimidin-5-amine (51) (164 mg, 0.4 mmol) and $Cs_2CO_3$ (326 mg, 1 mmol) in DMF (1 mL) at 0° C. was added SEM-Cl (167 mg, 1 mmol). The resulting mixture was stirred at r.t. for 5 hours. The reaction mixture was concentrated in vacuo and the residue was purified by column chromatography (silica gel, 0 to 40% ethyl acetate in petroleum ether) to give 3-iodo-N-(4-(2-methoxyethoxyl)phenyl)-1-((2-(trimethylsilyl)ethoxy)methyl)-1H-pyrazolo[4,3-d]pyrimidin-5-amine (52) (210 mg, 86%) as a yellow oil. LC-MS (ESI): m/z (M+1) 542.2.

N-(3-(5-(4-(2-Methoxyethoxyl)phenylamino)-1-((2-(trimethylsilyl)ethoxy)methyl)-1H-pyrazolo[4,3-d]pyrimidin-3-yl)phenyl)acrylamide (53) (200 mg, yield 73%) was obtained as a light yellow solid from 3-iodo-N-(4-(2-methoxyethoxyl)phenyl)-1-((2-(trimethylsilyl)ethoxy)methyl)-1H-pyrazolo[4,3-d]pyrimidin-5-amine (52) (210 mg, 0.39 mmol) and 3-acrylamidophenylboronic acid (90 mg, 0.47 mmol) under Suzuki coupling conditions. LC-MS (ESI): m/z (M+1) 561.1.

N-(3-(5-(4-(2-Methoxyethoxyl)phenylamino)-1-((2-(trimethylsilyl)ethoxy)methyl)-1H-pyrazolo[4,3-d]pyrimidin-3-yl)phenyl)acrylamide (53) (100 mg, 0.19 mmol) was dissolved in a solution of TBAF in THF (1 M, 5 mL). The resulting mixture was heated to 50-60° C. for 4 hrs. The solvent was removed and the residue was pre-purified by column chromatography (silica gel, 0 to 5% DCM in MeOH), followed by preparative HPLC purification (RP C18, 10 to 95% acetonitrile in water (0.2% $NH_3$)) to give N-(3-(5-(4-(2-methoxyethoxyl)phenylamino)-1H-pyrazolo[4,3-d]pyrimidin-3-yl)phenyl)acrylamide (54) (38 mg, 46%) as a white solid. LC-MS (ESI): m/z (M−1) 431.2. $^1$H NMR (400 MHz, DMSO) δ 10.26 (s, 1H), 9.50 (s, 1H), 9.07 (s, 1H), 8.17 (d, J=7.7 Hz, 1H), 7.84 (d, J=9.0 Hz, 2H), 7.57 (d, J=8.1 Hz, 1H), 7.48 (t, J=8.0 Hz, 1H), 6.90 (d, J=9.0 Hz, 2H), 6.51 (dd, J=17.0, 10.1 Hz, 1H), 6.30 (d, J=17.2 Hz, 1H), 5.78 (d, J=12.0 Hz, 1H), 4.07-3.96 (m, 2H), 3.66-3.57 (m, 2H), 3.30 (s, 3H).

Example 10

Synthesis of N-(3-(2-(4-(2-methoxyethoxyl)phenylamino)-5H-pyrrolo[3,2-d]pyrimidin-7-yl)phenyl)acrylamide (60)

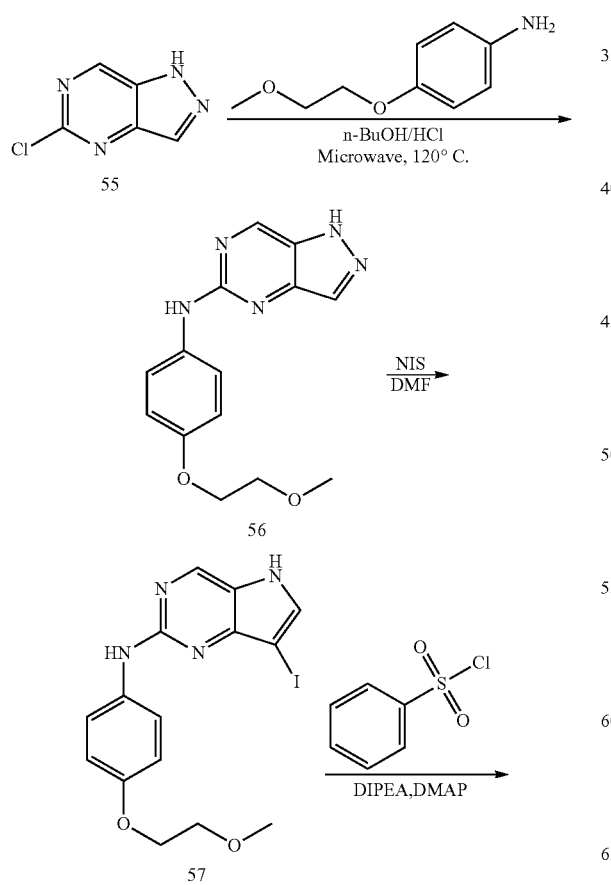

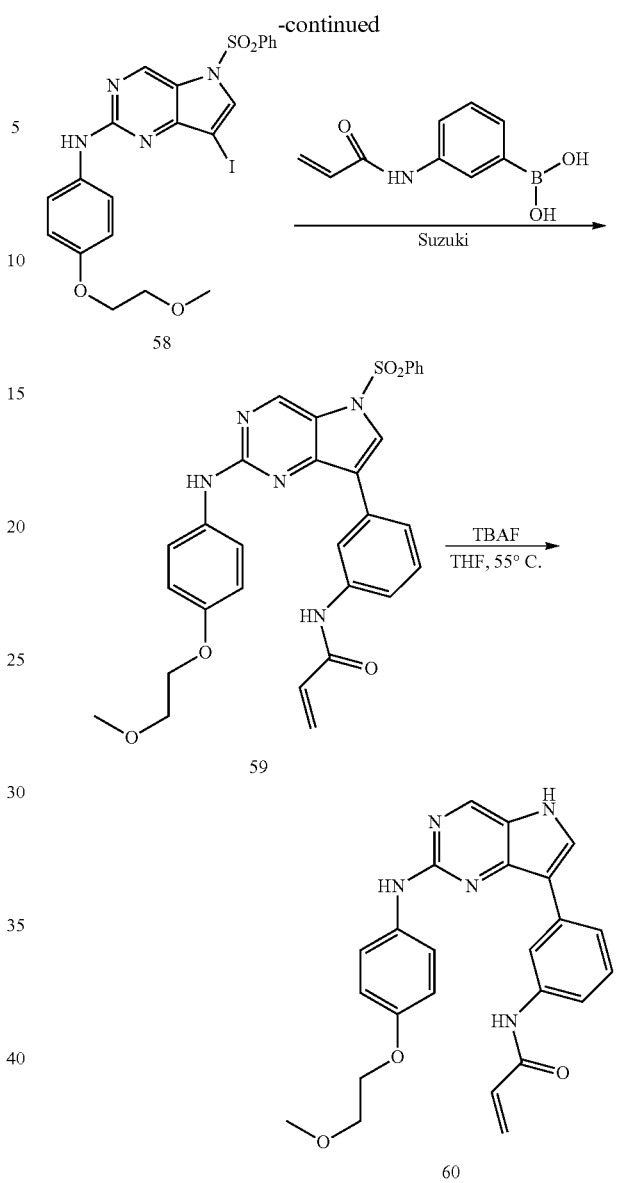

N-(4-(2-Methoxyethoxyl)phenyl)-5H-pyrrolo[3,2-d]pyrimidin-2-amine (56) (410 mg, yield 56%) was obtained as a light yellow solid from 2-chloro-5H-pyrrolo[3,2-d]pyrimidine (55) (400 mg, 2.6 mmol) and 4-(2-methoxyethoxy)aniline (524 mg, 3.13 mmol), following a similar procedure outlined in Example 2. LC-MS (ESI): m/z (M+1) 285.1.

7-Iodo-N-(4-(2-methoxyethoxyl)phenyl)-5H-pyrrolo[3,2-d]pyrimidin-2-amine (57) (550 mg, yield 56%) was obtained as a yellow solid from N-(4-(2-methoxyethoxyl)phenyl)-5H-pyrrolo[3,2-d]pyrimidin-2-amine (56) (410 mg, 1.44 mmol) and NIS (360 mg, 1.6 mmol), following a similar procedure outlined in Example 9. LC-MS (ESI): m/z (M+1) 411.0.

To a solution of 7-iodo-N-(4-(2-methoxyethoxyl)phenyl)-5H-pyrrolo[3,2-d]pyrimidin-2-amine (57) (100 mg, 0.24 mmol), DIPEA (0.1 mL, 0.56 mmol) and DMAP (10 mg, 0.08 mmol) in DCM (5 mL) was added benzenesulfonyl chloride (52 mg, 0.29 mmol). The resulting mixture was stirred at r.t. for 2 hrs. The solvent was removed in vacuo and the residue was purified by column chromatography (silica gel, 0 to 30% ethyl acetate in petroleum ether) to give 7-iodo-N-(4-(2-methoxyethoxyl)phenyl)-5-(phenylsulfonyl)-5H-pyrrolo[3,2-d]pyrimidin-2-amine (58) (170 mg, 75%) as a yellow solid. LC-MS (ESI): m/z (M+1) 551.0.

N-(3-(2-(4-(2-Methoxyethoxyl)phenylamino)-5-(phenylsulfonyl)-5H-pyrrolo[3,2-d]pyrimidin-7-yl)phenyl)acrylamide (59) (350 mg, yield 73%) was obtained as a light yellow solid from 7-iodo-N-(4-(2-methoxyethoxyl)phenyl)-5-(phenylsulfonyl)-5H-pyrrolo[3,2-d]pyrimidin-2-amine (58) (350 mg, 0.64 mmol) and 3-acrylamidophenylboronic acid (147 mg, 0.77 mmol) under Suzuki coupling conditions. LC-MS (ESI): m/z (M+1) 570.2.

N-(3-(2-(4-(2-Methoxyethoxyl)phenylamino)-5-(phenylsulfonyl)-5H-pyrrolo[3,2-d]pyrimidin-7-yl)phenyl)acrylamide (59) (100 mg, 0.176 mmol) was dissolved in a solution of TBAF in THF (1 M, 5 mL). The resulting mixture was heated to 50-60° C. for 4 hrs. The solvent was removed and the residue was pre-purified by column chromatography (silica gel, 0 to 10% DCM in MeOH), followed by preparative HPLC purification (RP C18, 10 to 95% acetonitrile in water (0.2% $NH_3$)) to give N-(3-(2-(4-(2-methoxyethoxyl)phenylamino)-5H-pyrrolo[3,2-d]pyrimidin-7-yl)phenyl)acrylamide (60) (65 mg, 84%). LC-MS (ESI): m/z (M−1) 430.2. $^1$H NMR (400 MHz, DMSO) δ 11.64 (br, 1H), 10.13 (s, 1H), 9.02 (s, 1H), 8.64 (s, 1H), 8.34 (s, 1H), 8.04 (s, 1H), 7.91-7.75 (m, 3H), 7.48-7.28 (m, 2H), 6.82 (d, J=9.0 Hz, 2H), 6.59-6.42 (m, 1H), 6.28 (dd, J=17.0, 1.9 Hz, 1H), 5.76 (dd, J=10.1, 1.9 Hz, 1H), 4.02-3.94 (m, 2H), 3.64-3.58 (m, 2H), 3.30 (s, 3H).

Example 11a

Btk In Vitro Inhibitory Activity (Method A)

The Btk $IC_{50}$s of compounds disclosed herein is determined in both a cellular kinase assay and in a cellular functional assay of BCR-induced calcium flux as described below.

Btk kinase activity is determined using a time-resolved fluorescence resonance energy transfer (TR-FRET) methodology. Measurements are performed in a reaction volume of 50 µL using 96-well assay plates. Kinase enzyme, inhibitor, ATP (at the $K_m$ for the kinase), and 1 µM peptide substrate (Biotin-AVLESEEELYSSARQ-$NH_2$) are incubated in a reaction buffer composed of 20 mM Tris, 50 mM NaCl, $MgCl_2$ (5-25 mM depending on the kinase), $MnCl_2$ (0-10 mM), 1 mM DTT, 0.1 mM EDTA, 0.01% bovine serum albumin, 0.005% Tween-20, and 10% DMSO at pH 7.4 for one hour. The reaction is quenched by the addition of 1.2 equivalents of EDTA (relative to divalent cation) in 25 µL of 1× Lance buffer (Perkin-Elmer). Streptavidin-APC (Perkin-Elmer) and Eu-labeled p-Tyr100 antibody (Perkin-Elmer) in 1× Lance buffer are added in a 25 µL volume to give final concentrations of 100 nM and 2.5 nM, respectively, and the mixture is allowed to incubate for one hour. The TR-FRET signal is measured on a multimode plate reader with an excitation wavelength ($λ_{Ex}$) of 330 nm and detection wavelengths ($λ_{Em}$) of 615 and 665 nm. Activity is determined by the ratio of the fluorescence at 665 nm to that at 615 nm. For each compound, enzyme activity is measured at various concentrations of compound. Negative control reactions are performed in the absence of inhibitor in replicates of six, and two no-enzyme controls are used to determine baseline fluorescence levels Inhibition constants, $K_i$(app), ware obtained using the program BatchK$_i$ (Kuzmic et al. (2000), Anal. Biochem. 286:45-50). $IC_{50}$s are obtained according to the equation:

$$IC_{50}=\{Ki(\text{app})/(1+[ATP]/K_m^{ATP})\}+[E]_{total}/2;$$

For all kinases, $[ATP]=K_m^{ATP}$, $[Btk]_{total}=0.5$ nM and $[Lck]_{total}=6$ nM.

Example 11b

Btk In Vitro Inhibitory Activity (Method B)

Kinase activity is measured in vitro using electrophoretic mobility shift assay. The kinase reactions are assembled in a total volume of 25 µL in 384 well plates. The reactions comprise: BTK enzyme (1 nM, N-terminal His6-tagged, recombinant, full-length, human BTK purified from baculovirus Sf21 insect cell system), inhibitor, ATP (16 µM, the apparent $K_m$ for the kinase), fluorescently labeled peptide substrate (1 µM, FAM-GEEPLYWSFPAKKK-$NH_2$) in a reaction buffer composed of 100 mM HEPES, pH7.5, 5 mM $MgCl_2$ 1 mM DTT, 0.1% bovine serum albumin, 0.01% Triton X-100, and 1% DMSO. The reaction is incubated for one hour and is quenched by the addition of 45 µL of termination buffer (100 mM HEPES, pH7.5, 0.01% Triton X-100, 30 mM EDTA). The terminated reactions are analyzed using 12 channel LabChip® 3000 microfluidic detection instrument (Caliper Life Sciences). The enzymatic phosphorylation of the peptide results in a change in net charge, enabling electrophoretic separation of product from substrate peptide. As substrate and product peptides are separated, two peaks of fluorescence are observed. Change in the relative fluorescence intensity of the substrate and product peaks is the parameter measured, reflecting enzyme activity. In the presence of an inhibitor, the ratio between product and substrate is altered: the signal of the product decreases, while the signal of the substrate increases. Activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each inhibitor at each concentration. Percent inhibition ($P_{inh}$) is determined using following equation:

$P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the average product sum ration in the absence of inhibitor and $PSR_{100\%}$ is the average product sum ratio in 100%-inhibition control samples;

The IC50 values of inhibitors are determined by 4 parameter sigmoidal dose-response model fitting of the inhibition curves ($P_{inh}$ versus inhibitor concentration) using XLfit 4 software.

Example 11c

Btk In Vitro Inhibitory Activity (Method C)

Human Btk kinase (Genbank accession # NP_000052) was purified from insect cells as a full-length construct containing a N-terminal 6×-His tag. Btk kinase activity was determined using a radiometric filter binding assay. Measurements are performed in a low µL reaction volume 384-well assay plates. BTK enzyme (8 nM final in reaction), inhibitor (at requested doses), and 0.2 mg/mL peptide substrate (Poly-Glu-Tyr, 4:1 ratio) are incubated in a reaction buffer composed of 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO for 15 min. followed by addition of 1 µM ATP to start the assay. Kinase reactions are carried out for 120 min. at RT. The reaction was stopped by spotting of reaction sample onto P81 cationic exchange paper (Whatman). Unbound phosphate was removed by extensive washing of filters in 0.75% Phosphoric acid. After subtraction of background derived from control reactions containing inactive enzyme (via addition of saturating EDTA), kinase activity data for each dose of compound tested was expressed as the percent of remaining kinase activity in test samples compared to vehicle (dimethyl sulfoxide) reactions. $IC_{50}$ values and curve fits were obtained using Prism (GraphPad Software).

Example 12

Inhibition of a Panel of Kinases

The degree of inhibition of a panel of kinases is determined using one of the methods outlined in Example 11a, 11b and 11c.

| Compound | BTK IC50 | EGFR IC50 | LCK IC50 |
|---|---|---|---|
| 6 | A | C | — |
| 13 | A | C | C |
| 17 | A | B | D |
| 23 | B | D | — |
| 29 | B | C | C |
| 35 | B | D | C |
| 43 | A | C | D |
| 48 | A | C | C |
| 54 | A | C | B |
| 60 | B | C | C |

$IC_{50}$: A < 100 nM;
100 nM ≤ B ≤ 1 μM;
1 μM < C ≤ 10 μM;
D > 10 μM;
— = no data Example 13

Pharmaceutical Compositions

The compositions described below are presented with a compound of Formula (I), (Ia), (Ib), (Ic), (Id), (II), (IIa), (III), (IIIa), (IV), or (IVa) for illustrative purposes.

Example 13a

Parenteral Composition

To prepare a parenteral pharmaceutical composition suitable for administration by injection, 100 mg of a water-soluble salt of a compound of Formula (I), (Ia), (Ib), (Ic), (Id), (II), (IIa), (III), (IIIa), (IV), or (IVa) is dissolved in DMSO and then mixed with 10 mL of 0.9% sterile saline. The mixture is incorporated into a dosage unit form suitable for administration by injection.

Example 13b

Oral Composition

To prepare a pharmaceutical composition for oral delivery, 100 mg of a compound of Formula (I), (Ia), (Ib), (Ic), (Id), (II), (IIa), (III), (IIIa), (IV), or (IVa) is mixed with 750 mg of starch. The mixture is incorporated into an oral dosage unit for, such as a hard gelatin capsule, which is suitable for oral administration.

Example 13c

Sublingual (Hard Lozenge) Composition

To prepare a pharmaceutical composition for buccal delivery, such as a hard lozenge, mix 100 mg of a compound of Formula (I), (Ia), (Ib), (Ic), (Id), (II), (IIa), (III), (IIIa), (IV), or (IVa), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 13d

Inhalation Composition

To prepare a pharmaceutical composition for inhalation delivery, 20 mg of a compound of Formula (I), (Ia), (Ib), (Ic), (Id), (II), (IIa), (III), (IIIa), (IV), and (IVa) is mixed with 50 mg of anhydrous citric acid and 100 mL of 0.9% sodium chloride solution. The mixture is incorporated into an inhalation delivery unit, such as a nebulizer, which is suitable for inhalation administration.

Example 13e

Rectal Gel Composition

To prepare a pharmaceutical composition for rectal delivery, 100 mg of a compound of Formula (I), (Ia), (Ib), (Ic), (Id), (II), (IIa), (III), (IIIa), (IV), or (IVa) is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 13f

Topical Gel Composition

To prepare a pharmaceutical topical gel composition, 100 mg of a compound of Formula (I), (Ia), (Ib), (Ic), (Id), (II), (IIa), (III), (IIIa), (IV), or (IVa) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 13g

Ophthalmic Solution Composition

To prepare a pharmaceutical ophthalmic solution composition, 100 mg of a compound of Formula (I), (Ia), (Ib), (Ic), (Id), (II), (IIa), (III), (IIIa), (IV), or (IVa) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 14

Clinical Trial of a Compound of Formula (I), (Ia), (Ib), (Ic), (Id), (II), (IIa), (III), (IIIa), (IV), or (IVa) and Combination Chemotherapy in Treating Older Patients with Previously Untreated B-Cell Lymphoma The purpose purpose of this study is to determine how well giving a compound of Formula (I), (Ia), (Ib), (Ic), (Id), (II), (IIa), (III), (IIIa), (IV), or (IVa) together with combination chemotherapy works in treating older patients with previously untreated B cell lymphoma.

Criteria

Disease Characteristics:
Histological diagnosis of aggressive B-cell lymphoma
Previously untreated disease
Stage I-IV disease
CD20-positive disease
Any International Prognostic Index (IPI) score
No secondary lymphoma after prior chemotherapy or radiotherapy
No primary CNS lymphoma
No primary gastrointestinal (MALT) lymphoma Patient Characteristics:
ECOG performance status 0-2
Life expectancy≥3 months
AST and ALT≤3 times normal unless related to lymphoma
Bilirubin≤2 mg/dL unless related to lymphoma
Creatinine≤2 times normal unless related to lymphoma
Fertile patients must use effective contraception
No known allergic reactions against foreign proteins
No active infections requiring systemically administered antibiotics or antiviral medications
No noncompensated heart failure
No dilatative cardiomyopathy
No coronary heart disease with ST-segment depression in ECG
No myocardial infarction during the past 6 months
No chronic lung disease with hypoxemia
No severe noncompensated hypertension
No severe noncompensated diabetes mellitus
No clinical signs of cerebral dysfunction
No severe psychiatric disease
No known HIV infection
No active chronic hepatitis B or C infection
No other concurrent diseases that exclude the administration of therapy as outlined by the study protocol
More than 12 weeks since prior clinical trial participation
No prior participation in this study
No prior therapy, including murine antibody, for this cancer
No prior organ transplantation
No concurrent response-adapted radiotherapy ("iceberg radiotherapy")
No other concurrent anticancer chemotherapy or other study medication Study Design
Ages Eligible for Study: 61 Years to 80 Years
Genders Eligible for Study: Both
Accepts Healthy Volunteers: No
All patients undergo the following treatment.
Prephase treatment: Patients receive vincristine subcutaneously on day −6 and oral prednisone on days −6 to 0.
Immunochemotherapy and radiotherapy: Patients receive CHOP chemotherapy comprising cyclophosphamide IV over 15 minutes, doxorubicin hydrochloride IV, and vincristine IV on day 1 and oral prednisone once daily on days 1-5. Patients also receive pegfilgrastim subcutaneously on days 4, 18, and 32. Treatment with CHOP chemotherapy repeats every 14 days for up to 6 courses in the absence of disease progression or unacceptable toxicity. Patients who show no response after course 4 of CHOP chemotherapy proceed to salvage chemotherapy off study.

Patients are evaluated 2-4 weeks after completion of CHOP. Patients with initial bulky disease (i.e., diameter≥7.5 cm) or extranodal involvement AND achieving complete remission (CR), unconfirmed CR (CRu), or partial remission undergo radiotherapy 5 days a week for 4 weeks. Patients who do not achieve CR or CRu 2 months after completion of radiotherapy proceed to salvage chemotherapy off study.

Patients are then stratified according to center, International Prognostic Index (1-2 vs 3-5), disease involvement (bulky vs extranodal vs bulky and/or extranodal), age (61-70 years old vs 71-80 years old), and gender. Patients are randomized to 1 of 2 treatment arms.

Arm I: Patients receive compound of Formula (I), (Ia), (Ib), (II), (IIa), (IIb), (III), (IIIa), (IIIb), or (IIIc) at 500 mg once daily for 105 days.

Arm II (pharmacokinetic-based dose of compound of Formula (I), (Ia), (Ib), (II), (IIa), (IIb), (III), (IIIa), (IIIb), or (IIIc)) at 500 mg once daily for 35 days.

Some patients undergo blood sample collection periodically during and after treatment for pharmacokinetic studies.

After completion of study treatment, patients are followed every 3 months for 2 years, every 6 months for 3 years, and then once a year thereafter.

Primary Outcome Measures

Pharmacokinetics (in first 20 patients of each cohort with a distinct variation of the compound of Formula (I), (Ia), (Ib), (II), (IIa), (IIb), (III), (IIIa), (IIIb), or (IIIc) schedule)

Safety and treatment related deaths at 3 months after study completion

Toxicity assessed by NCI criteria, adverse events, serious adverse events, protocol adherence, and treatment-related deaths at 3 months after study completion Secondary Outcome Measures Time to treatment failure assessed at 2 years within the study and periodically thereafter Complete response rate assessed at 2 years within the study and periodically thereafter Progression rate Survival time Progression-free survival It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula (II) having the structure:

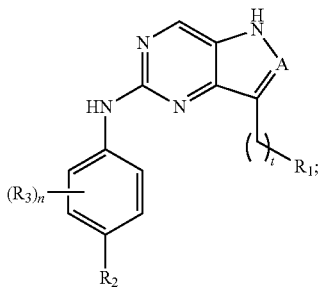

Formula (II)

wherein:

A is =C($R_9$)—, or =N—;

$R_1$ is substituted or unsubstituted alkoxy, substituted or unsubstituted heteroalkyl, substituted or unsubstituted heterocycloalkyl, substituted or unsubstituted cycloalkyl, substituted or unsubstituted heteroaryl, —(C=O)O$R_4$, —(C=O)NR$_4$R$_4$, —(C=O)SR$_4$, —Y-$L_2$-Ar, or

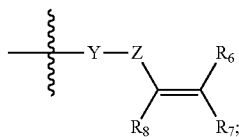

G is optionally substituted alkyl;

X is optionally substituted cycloalkyl, optionally substituted heterocycloalkyl, optionally substituted aryl, optionally substituted heteroaryl, —OR$_4$, —SR$_4$, —NR$_4$R$_4$, or -$L_2$-Ar;

each $R_4$ is each independently H, $C_1$-$C_6$ alkyl, $C_1$-$C_6$ heteroalkyl, $C_3$-$C_6$ cycloalkyl, or $C_2$-$C_6$ heterocycloalkyl;

Y is an optionally substituted group selected from among alkyl, heteroalkyl, cycloalkyl, heterocycloalkyl, aryl, and heteroaryl;

$R_2$ is hydrogen, halogen, —CN, —NO$_2$, —OH, —OR$_D$), —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted heteroalkyl, substituted or unsubstituted heterocycloalkyl, substituted or unsubstituted cycloalkyl, or -$L_2$-Ar;

$L_2$ is a bond, —CH$_2$—, —CH(OH)—, —C(O)—, —CH$_2$O—, —OCH$_2$—, —SCH$_2$, —CH$_2$S—, —N(R$_{21}$)—, —O—, —S—, —S(O)—, —S(O)$_2$—, —N(R$_{21}$)S(O)$_2$—, or —S(O)$_2$N(R$_{21}$)—;

Ar is a substituted or unsubstituted cycloalkyl, substituted or unsubstituted heterocycloalkyl, substituted or unsubstituted aryl, or a substituted or unsubstituted heteroaryl;

Z is —C(=O)—, —OC(=O)—, —N(R$_{21}$)C(=O)—, —C(=S)—, —S(=O)$_p$—, —OS(=O)$_p$—, or —N(R$_{21}$)S(=O)$_p$—, where p is 1 or 2;

each $R_3$ is each independently halogen, —CN, —NO$_2$, —OH, —OCF$_3$, —OCH$_2$F, —OCF$_2$H, —CF$_3$, —SR$_{21}$, —N(R$_{21}$)S(=O)$_2$R$_{23}$, —S(=O)$_2$N(R$_{21}$)(R$_{22}$), —S(=O)R$_{23}$, —S(=O)$_2$R$_{23}$, —C(=O)R$_{23}$, —OC(=O)R$_{23}$, —CO$_2$R$_{21}$, —N(R$_{21}$)(R$_{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R_{20}$ is substituted or unsubstituted $C_1$-$C_6$alkyl, substituted or unsubstituted $C_1$-$C_8$heteroalkyl, or substituted or unsubstituted phenyl;

each $R_{21}$ and $R_{22}$ are each independently H, substituted or unsubstituted $C_1$-$C_6$alkyl, or substituted or unsubstituted $C_3$-$C_8$cycloalkyl;

$R_{23}$ is each independently substituted or unsubstituted $C_1$-$C_6$alkyl, or substituted or unsubstituted $C_3$-$C_8$cycloalkyl;

n is 0-4;

t is 0-2;

$R_9$ is H, halogen, —CN, —OH, —NH$_2$, —SH, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;

$R_6$ is H, halogen, —CN, or $L_3$-J-W;

$R_7$ and $R_8$ are independently H, halogen, —CN, or $L_3$-J-W; or $R_7$ and $R_8$ taken together form a bond;

each $L_3$ and J are each independently a bond, substituted or unsubstituted $C_1$-$C_6$ alkylene, substituted or unsubstituted $C_3$-$C_6$ cycloalkylene, substituted or unsubstituted $C_1$-$C_6$ heteroalkylene, substituted or unsubstituted $C_2$-$C_7$ heterocycloalkylene, substituted or unsubstituted $C_6$-$C_{12}$ arylene, substituted or unsubstituted $C_3$-$C_{12}$ heteroarylene, —C(=O)—, —O—, or —S—;

each W is H, —CN, or —NR$_{25}$R$_{26}$;

$R_{25}$ and $R_{26}$ are each independently H, substituted or unsubstituted $C_1$-$C_6$ alkyl, substituted or unsubstituted $C_3$-$C_6$ cycloalkyl, substituted or unsubstituted $C_1$-$C_6$ heteroalkyl, substituted or unsubstituted $C_2$-$C_7$ heterocycloalkyl, substituted or unsubstituted $C_6$-$C_{12}$ aryl, or substituted or unsubstituted $C_3$-$C_{12}$ heteroaryl;

or a stereoisomer thereof;

or a pharmaceutically acceptable solvate, pharmaceutically acceptable salt, or pharmaceutically acceptable prodrug thereof.

2. A pharmaceutical composition comprising a therapeutically effective amount of a compound of claim 1, and a pharmaceutically acceptable excipient.

3. The compound of claim 1, wherein $R_1$ is

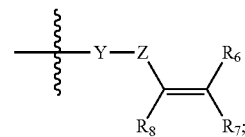

or a stereoisomer thereof.

4. The compound of claim 3, wherein Z is —C(=O)—, —NHC(=O)—, —N(CH$_3$)C(=O)—, or —S(=O)$_2$—; or a stereoisomer thereof.

5. The compound of claim 4, wherein $R_6$, $R_7$, and $R_8$ are H.

6. The compound of claim 3, wherein $R_7$ and $R_8$ taken together form a bond; and $R_6$ is H.

7. The compound of claim 3, wherein $R_7$ and $R_8$ are H; and $R_6$ is $L_3$-J-W; or $R_6$ and $R_8$ are H; and $R_7$ is $L_3$-J-W; or a stereoisomer thereof.

8. The compound of claim 3, wherein Y is aryl; or a stereoisomer thereof.

9. The compound of claim 3, wherein Y is heterocycloalkyl; or a stereoisomer thereof.

10. The compound of claim 3, wherein Y is cycloalkyl; or a stereoisomer thereof.

11. The compound of claim 1, wherein t is 0; or a stereoisomer thereof.

12. The compound of claim 1, wherein n is 0; or a stereoisomer thereof.

13. The compound of claim 1, wherein $R_2$ is halogen, —$OR_{20}$, or substituted or unsubstituted alkyl; or a stereoisomer thereof.

14. The compound of claim 13, wherein $R_2$ is —$OR_{20}$; or a stereoisomer thereof.

15. The compound of claim 14, wherein $R_{20}$ is substituted or unsubstituted alkyl; or a stereoisomer thereof.

16. The compound of claim 15, wherein the compound is represented by the following structure:

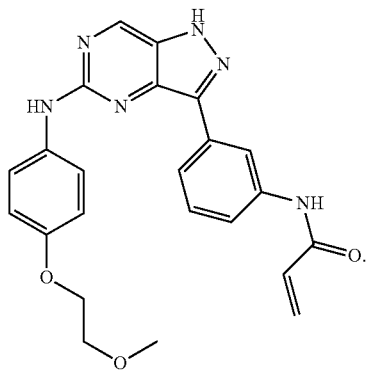 [SMILES: C=CC(=O)Nc1cccc(-c2n[nH]c3cnc(Nc4ccc(OCCOC)cc4)nc23)c1]

17. The compound of claim 1, wherein A is =C($R_9$)—; or a stereoisomer thereof.

18. The compound of claim 1, wherein A is =N—; or a stereoisomer thereof.

* * * * *